(12) United States Patent
Pletcher

(10) Patent No.: US 10,184,031 B2
(45) Date of Patent: Jan. 22, 2019

(54) MELT-STABILIZED ULTRA HIGH MOLECULAR WEIGHT POLYETHYLENE AND METHOD OF MAKING THE SAME

(71) Applicant: Zimmer, Inc., Warsaw, IN (US)

(72) Inventor: Dirk Pletcher, Walkerton, IN (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 15/124,454

(22) PCT Filed: Feb. 26, 2015

(86) PCT No.: PCT/US2015/017741
§ 371 (c)(1),
(2) Date: Sep. 8, 2016

(87) PCT Pub. No.: WO2015/138137
PCT Pub. Date: Sep. 17, 2015

(65) Prior Publication Data
US 2017/0015794 A1    Jan. 19, 2017

Related U.S. Application Data

(60) Provisional application No. 61/951,661, filed on Mar. 12, 2014.

(51) Int. Cl.
| | |
|---|---|
| *C08J 3/205* | (2006.01) |
| *A61L 27/16* | (2006.01) |
| *B29C 71/00* | (2006.01) |
| *B29C 71/02* | (2006.01) |
| *B29C 43/00* | (2006.01) |
| *C08J 7/06* | (2006.01) |
| *C08J 7/12* | (2006.01) |
| *C08K 5/00* | (2006.01) |
| *C08K 5/134* | (2006.01) |
| *C08K 5/1545* | (2006.01) |
| *C08L 23/06* | (2006.01) |
| *C08L 23/26* | (2006.01) |
| *A61L 27/50* | (2006.01) |
| *B29K 23/00* | (2006.01) |
| *B29K 105/00* | (2006.01) |
| *B29L 31/00* | (2006.01) |

(52) U.S. Cl.
CPC ............ *C08J 3/2056* (2013.01); *A61L 27/16* (2013.01); *A61L 27/505* (2013.01); *B29C 43/003* (2013.01); *B29C 71/0009* (2013.01); *B29C 71/02* (2013.01); *C08J 7/065* (2013.01); *C08J 7/08* (2013.01); *C08J 7/12* (2013.01); *C08K 5/005* (2013.01); *C08K 5/134* (2013.01); *C08K 5/1545* (2013.01); *C08L 23/06* (2013.01); *C08L 23/26* (2013.01); *A61L 2430/02* (2013.01); *A61L 2430/24* (2013.01); *B29C 2071/0018* (2013.01); *B29K 2023/0683* (2013.01); *B29K 2105/0044* (2013.01); *B29L 2031/7532* (2013.01); *C08J 2323/06* (2013.01); *C08K 2201/013* (2013.01); *C08L 2207/068* (2013.01)

(58) Field of Classification Search
None
See application file for complete search history.

(56) References Cited

U.S. PATENT DOCUMENTS

| | | | |
|---|---|---|---|
| 5,308,549 A | 5/1994 | Laermer et al. | |
| 5,414,049 A | 5/1995 | Sun et al. | |
| 5,559,167 A | 9/1996 | Mahood | |
| 5,577,368 A | 11/1996 | Hamilton et al. | |
| 5,721,334 A | 2/1998 | Burstein et al. | |
| 5,753,182 A | 5/1998 | Higgins | |
| 5,824,411 A | 10/1998 | Shalaby et al. | |
| 5,827,904 A * | 10/1998 | Hahn | A61L 27/16 523/113 |

(Continued)

FOREIGN PATENT DOCUMENTS

| | | |
|---|---|---|
| AU | 2006283596 A1 | 1/2007 |
| AU | 2006350369 A1 | 8/2008 |

(Continued)

OTHER PUBLICATIONS

US 7,253,214, 08/2007, McKellop et al. (withdrawn)
"U.S. Appl. No. 14/983,006, Corrected Notice of Allowance dated Dec. 13, 2017", 5 pgs.
"U.S. Appl. No. 15/073,042, Non Final Office Action dated Dec. 18, 2017", 15 pgs.
"U.S. Appl. No. 15/783,649, Non Final Office Action dated Jan. 5, 2018", 9 pgs.
"U.S. Appl. No. 15/783,649, Non Final Office Action dated Jan. 17, 2018", 10 pgs.
"U.S. Appl. No. 15/073,042, Response filed Jan. 1, 2018 to Non-Final Office Action dated Dec. 18, 2017", 14 pgs.

(Continued)

*Primary Examiner* — Peter A Salamon
(74) *Attorney, Agent, or Firm* — Schwegman Lundberg & Woessner, P.A.

(57) ABSTRACT

Various embodiments disclosed relate to melt-stabilized materials including ultra high molecular weight polyethylene (UHMWPE), methods of making the same, and medical implants including the same. In various embodiments, the present invention provides a method of melt-stabilizing a material including UHMWPE. The method includes obtaining or providing a solid material including UHMWPE including a first concentration of free-radicals. The method includes coating at least part of the solid material with a liquid composition including at least one antioxidant, to provide a coated solid material. The method includes heating the coated solid material in an environment including oxygen, the heating being sufficient to melt at least part of the UHMWPE, to provide a heated material. The method also includes solidifying the heated material, to provide a melt-stabilized material including UHMWPE including a second concentration of free-radicals, wherein the second concentration of free-radicals is less than the first concentration of free-radicals.

20 Claims, 39 Drawing Sheets

(56) References Cited

U.S. PATENT DOCUMENTS

| | | | |
|---|---|---|---|
| 5,879,400 A * | 3/1999 | Merrill | A61F 2/32 526/352 |
| 6,017,975 A | 1/2000 | Saum et al. | |
| 6,087,553 A | 7/2000 | Cohen et al. | |
| 6,087,559 A | 7/2000 | Cohen et al. | |
| 6,156,845 A | 12/2000 | Saito et al. | |
| 6,156,913 A | 12/2000 | Hyatt | |
| 6,184,265 B1 | 2/2001 | Hamilton et al. | |
| 6,204,257 B1 | 3/2001 | Stella et al. | |
| 6,228,900 B1 | 5/2001 | Shen et al. | |
| 6,231,804 B1 | 5/2001 | Yamauchi et al. | |
| 6,242,227 B1 | 6/2001 | Millis et al. | |
| 6,242,507 B1 | 6/2001 | Saum et al. | |
| 6,245,276 B1 | 6/2001 | McNulty et al. | |
| 6,277,390 B1 * | 8/2001 | Schaffner | A61L 27/16 424/422 |
| 6,391,390 B1 | 5/2002 | Boisseau et al. | |
| 6,432,349 B1 | 8/2002 | Pletcher et al. | |
| 6,437,048 B1 | 8/2002 | Saito et al. | |
| 6,448,315 B1 * | 9/2002 | Lidgren | A61L 27/16 524/110 |
| 6,464,926 B1 | 10/2002 | Merrill et al. | |
| 6,494,917 B1 * | 12/2002 | McKellop | A61F 2/30767 623/18.11 |
| 6,503,439 B1 | 1/2003 | Burstein | |
| 6,558,794 B1 | 5/2003 | Fehrenbacher et al. | |
| 6,562,540 B2 | 5/2003 | Saum et al. | |
| 6,620,198 B2 | 9/2003 | Burstein et al. | |
| 6,627,141 B2 * | 9/2003 | McNulty | B29B 11/06 264/322 |
| 6,641,617 B1 * | 11/2003 | Merrill | A61F 2/32 623/22.21 |
| 6,664,308 B2 | 12/2003 | Sun et al. | |
| 6,664,317 B2 | 12/2003 | King, III | |
| 6,692,679 B1 * | 2/2004 | McNulty | B29B 13/08 422/22 |
| 6,786,933 B2 | 9/2004 | Merrill et al. | |
| 6,818,020 B2 | 11/2004 | Sun et al. | |
| 6,818,172 B2 | 11/2004 | King et al. | |
| 6,852,772 B2 | 2/2005 | Muratoglu et al. | |
| 6,853,772 B2 | 2/2005 | Battiato et al. | |
| 6,872,764 B2 | 3/2005 | King, III | |
| 6,933,026 B2 | 8/2005 | Mauze | |
| 7,094,472 B2 | 8/2006 | Du Plessis et al. | |
| 7,160,492 B2 | 1/2007 | King | |
| 7,166,650 B2 | 1/2007 | Muratoglu et al. | |
| 7,214,764 B2 | 5/2007 | King | |
| 7,259,198 B2 | 8/2007 | Vaillant | |
| 7,304,097 B2 | 12/2007 | Muratoglu et al. | |
| 7,323,522 B2 | 1/2008 | Ideno et al. | |
| 7,335,697 B2 | 2/2008 | King et al. | |
| 7,384,430 B2 | 6/2008 | Greer et al. | |
| 7,431,874 B2 * | 10/2008 | Muratoglu | A61L 27/16 264/235 |
| 7,435,372 B2 | 10/2008 | Mimmnaugh et al. | |
| 7,445,641 B1 | 11/2008 | Ornberg et al. | |
| 7,498,365 B2 | 3/2009 | Muratoglu et al. | |
| 7,507,774 B2 | 3/2009 | Muratoglu et al. | |
| 7,569,620 B2 | 8/2009 | Muratoglu et al. | |
| 7,595,074 B2 | 9/2009 | Cholli et al. | |
| 7,615,075 B2 | 11/2009 | Kunze et al. | |
| 7,635,725 B2 | 12/2009 | Ballare et al. | |
| 7,683,133 B2 | 3/2010 | King et al. | |
| 7,705,075 B2 | 4/2010 | Kumar et al. | |
| 7,705,176 B2 | 4/2010 | Cholli et al. | |
| 7,790,095 B2 | 9/2010 | Muratoglu et al. | |
| 7,806,064 B2 | 10/2010 | Wellman | |
| 7,833,452 B2 | 11/2010 | Muratoglu et al. | |
| 7,846,376 B2 | 12/2010 | Abt et al. | |
| 7,863,348 B2 | 1/2011 | Abt et al. | |
| 8,129,440 B2 | 3/2012 | Rufner et al. | |
| 8,178,594 B2 | 5/2012 | Rufner et al. | |
| 8,399,535 B2 | 3/2013 | Pletcher | |
| 8,470,903 B2 | 6/2013 | Abt et al. | |
| 8,586,667 B2 * | 11/2013 | Brunner | C08J 5/10 523/300 |
| 8,664,290 B2 | 3/2014 | Rufner et al. | |
| 8,669,299 B2 | 3/2014 | Rufner et al. | |
| 8,673,202 B2 | 3/2014 | Abt et al. | |
| 9,265,545 B2 | 2/2016 | Rufner et al. | |
| 9,277,949 B2 | 3/2016 | Rufner et al. | |
| 9,370,602 B2 | 6/2016 | Thomas et al. | |
| 9,822,224 B2 | 11/2017 | Rufner et al. | |
| 9,926,432 B2 | 3/2018 | Rufner et al. | |
| 9,962,463 B2 * | 5/2018 | Muratoglu | A61L 27/16 |
| 2001/0027345 A1 | 10/2001 | Merrill et al. | |
| 2001/0049401 A1 | 12/2001 | Salovey et al. | |
| 2002/0007219 A1 | 1/2002 | Merrill et al. | |
| 2002/0086924 A1 * | 7/2002 | King, III | C08K 5/16 524/237 |
| 2002/0156536 A1 | 10/2002 | Harris et al. | |
| 2003/0013781 A1 | 1/2003 | Merrill et al. | |
| 2003/0045603 A1 | 3/2003 | Salovey et al. | |
| 2003/0105182 A1 | 6/2003 | Merrill et al. | |
| 2003/0119935 A1 | 6/2003 | Merrill et al. | |
| 2003/0127778 A1 | 7/2003 | Scott et al. | |
| 2003/0149125 A1 | 8/2003 | Muratoglu et al. | |
| 2003/0158287 A1 | 8/2003 | Salovey et al. | |
| 2003/0212161 A1 | 11/2003 | McKellop et al. | |
| 2004/0051213 A1 * | 3/2004 | Muratoglu | A61F 2/30 264/494 |
| 2004/0156879 A1 * | 8/2004 | Muratoglu | A61L 27/16 424/423 |
| 2004/0265165 A1 | 12/2004 | King | |
| 2005/0006821 A1 | 1/2005 | Merrill et al. | |
| 2005/0019371 A1 | 1/2005 | Anderson et al. | |
| 2005/0056971 A1 | 3/2005 | Merrill et al. | |
| 2005/0059750 A1 | 3/2005 | Sun et al. | |
| 2005/0096749 A1 | 5/2005 | Merrill et al. | |
| 2005/0124718 A1 | 6/2005 | Muratoglu et al. | |
| 2005/0125074 A1 | 6/2005 | Salovey et al. | |
| 2005/0146070 A1 | 7/2005 | Muratoglu et al. | |
| 2005/0165495 A1 | 7/2005 | Merrill et al. | |
| 2005/0194722 A1 | 9/2005 | Muratoglu et al. | |
| 2005/0194723 A1 | 9/2005 | Muratoglu et al. | |
| 2005/0267594 A1 | 12/2005 | Merrill et al. | |
| 2006/0079597 A1 | 4/2006 | Muratoglu et al. | |
| 2006/0115668 A1 | 6/2006 | King et al. | |
| 2006/0264541 A1 | 11/2006 | Lederer et al. | |
| 2007/0004818 A1 | 1/2007 | Muratoglu et al. | |
| 2007/0043137 A1 | 2/2007 | Muratoglu et al. | |
| 2007/0059334 A1 | 3/2007 | Abt et al. | |
| 2007/0077268 A1 | 4/2007 | King et al. | |
| 2007/0114702 A1 | 5/2007 | Muratoglu et al. | |
| 2007/0149660 A1 | 6/2007 | Kumar et al. | |
| 2007/0191504 A1 | 8/2007 | Muratoglu | |
| 2007/0232762 A1 | 10/2007 | Ernsberger et al. | |
| 2007/0265369 A1 | 11/2007 | Muratoglu et al. | |
| 2007/0267030 A1 * | 11/2007 | Muratoglu | A61L 27/16 128/899 |
| 2007/0275030 A1 | 11/2007 | Muratoglu et al. | |
| 2007/0293647 A1 | 12/2007 | McKellop et al. | |
| 2008/0039545 A1 | 2/2008 | Muratoglu et al. | |
| 2008/0067724 A1 | 3/2008 | Muratoglu et al. | |
| 2008/0090933 A1 | 4/2008 | Muratoglu et al. | |
| 2008/0090934 A1 | 4/2008 | Muratoglu et al. | |
| 2008/0119582 A1 | 5/2008 | Muratoglu et al. | |
| 2008/0133018 A1 | 6/2008 | Salovey et al. | |
| 2008/0133021 A1 | 6/2008 | Shen et al. | |
| 2008/0139137 A1 | 6/2008 | Guo et al. | |
| 2008/0140196 A1 | 6/2008 | Schroeder et al. | |
| 2008/0214692 A1 * | 9/2008 | Muratoglu | C08J 3/28 522/75 |
| 2008/0215142 A1 * | 9/2008 | Muratoglu | A61L 27/16 623/1.49 |
| 2008/0262120 A1 | 10/2008 | Muratoglu | |
| 2008/0274161 A1 | 11/2008 | Muratoglu et al. | |
| 2008/0293856 A1 | 11/2008 | Kumar et al. | |
| 2008/0318022 A1 | 12/2008 | James et al. | |
| 2008/0319137 A1 | 12/2008 | Rufner et al. | |
| 2009/0030524 A1 | 1/2009 | Schroeder et al. | |
| 2009/0105364 A1 | 4/2009 | Merrill et al. | |
| 2009/0118390 A1 | 5/2009 | Abt et al. | |

(56) References Cited

U.S. PATENT DOCUMENTS

| | | |
|---|---|---|
| 2009/0192610 A1 | 7/2009 | Case et al. |
| 2009/0265001 A1 | 10/2009 | Muratoglu et al. |
| 2009/0281624 A1 | 11/2009 | Conteduca et al. |
| 2010/0029858 A1 | 2/2010 | Rufner et al. |
| 2010/0082101 A1 | 4/2010 | Muratoglu et al. |
| 2010/0137481 A1 | 6/2010 | Shen et al. |
| 2010/0190882 A1* | 7/2010 | Muratoglu ............... C08F 10/02 522/129 |
| 2010/0331995 A1 | 12/2010 | Smelt et al. |
| 2011/0028600 A1 | 2/2011 | Rufner et al. |
| 2011/0306698 A1 | 12/2011 | Pletcher |
| 2012/0070600 A1 | 3/2012 | Muratoglu et al. |
| 2012/0157591 A1 | 6/2012 | Rufner et al. |
| 2014/0135415 A1 | 5/2014 | Abt et al. |
| 2014/0194934 A1 | 7/2014 | Rufner et al. |
| 2014/0194935 A1 | 7/2014 | Rufner et al. |
| 2014/0227548 A1* | 8/2014 | Myrick .................. C06B 45/30 428/570 |
| 2015/0151866 A1* | 6/2015 | Oral ........................ A61L 27/16 53/425 |
| 2016/0108184 A1 | 4/2016 | Rufner et al. |
| 2016/0145416 A1 | 5/2016 | Rufner et al. |
| 2016/0158976 A1 | 6/2016 | Pletcher |
| 2016/0280863 A1 | 9/2016 | Pletcher |
| 2017/0335074 A1 | 11/2017 | Abt et al. |

FOREIGN PATENT DOCUMENTS

| | | |
|---|---|---|
| AU | 2008236996 A1 | 10/2008 |
| AU | 2012203503 B2 | 5/2014 |
| CA | 2619937 A1 | 3/2007 |
| CA | 2669386 A1 | 8/2008 |
| CA | 2619502 C | 11/2012 |
| CS | 221403 B1 | 4/1983 |
| CZ | 221405 B1 | 2/1986 |
| EP | 0560279 A1 | 9/1993 |
| EP | 0727195 A2 | 8/1996 |
| EP | 0935446 A1 | 8/1999 |
| EP | 0995449 A1 | 4/2000 |
| EP | 0560279 B1 | 6/2000 |
| EP | 0727195 B1 | 8/2002 |
| EP | 141918 A1 | 5/2004 |
| EP | 1647242 A1 | 4/2006 |
| EP | 0935446 B1 | 2/2007 |
| EP | 1421918 B1 | 4/2008 |
| EP | 1647242 B1 | 5/2008 |
| EP | 1924614 A2 | 5/2008 |
| EP | 2046577 A1 | 4/2009 |
| EP | 2083981 A1 | 5/2009 |
| EP | 2150285 A2 | 2/2010 |
| EP | 2395048 A2 | 12/2011 |
| EP | 2150285 B1 | 2/2012 |
| EP | 2578248 A1 | 4/2013 |
| EP | 2277560 B1 | 10/2013 |
| EP | 2395048 B1 | 10/2013 |
| EP | 2172229 B1 | 7/2014 |
| GB | 2288399 A | 10/1995 |
| JP | 11239611 A | 9/1999 |
| JP | 2006515777 A | 6/2006 |
| JP | 2009504283 A | 2/2009 |
| JP | 2009504898 A | 2/2009 |
| JP | 2009504897 A | 5/2009 |
| JP | 2010523805 A | 7/2010 |
| JP | 2012143575 A | 8/2012 |
| JP | 2015097814 A | 5/2015 |
| JP | 5735443 B2 | 6/2015 |
| JP | 5969637 | 7/2016 |
| KR | 20090035724 A | 4/2009 |
| WO | WO-8900755 A1 | 1/1989 |
| WO | WO-9729793 A1 | 8/1997 |
| WO | WO-9801085 A1 | 1/1998 |
| WO | WO-9814223 A1 | 4/1998 |
| WO | WO-0049079 A1 | 8/2000 |
| WO | WO-0105337 A1 | 1/2001 |
| WO | WO-0180778 A1 | 11/2001 |
| WO | WO-03049930 A1 | 6/2003 |
| WO | WO-2004024204 A1 | 3/2004 |
| WO | WO-2004064618 A2 | 8/2004 |
| WO | WO-2004064618 A3 | 8/2004 |
| WO | WO-2004101009 A1 | 11/2004 |
| WO | WO-2005074619 A2 | 8/2005 |
| WO | WO-2006041969 A1 | 4/2006 |
| WO | WO-2007019874 A1 | 2/2007 |
| WO | WO-2007024684 A2 | 3/2007 |
| WO | WO-2007024686 A3 | 3/2007 |
| WO | WO-2007056561 A2 | 5/2007 |
| WO | WO-2007121167 A1 | 10/2007 |
| WO | WO-2008016174 A1 | 2/2008 |
| WO | WO-2008052574 A1 | 5/2008 |
| WO | WO-2008029047 A1 | 7/2008 |
| WO | WO-2008101073 A2 | 8/2008 |
| WO | WO-2008101134 A1 | 8/2008 |
| WO | WO-2008113388 A1 | 9/2008 |
| WO | WO-2008124825 A2 | 10/2008 |
| WO | WO-2008124825 A3 | 10/2008 |
| WO | WO-2009032909 A2 | 3/2009 |
| WO | WO-2009045658 A1 | 4/2009 |
| WO | WO-2009060043 A2 | 5/2009 |
| WO | WO-2009032909 A3 | 12/2009 |
| WO | WO-2010003688 A1 | 1/2010 |
| WO | WO-2010129514 A2 | 11/2010 |
| WO | WO-2010129514 A3 | 11/2010 |
| WO | WO-2012061499 A1 | 5/2012 |
| WO | 2013170005 | 11/2013 |
| WO | WO-2015050851 A1 | 4/2015 |
| WO | WO-2015138137 A1 | 9/2015 |
| WO | WO-2016090084 A1 | 6/2016 |
| WO | 2016153925 | 9/2016 |

OTHER PUBLICATIONS

"European Application Serial No. 12167581.3, Response filed Feb. 8, 2018 to Communication Pursuant to Article 94(3) EPC dated Sep. 28, 2017", 12 pgs.

"European Application Serial No. 12167580.5, Response filed Feb. 8, 2018 to Communication Pursuant to Article 94(3) EPC dated Sep. 28, 2017", 11 pgs.

"U.S. Appl. No. 14/157,687, Non Final Office Action dated Apr. 6, 2018", 25 pgs.

"U.S. Appl. No. 15/783,649, Response filed Apr. 17, 2018 to Non Final Office Action dated Jan. 17, 2018", 10 pgs.

"U.S. Appl. No. 15/073,042, Response filed Apr. 16, 2018 to Final Office Action dated Mar. 13, 2018", 17 pgs.

"Australian Application Serial No. 2015229947, Response filed May 17, 2018 to First Examination Report dated Feb. 14, 2018", 23 pgs.

"U.S. Appl. No. 15/783,649, Final Office Action dated Jun. 4, 2018", 14 pgs.

"U.S. Appl. No. 15/073,042, Final Office Action dated Mar. 13, 2018", 15 pgs.

"Australian Application Serial No. 2015229947, First Examination Report dated Feb. 14, 2018", 3 pgs.

"U.S. Appl. No. 14/157,687, Response filed Mar. 8, 2018 to Final Office Action dated Nov. 30, 2017", 20 pgs.

"International Application Serial No. PCT/US2016/022896, International Preliminary Report on Patentability dated Oct. 5, 2017", 9 pgs.

"U.S. Appl. No. 15/783,649, Preliminary Amendment filed Oct. 15, 2017", 5 pgs.

"U.S. Appl. No. 14/983,006, Response filed Oct. 25, 2017 to Final Office Action dated Jul. 25, 2017", 7 pgs.

U.S. Appl. No. 12/100,894, filed Ap. 10, 2008, Antioxidant Stabilized Crosslinked Ultra-High Molecular Weight Polyethylene for Medical Device Applications.

U.S. Appl. No. 14/983,006, filed Dec. 29, 2015, Antioxidant Stabilized Crosslinked Ultra-High Molecular Weight Polyethylene for Medical Device Applications.

U.S. Appl. No. 14/157,687, filed Jan. 17, 2014, Ultra High Molecular Weight Polyethylene Articles and Methods of Forming Ultra High Molecular Weight Polyethylene Articles.

(56) References Cited

OTHER PUBLICATIONS

U.S. Appl. No. 14/978,598, filed Dec. 22, 2015, Antioxidant Stabilized Crosslinked Ultra High Molecular Weight Polyethylene for Medical Device Applications.
U.S. Appl. No. 15/073,042, filed Mar. 17, 2016, Melt-Stabilized Ultra High Molecular Weight Antioxidant.
"U.S. Appl. No. 15/673,903, Non Final Office Action dated Oct. 10, 2018", 15 pgs.
"U.S. Appl. No. 15/783,649, Response filed Sep. 4, 2018 to Final Office Action dated Jun. 4, 2018", 10 pgs.
"European Application Serial No. 12167580.5, Communication Pursuant to Article 94(3) EPC dated Aug. 10,2018", 7 pgs.
"European Application Serial No. 12167581.3, Communication Pursuant to Article 94(3) EPC dated Aug. 10, 2018", 9 pgs.
"European Application Serial No. 14173530.8, Summons to Attend Oral Proceedings mailed Aug. 14, 2018", 6 pgs.
"Gamma- & Betastrahlen", BGS w/English Translation, [Online]. [Accessed Sep. 27, 2016]. Retrieved from the Internet: <URL: http://de.bgs.eu/wie-funktioniert-es/gamma-betastrahlen/>, 8 pgs.
"Gray (unit)", [Online]. Retrieved from the Internet: <URL: http://en.wikipedia.org/wik.i/Megagray>, (Accessed Nov. 28, 2013), 5 pgs.
"GUR® (UHMWPE) with vitamin E for orthopedic implants", Ticona—News Release, (Oct. 29, 2007), 2 pgs.
"Radiation crosslinking refines polymers for more efficient use of plastics (Translation of Strahlenvernetzung veredelt Polymere fur den effizienteren Kunststoffeinsatz)", Ingenieur.de, [Online]. [Accessed Sep. 27, 2016. Retrieved from the Internet: <URL: https://www.ingenieur.de/technik/fachbereiche/verfahrenstechnik/strahlenvernetzung-veredelt-polymere-fuer-effizienteren-kunststoffeinsatz/>, 7 pgs.
Ingo, John, "", Statement of Dr-Ing. Ingo John from May 9, 2017, 1 pg.
Knight III, John C., "", Declaration, (Oct. 5, 2016), 13 pgs.
Kurtz, Steven, "The UMWPE Handbook", Ultra-High Molecular Weight Polyethylene in Total Joint Replacement—pp. 22-23, 253, (2004), 5 pgs.
Labrie, J.P., et al., "AECL Impela ELECfRON Beam Industrial Irradiators", Nuclear Instruments and Methods of Physics Research vol. B40/41, (1989), 1153-1157.
Steven, Kurtz, "", Declaration from May 19, 2017, 3 pgs.
Werner, Schneider-Storrer, "", Declaration, (Oct. 5, 2016), 3 pgs.
"U.S. Appl. No. 15/073,042, Response filed Aug. 8, 2018 to Non Final Office Action dated Jun. 27, 2018", 17 pgs.
"U.S. Appl. No. 14/983,006, Notice of Allowance dated Nov. 15, 2017", 7 pgs.
"European Application Serial No. 16203066.2, Response filed Nov. 27, 2017 to Extended European Search Report dated Apr. 13, 2017", 17 pgs.
"U.S. Appl. No. 14/157,687, Final Office Action dated Nov. 30, 2017", 27 pgs.
"European Application Serial No. 12167580.5, Communication Pursuant to Article 94(3) EPC dated Sep. 28, 2017", 4 pgs.
"European Application Serial No. 12167581.3, Communication Pursuant to Article 94(3) EPC dated Sep. 28, 2017", 8 pgs.
"European Application Serial No. 12154330.0, Response filed Oct. 18, 2016 to Communication Pursuant to Article 94(3) EPC dated Apr. 8, 2016", 6 pgs.
"U.S. Appl. No. 14/157,687, Final Office Action dated Dec. 1, 2016", 22 pgs.
"U.S. Appl. No. 14/983,006, Response filed Mar. 16, 2017 to Final Office Action dated Dec. 22, 2016", 10 pgs.
"U.S. Appl. No. 14/157,687, Non Final Office Action dated May 5, 2017", 23 pgs.
"Application Serial No. 15708669.5, Response filed May 25, 2017 to action dated Nov. 15, 2016", 20 pgs.
"U.S. Appl. No. 15/073,042, Response filed Jul. 20, 2017 to Final Office Action dated Jun. 2, 2017", 15 pgs.
"U.S. Appl. No. 14/978,598, Notice of Allowance dated Aug. 4, 2017", 8 pgs.
"U.S. Appl. No. 14/983,006, Response filed Jun. 30, 2017 to Non Final Office Action dated Mar. 31, 2017", 13 pgs.
"International Application Serial No. PCT/US2015/017741, International Preliminary Report on Patentability dated Sep. 22, 2016", 8 pgs.
"European Application Serial No. 16203066.2, Extended European Search Report dated Apr. 13, 2017", 9 pgs.
"U.S. Appl. No. 15/673,903, Preliminary Amendment filed Aug. 11, 2017", 6 pgs.
"U.S. Appl. No. 14/157,687, Response filed Aug. 4, 2017 to Non Final Office Action dated May 5, 2017", 20 pgs.
"U.S. Appl. No. 14/978,598, Response filed Jul. 26, 2017 to Final Office Action dated Jun. 1, 2017", 6 pgs.
"U.S. Appl. No. 14/983,006, Final Office Action dated Jul. 25, 2017", 7 pgs.
"U.S. Appl. No. 14/978,598, Final Office Action dated Jun. 1, 2017", 8 pgs.
"U.S. Appl. No. 15/073,042, Response filed May 24, 2017 to Non Final Office Action dated Apr. 11, 2017", 15 pgs.
"U.S. Appl. No. 15/073,042, Non Final Office Action dated Apr. 11, 2017", 16 pgs.
"U.S. Appl. No. 14/978,598, Response filed Mar. 31, 2017 to Non Final Office action dated Jan. 18, 2017", 16 pgs.
"U.S. Appl. No. 14/983,006, Final Office Action dated Dec. 22, 2016", 12 pgs.
"U.S. Appl. No. 14/978,598, Response filed Dec. 1, 2016 to Non Final Office Action dated Sep. 1, 2016", 19 pgs.
"U.S. Appl. No. 14/983,006, Supplemental Preliminary Amendment filed Aug. 8, 2016", 62 pgs.
"U.S. Appl. No. 14/983,006, Response filed Dec. 1, 2016 to Non Final Office Action dated Sep. 1, 2016", 16 pgs.
"U.S. Appl. No. 14/978,598, Non Final Office Action dated Jan. 18, 2017", 13 pgs.
"U.S. Appl. No. 14/157,687, Response filed Feb. 13, 2017 to Final Office Action dated Dec. 1, 2016", 14 pgs.
"U.S. Appl. No. 14/983,006, Non Final Office Action dated Mar. 31, 2017", 15 pgs.
"U.S. Appl. No. 15/073,042, Final Office Action dated Jun. 2, 2017", 13 pgs.
Bauer, I., "Synthesis of New Organic Phosphites Containing Sterically Hindered Piperidine Groups. Phosphorus, Sulfur, and Silicon and the Related Elements", vol. 28, (1997), 79-103 pgs.
"Australian Application Serial No. 2015229947, Subsequent Examiners Report dated Jun. 14, 2018", 4 pgs.
"U.S. Appl. No. 15/073,042, Non Final Office Action dated Jun. 27, 2018", 16 pgs.
U.S. Appl. No. 14/157,687, Response filed Jul. 5, 2018 to Non Final Office Action dated Apr. 6, 2018, 21 pgs.
"U.S. Appl. No. 11/465,743, Advisory Action dated Jul. 16, 2008", 5pgs.
"U.S. Appl. No. 11/465,743, Advisory Action dated Aug. 6, 2008", 6 pgs.
"U.S. Appl. No. 11/465,743, Advisory Action dated Aug. 24, 2009", 6 pgs.
"U.S. Appl. No. 11/465,743, Amended Appeal Brief filed Mar. 10, 2010", 42 pgs.
"U.S. Appl. No. 11/465,743, Amended Appeal Brief filed Dec. 15, 2009", 41 pgs.
"U.S. Appl. No. 11/465,743, Appeal Brief filed Nov. 15, 2009", 41 pgs.
"U.S. Appl. No. 11/465,743, Examiner Interview Summary dated Apr. 29, 2009", 4 pgs.
"U.S. Appl. No. 11/465,743, Examiner Interview Summary dated Sep. 23, 2010", 2 pgs.
"U.S. Appl. No. 11/465,743, Examiner Interview Summary dated Sep. 29, 2010", 2 pgs.
"U.S. Appl. No. 11/465,743, Examiner Interview Summary dated Oct. 3, 2008", 3 pgs.
"U.S. Appl. No. 11/465,743, Final Office Action dated May 1, 2008", 9 pgs.
"U.S. Appl. No. 11/465,743, Final Office Action dated Jun. 16, 2009", 11 pgs.

(56) References Cited

OTHER PUBLICATIONS

"U.S. Appl. No. 11/465,743, Non Final Office Action dated Sep. 28, 2007", 7 pgs.
"U.S. Appl. No. 11/465,743, Non Final Office Action dated Dec. 15, 2008", 12 pgs.
"U.S. Appl. No. 11/465,743, Notice of Allowance dated May 26, 2010", 6 pgs.
"U.S. Appl. No. 11/465,743, Notice of Allowance dated Sep. 3, 2010", 7 pgs.
"U.S. Appl. No. 11/465,743, Response filed Jan. 17, 2008 to Non Final Office Action dated Sep. 28, 2007", 13 pgs.
"U.S. Appl. No. 11/465,743, Response filed Mar. 16, 2009 to Non Final Office Action dated Dec. 15, 2008", 11 pgs.
"U.S. Appl. No. 11/465,743, Response filed Jul. 1, 2008 to Final Office Action dated May 1, 2008", 8 pgs.
"U.S. Appl. No. 11/465,743, Response filed Jul. 22, 2008 to Advisory Action dated Jul. 16, 2008", 6 pgs.
"U.S. Appl. No. 11/465,743, Response filed Jul. 29, 2009 to Final Office Action dated Jun. 16, 2009", 15 pgs.
"U.S. Appl. No. 11/465,743, Response filed Oct. 31, 2008 to Advisory Action dated Aug. 6, 2008", 15 pgs.
"U.S. Appl. No. 11/465,743, Supplemental Notice of Allowability dated Jul. 14, 2010", 2 pgs.
"U.S. Appl. No. 11/465,743, Supplemental Notice of Allowability dated Sep. 23, 2010", 4 pgs.
"U.S. Appl. No. 11/465,743, Supplemental Notice of Allowability dated Sep 29, 2010", 4 pgs.
"U.S. Appl. No. 11/465,743, Supplemental Response filed Apr. 20, 2009 to Non Final Office Action dated Dec. 15, 2008", 10 pgs.
"U.S. Appl. No. 12/100,894, Examiner Interview Summary dated Dec. 2, 2009", 3 pgs.
"U.S. Appl. No. 12/100,894, Non Final Office Action dated Apr. 14, 2009", 16 pgs.
"U.S. Appl. No. 12/100,894, Response filed Mar. 31, 2009 to Restriction Requirement dated Mar. 2, 2009", 2 pgs.
"U.S. Appl. No. 12/100,894, Restriction Requirement dated Mar. 2, 2009", 7 pgs.
"U.S. Appl. No. 12/262,531, Final Office Action dated Jan. 14, 2010", 11 pgs.
"U.S. Appl. No. 12/262,531, Non Final Office Action dated Jun. 17, 2010", 16 pgs.
"U.S. Appl. No. 12/262,531, Non Final Office Action dated Jun. 25, 2009", 7 pgs.
"U.S. Appl. No. 12/262,531, Notice of Allowance dated Oct. 28, 2010", 6 pgs.
"U.S. Appl. No. 12/262,531, Preliminary Amendment filed Oct. 31, 2008", 6 pgs.
"U.S. Appl. No. 12/262,531, Response filed Apr. 28, 2010 to Final Office Action dated Jan. 14, 2010", 15 pgs
"U.S. Appl. No. 12/262,531, Response filed Sep. 17, 2010 to Non Final Office Action dated Jun. 17, 2010", 4 pgs.
"U.S. Appl. No. 12/262,531, Response filed Sep. 23, 2009 to Non Final Office Action dated Jun. 25, 2009", 10 pgs.
"U.S. Appl. No. 12/262,531, Supplemental Notice of Allowability dated Nov. 23, 2010", 4 pgs.
"U.S. Appl. No. 12/464,235, Final Office Action dated Aug. 19, 2010", 11 pgs.
"U.S. Appl. No. 12/464,235, Non Final Office Action dated Mar. 2, 2010", 7 pgs.
"U.S. Appl. No. 12/464,235, Non Final Office Action dated Dec. 23, 2010", 10 pgs.
"U.S. Appl. No. 12/579,094, Examiner Interview Summary dated Jan. 6, 2012", 1 pg.
"U.S. Appl. No. 12/579,094, Final Office Action dated Oct. 13, 2010", 14 pgs.
"U.S. Appl. No. 12/579,094, Non Final Office Action dated May 18, 2010", 19 pgs.
"U.S. Appl. No. 12/579,094, Notice of Allowance dated Jan. 6, 2012", 8 pgs.
"U.S. Appl. No. 12/579,094, Preliminary Amendment filed Oct. 14, 2009", 11 pgs.
"U.S. Appl. No. 12/579,094, Response filed Jan. 27, 2012 to Notice of Allowance dated Jan. 6, 2012", 5 pgs.
"U.S. Appl. No. 12/579,094, Response filed Jan. 31, 2012 to 312 Amendment dated Jan. 27, 2012", 2 pgs.
"U.S. Appl. No. 12/579,094, Response filed Apr. 7, 2010 to Restriction Requirement dated Mar. 9, 2010", 9 pgs.
"U.S. Appl. No. 12/579,094, Response filed Apr. 12, 2011 to Final Office Action dated Oct. 13, 2010", 45 pgs.
"U.S. Appl. No. 12/579,094, Response filed Sep. 20, 2010 to Non Final Office Action dated May 18, 2010", 30 pgs.
"U.S. Appl. No. 12/579,094, Restriction Requirement dated Mar. 9, 2010", 7 pgs.
"U.S. Appl. No. 12/813,401, Non Final Office Action dated Aug. 14, 2012", 10 pgs.
"U.S. Appl. No. 12/813,401, Non Final Office Action dated Aug. 25, 2011", 9 pgs.
"U.S. Appl. No. 12/813,401, Notice of Allowance dated Apr. 16, 2012", 7 pgs.
"U.S. Appl. No. 12/813,401, Notice of Allowance dated Nov. 21, 2012", 5 pgs.
"U.S. Appl. No. 12/813,401, Response filed Jan. 26, 2012 to Non Final Office Action dated Aug. 26, 2011", 7 pgs.
"U.S. Appl. No. 12/813,401, Response filed Oct. 26, 2012 to Non Final Office Action dated Aug. 14, 2012", 8 pgs.
"U.S. Appl. No. 12/847,741, Examiner Interview Summary dated Aug. 6, 2013", 4 pgs.
"U.S. Appl. No. 12/847,741, Final Office Action dated Jun. 27, 2012", 7 pgs.
"U.S. Appl. No. 12/847,741, Non Final Office Action dated Feb. 24, 2012", 11 pgs.
"U.S. Appl. No. 12/847,741, Non Final Office Action dated May 9, 2013", 11 pgs.
"U.S. Appl. No. 12/847,741, Notice of Allowance dated Oct. 17, 2013", 11 pgs.
"U.S. Appl. No. 12/847,741, Preliminary Amendment filed Oct. 18, 2010", 5 pgs.
"U.S. Appl. No. 12/847,741, Response filed May 23, 2012 to Non Final Office Action dated Feb. 24, 2012", 10 pgs.
"U.S. Appl. No. 12/847,741, Response filed Sep. 3, 2013 to Non Final Office Action dated May 9, 2013", 18 pgs.
"U.S. Appl. No. 12/847,741, Response filed Sep. 26, 2012 to Final Office Action dated Jun. 27, 2012", 14 pgs.
"U.S. Appl. No. 12/847,741, Second Preliminary Amendment filed Feb. 21, 2012", 4 pgs.
"U.S. Appl. No. 12/942,703, Applicant's Summary of Examiner Interview filed Feb. 17, 2012", 3 pgs.
"U.S. Appl. No. 12/942,703, Final Office Action dated Jan. 7, 2013", 8 pgs.
"U.S. Appl. No. 12/942,703, Final Office Action dated Mar. 16, 2012", 14 pgs.
"U.S. Appl. No. 12/942,703, Non Final Office Action dated Aug. 2, 2011", 17 pgs.
"U.S. Appl. No. 12/942,703, Non Final Office Action dated Aug. 23, 2012", 14 pgs.
"U.S. Appl. No. 12/942,703, Notice of Allowance dated Mar. 1, 2013", 8 pgs.
"U.S. Appl. No. 12/942,703, Response filed Jan. 3, 2012 to Non Final Office Action dated Aug. 2, 2011", 34 pgs.
"U.S. Appl. No. 12/942,703, Response filed Feb. 13, 2013 to Final Office Action dated Jan. 7, 2013", 7 pgs.
"U.S. Appl. No. 12/942,703, Response filed Jul. 16, 2012 to Final Office Action dated Mar. 16, 2012", 14 pgs.
"U.S. Appl. No. 12/942,703, Response filed Nov. 30, 2012 to Non Final Office Action dated Aug. 23, 2012", 15 pgs.
"U.S. Appl. No. 12/943,160, Applicant's Summary of Examiner Interview filed Feb. 17, 2012", 2 pgs.
"U.S. Appl. No. 12/943,160, Examiner Interview Summary dated Feb. 3, 2012", 2 pgs.
"U.S. Appl. No. 12/943,160, Examiner Interview Summary dated Aug. 15, 2013", 3 pgs.

(56) References Cited

OTHER PUBLICATIONS

"U.S. Appl. No. 12/943,160, Final Office Action dated Sep. 28, 2012", 14 pgs.
"U.S. Appl. No. 12/943,160, Non Final Office Action dated Mar. 16, 2012", 11 pgs.
"U.S. Appl. No. 12/943,160, Non Final Office Action dated Jun. 25, 2013", 9 pgs.
"U.S. Appl. No. 12/943,160, Non Final Office Action dated Aug. 12, 2011", 8 pgs.
"U.S. Appl. No. 12/943,160, Notice of Allowance dated Oct. 17, 2013", 9 pgs.
"U.S. Appl. No. 12/943,160, Response filed Jan. 11, 2012 to Non Final Office Action dated Aug. 12, 2011", 13 pgs.
"U.S. Appl. No. 12/943,160, Response filed Jul. 16, 2012 to Non Final Office Action dated Mar. 16, 2012", 13 pgs.
"U.S. Appl. No. 12/943,160, Response filed Sep. 18, 2013 to Non Final Office Action dated Jun. 26, 2013", 8 pgs.
"U.S. Appl. No. 12/943,160, Response filed Nov. 20, 2012 to Non Final Office Action dated Sep. 28, 2012", 10 pgs.
"U.S. Appl. No. 12/967,581, Examiner Interview Summary dated Jan. 23, 2012", 2 pgs.
"U.S. Appl. No. 12/967,581, Notice of Allowance dated Feb. 7, 2012", 10 pgs.
"U.S. Appl. No. 12/967,581, Preliminary Amendment filed Jan. 19, 2012", 7 pgs.
"U.S. Appl. No. 12/967,581, Preliminary Amendment filed Jan. 27, 2012", 4 pgs.
"U.S. Appl. No. 12/967,581, Preliminary Amendment filed Feb. 18, 2011", 5 pgs.
"U.S. Appl. No. 12/967,581, Preliminary Amendment filed Dec. 14, 2010", 7 pgs.
"U.S. Appl. No. 13/403,040, Advisory Action dated Jan. 28, 2013", 6 pgs.
"U.S. Appl. No. 13/403,040, Examiner Interview Summary dated Jan. 30, 2013", 3 pgs.
"U.S. Appl. No. 13/403,040, Final Office Action dated Nov. 19, 2012", 14 pgs.
"U.S. Appl. No. 13/403,040, Non Final Office Action dated Jul. 1, 2013", 8 pgs.
"U.S. Appl. No. 13/403,040, Non Final Office Action dated Jul. 16, 2012", 14 pgs.
"U.S. Appl. No. 13/403,040, Notice of Allowance dated Oct. 16, 2013", 10 pgs.
"U.S. Appl. No. 13/403,040, PTO Response to 312 Amendment dated dated Feb. 6, 2014", 2 pgs.
"U.S. Appl. No. 13/403,040, Response filed Jan. 22, 2013 to Final Office Action dated Nov. 19, 2012", 13 pgs.
"U.S. Appl. No. 13/403,040, Response filed Feb. 18, 2013 to Advisory Action dated Jan. 28, 2013", 13 pgs.
"U.S. Appl. No. 13/403,040, Response filed Sep. 3, 2013 to Non Final Office Action dated Jul. 1, 2013", 13 pgs.
"U.S. Appl. No. 13/403,040, Response filed Oct. 15, 2012 to Non Final Office Action dated Jul. 16, 2012", 15 pgs.
"U.S. Appl. No. 14/157,687, Non Final Office Action dated Oct. 8, 2015", 20 pgs.
"U.S. Appl. No. 14/157,687, Preliminary Amendment dated Jan. 22, 2014", 6 pgs.
"U.S. Appl. No. 14/157,687, Response filed Jan. 6, 2016 to Non Final Office Action dated Oct. 8, 2015", 15 pgs.
"U.S. Appl. No. 14/157,695, Final Office Action dated Sep. 2, 2015", 13 pgs.
"U.S. Appl. No. 14/157,695, Non Final Office Action dated May 8, 2015", 16 pgs.
"U.S. Appl. No. 14/157,695, Notice of Allowance dated Sep. 23, 2015", 9 pgs.
"U.S. Appl. No. 14/157,695, Preliminary Amendment filed Jan. 29, 2014", 21 pgs.
"U.S. Appl. No. 14/157,695, PTO Response to Rule 312 Communication dated Feb. 9, 2016", 2 pgs.
"U.S. Appl. No. 14/157,695, Response filed Aug. 7, 2015 to Non Final Office Action dated May 8, 2015", 18 pgs.
"U.S. Appl. No. 14/157,695, Response filed Sep. 10, 2015 to Final Office Action dated Sep. 2, 2015", 12 pgs.
"U.S. Appl. No. 14/157,708, Non Final Office Action dated Jun. 10, 2015", 15 pgs.
"U.S. Appl. No. 14/157,708, Notice of Allowance dated Oct. 14, 2015", 9 pgs.
"U.S. Appl. No. 14/157,708, Preliminary Amendment dated Jan. 22, 2014", 18 pgs.
"U.S. Appl. No. 14/157,708, Response filed Sep. 10, 2015 to Non Final Office Action dated Jun. 10, 2015", 17 pgs.
"U.S. Appl. No. 14/978,598, Non Final Office Action dated Sep. 1, 2016", 11 pgs.
"U.S. Appl. No. 14/978,598, Preliminary Amendment filed Dec. 28, 2015", 5 pgs.
"U.S. Appl. No. 14/983,006, Non Final Office Action dated Sep. 1, 2016", 13 pgs.
"U.S. Appl. No. 14/983,006, Preliminary Amendment filed Dec. 30, 2015", 5 pgs.
"U.S. Appl. No. 15/026,153 Preliminary Amendment filed Mar. 30, 2016", 10 pgs.
"Australian Application Serial No. 2005335669, Office Action dated Mar. 21, 2011", 3 pgs.
"Australian Application Serial No. 2005335669, Response filed Feb. 1, 2012 to Office Action dated Mar. 21, 2011", 15 pgs.
"Australian Application Serial No. 2008236996, Office Action dated Jun. 19, 2012", 3 pgs.
"Australian Application Serial No. 2012203503, First Examiner Report dated May 7, 2013", 4 pgs.
"Australian Application Serial No. 2012203503, Response filed Sep. 24, 2013 to First Examiner Report dated May 7, 2013", 17 pgs.
"Australian Application Serial No. 2013200780, First Examiner Report dated Jan. 3, 2014", 3 pgs.
"Australian Application Serial No. 2013200780, Response filed Apr. 9, 2014 to First Examiner Report dated Jan. 3, 2014", 28 pgs.
"Australian Application Serial No. 2013200780, Response filed Aug. 5, 2014 to Office Action dated May 22, 2014", 3 pgs.
"Australian Application Serial No. 2013200780, Subsequent Examiners Report dated May 22, 2014", 3 pgs.
"Australian Application Serial No. 2013200780, Subsequent Examiners Report dated Sep. 3, 2014", 3 pgs.
"Australian Application Serial No. 2014201581, First Examiner Report dated May 8, 2015", 3 pgs.
"Australian Application Serial No. 2014201581, Response filed Oct. 9, 2015 to First Examiner Report dated May 8, 2015", 18 pgs.
"Australian Application Serial No. 2014274546, First Examiner Report dated Feb. 26, 2016", 3 pgs.
"Australian Application Serial No. 2014274546, Response filed Apr. 15, 2016 to First Examiner Report dated Feb. 26, 2016", 17 pgs.
"Biomet Orthopedics", Brochure E-POLY HSLPE (EXH2O), (2007), 23 pgs.
"Canadian Application No. 2,619,502, Office Action dated Nov. 4, 2011", 4 pgs.
"Canadian Application No. 2,619,502, Response filed Jan. 30, 2012 to Office Action dated Nov. 4, 2011", 6 pgs.
"Canadian Application No. 2,619,502, Response filed Sep. 2, 2011 to Office Action dated Nov. 4, 2011", 17 pgs.
"Canadian Application Serial 2,678,459, Office Action dated Jul. 23, 2015", 4 pgs.
"Canadian Application Serial No. 2,678,459, Office Action dated Apr. 11, 2013", 4 pgs.
"Canadian Application Serial No. 2,678,459, Office Action dated Nov. 21, 2014", 2 pgs.
"Canadian Application Serial No. 2,678,459, Response filed Mar. 25, 2015 to Office Action dated Nov. 21, 2014", 57 pgs.
"Canadian Application Serial No. 2,678,459, Response filed Oct. 11, 2013 to Office Action dated Apr. 11, 2013", 45 pgs.
"Canadian Application Serial No. 2,788,687, Office Action dated Jun. 4, 2014", 2 pgs.
"Canadian Application Serial No. 2,788,687, Office Action dated Jul. 10, 2013", 4 pgs.

(56) References Cited

OTHER PUBLICATIONS

"Canadian Application Serial No. 2,788,687, Office Action dated Aug. 27, 2015", 4 pgs.
"Canadian Application Serial No. 2,788,687, Response filed Jul. 10, 2013 to Office Action dated Jan. 10, 2014", 25 pgs.
"E-POLY HXLPE Brochure", Biomet Orthopedics, (2007), 23 pgs.
"European Application Serial No. 05777319.4, Office Action dated Jun. 10, 2009", 4 pgs.
"European Application Serial No. 05777319.4, Office Action dated Jul. 28, 2010", 1 pg.
"European Application Serial No. 05777319.4, Office Action dated Sep. 15, 2008", 1 pg.
"European Application Serial No. 05777319.4, Response filed Jan. 20, 2009 to Office Action dated Sep. 15, 2008", 7 pgs.
"European Application Serial No. 05777319.4, Response filed Oct. 8, 2009 to Office Action dated Jun. 10, 2009", 9 pgs.
"European Application Serial No. 08745507.7, Office Action dated Jan. 12, 2010", 2 pgs.
"European Application Serial No. 08745507.7, Office Action dated May 10, 2010", 3 pgs.
"European Application Serial No. 08745507.7, Office Action dated Jul. 20, 2011", 4 pgs.
"European Application Serial No. 08745507.7, Office Action dated Dec. 12, 2012", 1 pg.
"European Application Serial No. 08745507.7, Response filed Feb. 16, 2010 to Office Action dated Jan. 12, 2010", 5 pgs.
"European Application Serial No. 08745507.7, Response filed Sep. 20, 2010 to Office Action dated May 10, 2010", 3 pgs.
"European Application Serial No. 08745507.7, Response filed Nov. 21, 2011 to Office Action dated Jul. 20, 2011", 3 pgs.
"European Application Serial No. 09013154.1, European Examination Notification dated Jan. 4, 2013", 4 pgs.
"European Application Serial No. 09013154.1, European Search Report dated Feb. 23, 2010", 6 pgs.
"European Application Serial No. 09013154.1, Office Action dated Sep. 14, 2011", 4 pgs.
"European Application Serial No. 09013154.1, Office Action dated Oct. 21, 2010", 1 pg.
"European Application Serial No. 09013154.1, Response filed Jan. 26, 2012 to Office Action dated Sep. 14, 2011", 7 pgs.
"European Application Serial No. 09013154.1, Response filed Mar. 21, 2011 Office Action dated Oct. 21, 2010", 22 pgs.
"European Application Serial No. 09013154.1, Response filed May 14, 2013 to Examination Notification Art. 94(3) dated Jan. 4, 2013", 9 pgs.
"European Application Serial No. 10012579.8, European Search Report dated Feb. 23, 2010", 3 pgs.
"European Application Serial No. 10012579.8, Extended Search Report and Written Opinion dated Dec. 9, 2010", 8 pgs.
"European Application Serial No. 10012579.8, Extended Search Report and Written Opinion dated Dec. 16, 2010", 8 pgs.
"European Application Serial No. 10012579.8, Notice of Opposition dated Aug. 18, 2014", 1 pg.
"European Application Serial No. 10012579.8, Office Action dated Jan. 31, 2011", 2 pgs.
"European Application Serial No. 10012579.8, Office Action dated Apr. 23, 2012", 4 pgs.
"European Application Serial No. 10012579.8, Office Action dated Sep. 14, 2011", 4 pgs.
"European Application Serial No. 10012579.8, Office Action dared Sep. 18, 2012", 4 pgs.
"European Application Serial No. 10012579.8, Response filed Jan. 26, 2012 to Office Action dated Sep. 14, 2011", 11 pgs.
"European Application Serial No. 10012579.8, Response filed Jan. 28, 2013 to Examination Notification Art. 94(3) dated Sep. 18, 2012", 9 pgs.
"European Application Serial No. 10012579.8, Response filed Jul. 3, 2012 to Office Action dated Apr. 23, 2012", 15 pgs.
"European Application Serial No. 10012579.8, Response filed Jul. 26, 2011 to Office Action dated Jan. 31, 2011", 29 pgs.
"European Application Serial No. 10012589.7, European Search Report dated Feb. 23, 2010", 6 pgs.
"European Application Serial No. 10012589.7, European Search Report dated Dec. 9, 2010", 7 pgs.
"European Application Serial No. 10012589.7, Extended Search Report and Written Opinion dated Dec. 16, 2010", 8 pgs.
"European Application Serial No. 10012589.7, Office Action dated Jan. 31, 2011", 2 pgs.
"European Application Serial No. 10012589.7, Office Action dated Feb. 3, 2010", 1 pg.
"European Application Serial No. 10012589.7, Office Action dated Mar. 27, 2012", 4 pgs.
"European Application Serial No. 10012589.7, Office Action dated Dec. 16, 2010", 1 pg.
"European Application Serial No. 10012589.7, Response filed Jan. 13, 2012", 8 pgs.
"European Application Serial No. 10012589.7, Response filed Feb. 13, 2012 to Office Action dated Dec. 2, 2011", 7 pgs.
"European Application Serial No. 10012589.7, Response filed Jul. 25, 2011 to Office Action dated Jan. 32, 2011", 9 pgs.
"European Application Serial No. 11169368.5, European Search Report dated Apr. 23, 2012", 5 pgs.
"European Application Serial No. 11169368.5, Response filed Nov. 1, 2012 to European Search Report dated Apr. 23, 2012", 9 pgs.
"European Application Serial No. 12154330.0, Communication Pursuant to Article 94(3) EPC dated Apr. 8, 2016", 7 pgs.
"European Application Serial No. 12154330.0, European Search Report dated Jul. 18, 2012", 15 pgs.
"European Application Serial No. 12154330.0, Examination Notification Art. 94(3) dated Mar. 10, 2015", 10 pgs.
"European Application Serial No. 12154330.0, Examination Notification Art. 94(3) dated May 30, 2013", 11 pgs.
"European Application Serial No. 12154330.0, Examination Notification Art. 94(3) dated Aug. 7, 2013", 9 pgs.
"European Application Serial No. 12154330.0, Response filed Feb. 15, 2013 to Extended European Search Report dated Jul. 18, 2012", 18 pgs.
"European Application Serial No. 12154330.0, Response filed Jul. 3, 2013 to Examination Notification Art. 94(3) dated May 30, 2013", 8 pgs.
"European Application Serial No. 12154330.0, Response filed Jul. 20, 2015 to Examination Notification Art. 94(3) dared Mar. 10, 2015", 14 pgs.
"European Application Serial No. 12154330.0, Response filed Dec. 17, 2013 to Examination Notification Art. 94(3) dated Aug. 7, 2013", 14 pgs.
"European Application Serial No. 12167580.5, Examination Notification Art. 94(3) dated Mar. 26, 2015", 3 pgs.
"European Application Serial No. 12167580.5, Extended European Search Report dated Feb. 4, 2013", 15 pgs.
"European Application Serial No. 12167580.5, Response filed Aug. 5, 2015 Examination Notification Art, 94(3) dated Mar. 26, 2015", 9 pgs.
"European Application Serial No. 12167580.5, Response filed Sep. 5, 2013 to Extended European Search Report dated Feb. 4, 2013", 18 pgs.
"European Application Serial No. 12167581.3, European Search Report dated Mar. 13, 2013", 13 pgs.
"European Application Serial No. 12167581.3, Examination Notification Art. 94(3) dated Mar. 26, 2015", 4 pgs.
"European Application Serial No. 12167581.3, Response filed Aug. 5, 2015 to Examination Notification Art. 94(3) dated Mar. 26, 2015", 14 pgs.
"European Application Serial No. 12167581.3, Response filed Oct. 10, 2013 to Extended European Search Report dated Mar. 13, 2013", 16 pgs.
"European Application Serial No. 14173530.8, Extended European Search Report dated Sep. 24, 2014", 8 pgs.
"International Application Serial No. PCT/EP2005/008967, International Preliminary Report on Patentability dated Feb. 20, 2008", 7 pgs.

(56) References Cited

OTHER PUBLICATIONS

"International Application Serial No. PCT/EP2005/008967, International Search Report and Written Opinion dated Jun. 21, 2006", 10 pgs.
"International Application Serial No. PCT/EP2009/008250, International Search Report dated Jan. 21, 2010", 3 pgs.
"International Application Serial No. PCT/EP2009/008250, Written Opinion dated Jan. 21, 2010", 5 pgs.
"International Application Serial No. PCT/US2008/059909, International Preliminary Report on Patentability dated Nov. 10, 2009", 8 pgs.
"International Application Serial No. PCT/US2008/059909, International Search Report and Written Opinion dated Sep. 14, 2009", 14 pgs.
"International Application Serial No. PCT/US2008/086817, International Search Report dated Sep. 14, 2009", 3 pgs.
"International Application Serial No. PCT/US2008/086817, Written Opinion dated Sep. 14, 2009", 7 pgs.
"International Application Serial No. PCT/US2009/032412, International Search Report and Written Opinion dated Mar. 25, 2010", 9 pgs.
"International Application Serial No. PCT/US2014/058241, International Preliminary Report on Patentability dated Apr. 14, 2016", 5 pgs.
"International Application Serial No. PCT/US2014/058241, International Search Report dated Nov. 27, 2014", 3 pgs.
"International Application Serial No. PCT/US2014/058241, Written Opinion dated Nov. 27, 2014", 3 pgs.
"International Application Serial No. PCT/US2015/017741, International Search Report dated Aug. 7, 2015", 5 pgs.
"International Application Serial No. PCT/US2015/017741, Written Opinion dated Aug. 7, 2015", 7 pgs.
"International Application Serial No. PCT/US2015/063621, International Search Report dated Mar. 23, 2016", 6 pgs.
"International Application Serial No. PCT/US2015/063621, Written Opinion dated Mar. 23, 2016", 7 pgs.
"International Application Serial No. PCT/US2016/022896, International Search Report dated Jun. 30, 2016", 7 pgs.
"International Application Serial No. PCT/US2016/022896, Written Opinion dated Jun. 30, 2016", 7 pgs.
"Japanese Application Serial No. 2008-526378, Office Action dated Jun. 19, 2012", (w/ English translation), 6 pgs.
"Japanese Application Serial No. 2008-526378, Office Action dated Sep. 6, 2011", (w/ English Translation), 11 pgs.
"Japanese Application Serial No. 2008-526378, Office Action dated Dec. 18, 2012", (w/ English translation), 4 pgs.
"Japanese Application Serial No. 2008-526378, Response filed Mar. 6, 2012 to Office Action dated Sep. 6, 2011", (w/ English translation of claims), 10 pgs.
"Japanese Application Serial No. 2008-526378, Response filed May 28, 2013 to Office Action dated Dec. 18, 2012", (w/ English translation of claims), 8 pgs.
"Japanese Application Serial No. 2008-526378, Response filed Oct. 19, 2012 to Examiners Decision of Final Refusal dated Jun. 19, 2012", (w/ English translation of claims), 13 pgs.
"Japanese Application Serial No. 2010-503206, Examiners Decision of Final Refusal dated May 7, 2013", (w/ English translation), 5 pgs.
"Japanese Application Serial No. 2010-503206, Office Action dated Dec. 4, 2012", (w/ English translation), 7 pgs.
"Japanese Application Serial No. 2010-503206, Response filed Mar. 4, 2013 to Office Action dated Dec. 4, 2012", (w/ English translation), 13 pgs.
"Japanese Application Serial No. 2012-049675, Examiners Decision of Final Refusal dated Sep. 30, 2014", (W/ English Translation), 9 pgs.
"Japanese Application Serial No. 2012-049675, Office Action dated Jan. 30, 2015", (w/ English translation of claims), 16 pgs.
"Japanese Application Serial No. 2012-049675, Office Action dated Sep. 3, 2013", (w/ English translation), 13 pgs.
"Japanese Application Serial No. 2012-049675, Response filed Feb. 28, 2014 to Office Action dated Sep. 3, 2013", (W/ English Translation), 14 pgs.
"Japanese Application Serial No. 2015-016315, Amendment filed Feb. 26, 2015", (W/ English Translation), 8 pgs.
"Japanese Application Serial No. 2015-016315, Office Action dated Nov. 30, 2015", (W/ English Translation), 13 pgs.
"Japanese Application Serial No. 2015-016315, Response filed Mar. 7, 2016 to Office Action dated Nov. 30, 2015", (W/ English Translation), 11 pgs.
"Joint Replacement Material Developed at the Massachusetts General Hospital", from MA General Hosp. MGH Hotline On-line publication, (Aug, 10, 2007), 1 pg.
"New joint replacement material developed at Massachusetts General Hospital and put to first clinic use", news release from Massachusetts General Hospital, accessed May 13, 2008, (Nov. 15, 2010), 2 pgs.
"Opposition Application No. 09013154.1, Opposition Brief filed Apr. 16, 2014", (w/ English Translation), 22 pgs.
"Opposition to EP 2277560, Response filed Feb. 26, 2015 to Notice of Opposition filed on Jul. 4, 2014", 12 pgs.
"Prevention of Fatigue Cracks in Ultrahigh Morecular Weight Polyethylene Joint Components by the Addition of Vitamin E", J. Biomed. Mater. Res., vol. 48,, (1999), 474-478.
"Studies on the effect of electron beam radiation on the• molecular structure of ultra-high molecularweight polyethylene under the influence of a-tocopherol with respect to its application in medical implants", J. Materials Science: Materials in Medicine, vol. 13, No. 10, (2002), 917-921.
"The anti-oxidative properties of a-tocopherol in y-irradiated UHMWPE with respect to fatigue and oxidation resistance", Biomatyerials, vol. 26, (Apr. 1, 2005), 5755-5762.
Badertscher, R. P., et al., "Grafting of a-tocopherol upon y-irradiation UHMWPE probed by model hydrocarbons", Polymer Degradation and Stability, 97, (2012), 2255-2261.
Bauer, I., et al., "Antioxidant interaction between organic phosphites and hindered amine light stabilisers during processing and thermoxidation of polypropylene", Polymer Degradation and Stability, 48(3), (1995), 427-440.
Bauer, I., et al., "Antioxidant interaction between organic phosphites and hindered amine light stabilizers: effects during photoxidation of polypropylene—II", Polymer Degradation and Stability, 55(2), (1997), 217-224.
Bauer, I., et al., "Hydroperoxide decomposing ability and hydrolytic stability of organic phosphites containing hindered amine moieties (HALS-Phosphites)", Polymer Degradation and Stability, 62(1), (1998), 175-186.
Bragdon, et al., "A New Pin-on-disk wear testing method for simulating wear of polyethylene on cobalt-chrome alloy in total hip arthroplasty", The Journal of Arthoplasty vol. 16, No, 5, (2001), 658-665.
Chmela, S., et al., "HALS-phosphite combinations as light and heat stabilizers for polypropylene", Polymer Degradation and Stability, 39(3), (1993), 367-371.
Davidson, Ernesto, et al., "Characterization of UHMWPE Irradiated with gamma rays stored in E vitamin and thermally treated", Revista De La Facultad De Ingenieria Universidad Central De Venezuela, 26(1),, (2011), 7 pgs.
Greer, K. W., et al., "The Effects of Raw Material, Irradiation Dose, and Irradiation Source on Crosslinking of UHMWPE", Journal of ASTM International, vol. 1, No. 1, (Jan. 2004), pp. 1-11.
Habicher, Wolf D, et al., "Synthesis and antioxidative properties of novel multifunctional stabilizers", Journal of Vinyl and Additive Technology, 7(1), (Mar. 2001), 4-18.
Hahner, U., et al., "Synthesis and antioxidative efficiency of organic phosphites and phosphonites with 2.2.6.6-tetramethylpiperidin-4-yl groups", Polymer Degradation and Stability, 41(2), (1993), 197-203.
John, Ingo, "Evaluation of cross-linked UHMWPE with regards to its suitability as implant material for hip joint shells(Beurteilung von vernetztem UHMWPE hinsichtlich seiner Eignung als

(56) References Cited

OTHER PUBLICATIONS

Implantatwerstoff für Hüftgelenkschalen)", Technische Universität Berlin, ISBN: 978-3-7983-1934-9 w/ ENglish Translation, (2003), 155 pgs.

Kurtz, S, et al., "Trace Concentrations of Vitamin E Protect Radiation Crosslinked UHMWPE from Oxidative Degradation", 53rd Annual Meeting of the Orthopaedic Research Society,.Feb. Paper No. 0020, (Nov. 14, 2007), 1 pg.

Muratoglu, Orhun K., et al., "A Novel Method of Cross-Linking Ultra-High-Molecular-Weight Polyethylene to Improve Wear, Reduce Oxidation, and Retain Mechanical Properties", The Journal of Arthroplasty, vol. 16, No. 2, (2001), 149-160.

Muratoglu, Orhun K, et al., "Larger Diameter Femoral Heads Used in Conjunction With a Highly Cross-Linked Ultra-High Molecular Weight Polyethylene: A New Concept", The Journal of Arthoplasty 16(8) Suppl. 1, (2001), 24-30.

Oral, et al., "Alpha-Tocopherol-doped irradiated UHMWPE for high fatigue resistance and low wear", Biomaterials vol. 25, (2004), 5515-5522.

Oral, et al., "Blending a-Tocopherol with UHMWPE Powder for Oxidation Resistance", Poster 1485, 50th Annual Meeting of Orthopaedic Research Society, San Francisco CA, Mar. 7-10, 2004, Transactions, vol. 29, (2004), 1 pg.

Oral, E, et al., "Characterization of irradiated blends of alpha-tocopherol and UHMWPE", Biomaterials, 26(33), (Nov. 2005), 6657-6663.

Oral. E, et al., "Crosslinked Vitamin E Blended UHMWPE with Improved Grafting and Wear Resistance", ORS Annual Meeting, Poster No. 1181, (2011), 1 pg.

Oral, E, et al., "Trace amounts of grafted vitamin E protect UHMWPE against squalene-initiated oxidation", ORS Annual Meeting, Poster No. 1295, (2011), 1 pg.

Parth, M., et al., "Studies on the effect of electron beam radiation on the molecular structure of ultra-high molecular weight polyethylene under the influence of a-tocopherol with respect to its application in medical implants", Journal of Materials Science: Materials in Medicine, 13(10), (2002), 917-921.

Pletcher, Dirk, et al., "Polymers Compositions Including an Anti-oxidant", U.S. Appl. No. 12/813,401, Application filed Jun. 10, 2010, 52 pgs.

Rowell, S, et al., "Detection of Vitamin E in Irradiated UHMWPE by UV-Visible Spectroscopy", ORS 2011 Annual Meeting, Poster No. 1186, (2011), 1 pg.

Rufner, Alicia, et al., "An Antioxidant Stabilized Crosslinked Ultra-High Molecular Weight Polyethylene for Medical Device Applications", U.S. Appl. No. 12/847,741, Application filed Jul. 30, 2010, 69 pgs.

Shibata, N, et al., "The anti-oxidative properties of alpha-tocopherol in gamma-irradiated UHMWPE with respect to fatigue and oxidation resistance", Biomaterials, 26(29), (Apr. 19, 2005), 5755-5762.

Tomita, N., et al., "Prevention of fatigue cracks in ultrahigh molecular weight polyethylene joint components by the addition of vitamin E", J Biomed Mater Res., 48(4), (1999), 474-478.

Wannomae, et al., "Vitamin E Stabilized, Irradiated UHMWPE for Cruciate Retaining Knee Components", 53rd Annual Meeting of the Orthopaedic Research Society, Poster No. 1783, (Nov. 14, 2007), 1 pg.

Wolf, C, et al., "Radiation Grafting of Vitamine E to Ultra High Molecular Weight Polyethylene", ORS Annual Meeting, Poster No. 1178, (2011), 1 pg.

\* cited by examiner

MELT-STABILIZED ULTRA HIGH MOLECULAR WEIGHT POLYETHYLENE AND METHOD OF MAKING THE SAME

CROSS-REFERENCE TO RELATED APPLICATION

This application is a U.S. National Stage Filing under 35 U.S.C. 371 from International Application No. PCT/US2015/017741, filed on 26 Feb. 2015, and published as WO 2015/138137 A1 on 17 Sep. 2015, which claims the benefit of priority to U.S. Provisional Patent Application Ser. No. 61/951,661, filed Mar. 12, 2014, the disclosures of each of which are incorporated herein in its entirety by reference.

BACKGROUND OF THE INVENTION

Ultra high molecular weight polyethylene (UHMWPE) is the most widely used material for orthopedic implants that articulate, such as for hip, knee, ankle, elbow and shoulder joint replacement due to osteoarthritis. First implemented in the early 1960's, a major concern for this material has been high wear rate with generation of microscopic wear particles over years of articulation. A known outcome of a high polyethylene particulate burden is a condition known as osteolysis, which results in implant loosening with subsequent need for revision surgery. This concern was addressed in the late 1990's with the introduction of highly crosslinked UHMWPE, which is crosslinked by the use of high energy irradiation such as gamma or electron beam. Crosslinking reduces the wear rate of UHMWPE significantly, but also leaves a high free radical burden in the polyethylene, which if not reduced can cause oxidation in-vivo, with subsequent reduction in mechanical properties, increasing wear rates, and potential implant failure.

To address the free radical burden, highly crosslinked UHMWPE is most often heat stabilized by raising the material temperature above the melting point of the material. This allows the trapped free radicals that did not participate in crosslinking to promote further crosslinking in the material, or to re-combine, rendering them to an inert state that will not promote premature oxidative degradation. However, the melting process can cause the formation of a significant oxidized layer on the exterior of the material if the melting process is done in an oxygen-containing environment such as air, where sufficient oxygen is present to diffuse into the material in the molten state. This oxidized layer is removed during fabrication of the implant to prevent contamination of the implant with oxidatively degraded UHMWPE.

SUMMARY OF THE INVENTION

In various embodiments, the present invention provides a method of melt-stabilizing a material including UHMWPE. The method includes obtaining or providing a solid material including UHMWPE. The UHMWPE includes a first concentration of free-radicals. The method includes coating at least part of the solid material with a liquid composition including at least one antioxidant. The coating of the solid material provides a coated solid material. The method includes heating the coated solid material in an environment including oxygen. The heating is sufficient to melt at least part of the UHMWPE. The heating of the coated solid material provides a heated material. The method also includes solidifying the heated material. The solidifying provides a melt-stabilized material including UHMWPE. The UHMWPE in the melt-stabilized material includes a second concentration of free-radicals. The second concentration of free-radicals is less than the first concentration of free-radicals.

In various embodiments, the present invention provides a method of melt-stabilizing a material including UHMWPE. The method includes obtaining or providing a solid material including about 90 wt % to about 100 wt % UHMWPE. The UHMWPE includes a first concentration of free-radicals of at least about $1 \times 10^{15}$ spins/g. The UHMWPE is an irradiated UHMWPE. The method includes coating about 90% to about 100% of a surface of the solid material with a liquid composition including at least one antioxidant. The antioxidant is at least one of vitamin E, vitamin E acetate, pentaerythritol tetrakis(3-(3,5-di-tert-butyl-4-hydroxyphenyl) propionate), butanedioic acid dimethyl ester/4-hydroxy-2,2,6,6-tetramethyl-1-piperidine ethanol copolymer, tannic acid, and bilberry extract. The antioxidant is about 5 wt % to about 100 wt % of the liquid composition. The coating of the solid material provides a coated solid material. The method includes heating the coated solid material in an environment including about 1 vol % to about 30 vol % oxygen. The heating is sufficient to melt at least part of the UHMWPE. The heating of the coated solid material provides a heated material. The method also includes solidifying the heated material, to provide a melt-stabilized material including UHMWPE. The UHMWPE in the melt-stabilized material includes a second concentration of free-radicals of less than about $1 \times 10^{15}$ spins/g. The UHMWPE in a surface layer of the melt-stabilized material has an oxidation index that does not exceed 1.

In various embodiments, the present invention provides a medical implant including an oxygen-containing-environment-melt-stabilized material including UHMWPE. The melt-stabilized material is free of post-melt-stabilization oxidized surface layer removal greater than 3 mm depth. The UHMWPE in a surface layer of the melt-stabilized material has an oxidation index that does not exceed 1.

Various embodiments of the present invention provide certain advantages over other melt-stabilized UHMWPE, methods of making the same, and medical implants made from the same. For example, in some embodiments, the method of melt-stabilizing UHMWPE can melt-stabilize a UHMWPE in an oxygen-containing environment (e.g., air) with less or no formation of an oxidized layer on the surface of the melt-stabilized UHMWPE. Medical-grade UHMWPE can represent a significant cost in the production of a medical implant including UHMWPE. Oxidation of the surface of UHMWPE during melt-stabilization results in the removal and discarding of the oxidized layer due to unsuitability for medical-implant preparation. In some embodiments, as compared to other techniques for melt-stabilizing UHMWPE in an oxygen-containing environment, the method can form a melt-stabilized UHMWPE that is ready to form into a medical implant with less or no removal of a surface layer. In various embodiments, by avoiding or decreasing removal of an oxidized surface layer of UHWMPE, the method provides cost savings over other methods by decreasing the amount of UHMWPE that is wasted by the melt-stabilization process. In various embodiments, as compared to techniques using an oxygen-free or oxygen-depleted environment for melt-stabilization, the method provides costs savings by avoiding equipment, supplies, and time-consuming techniques needed for generating an oxygen-free or oxygen-depleted environment.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1A:
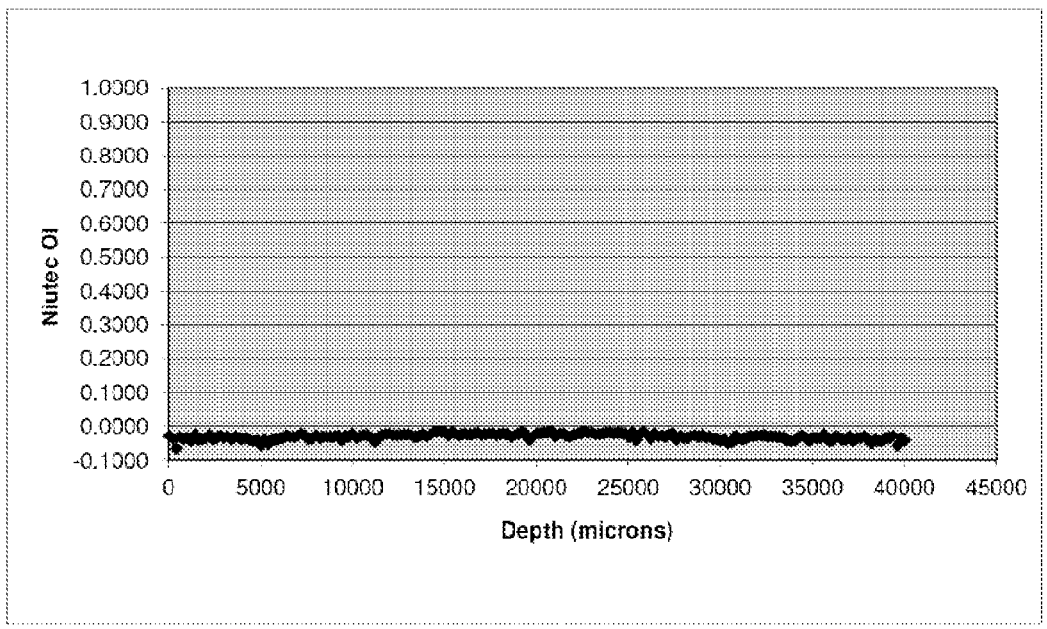
FIG. 1a illustrates oxidation index versus depth from the top to the bottom of the sample of Example 1, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The term "organic group" as used herein refers to but is not limited to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein refers to an organic group as defined herein or molecule in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitrites, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 or 12-40 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, and the like.

The term "hydrocarbon" as used herein refers to a functional group or molecule that includes carbon and hydrogen atoms. The term can also refer to a functional group or molecule that normally includes both carbon and hydrogen atoms but wherein all the hydrogen atoms are substituted with other functional groups.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species i having $n_i$ molecules of molecular weight $M_i$ through the formula $M_n = \Sigma M_i n_i / \Sigma n_i$. The number-average molecular weight can be measured by a variety of well-known methods including gel permeation chromatography, spectroscopic end group analysis, and osmometry. If unspecified, molecular weights of polymers given herein are number-average molecular weights.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

The term "solvent" as used herein refers to a liquid that can dissolve a solid, liquid, or gas. Nonlimiting examples of solvents are silicones, organic compounds, water, alcohols, ionic liquids, and supercritical fluids.

The term "air" as used herein refers to a mixture of gases with a composition approximately identical to the native composition of gases taken from the atmosphere, generally at ground level. In some examples, air is taken from the ambient surroundings. Air has a composition that includes approximately 78% nitrogen, 21% oxygen, 1% argon, and 0.04% carbon dioxide, as well as small amounts of other gases.

The term "room temperature" as used herein refers to a temperature of about 15° C. to 28° C.

The term "coating" as used herein refers to a continuous or discontinuous layer of material on the coated surface, wherein the layer of material can penetrate the surface and can fill areas such as pores, wherein the layer of material can have any three-dimensional shape, including a flat or curved plane. In one example, a coating can be formed on one or more surfaces, any of which may be porous or nonporous, by immersion in a bath of coating material.

The term "surface" as used herein refers to a boundary or side of an object, wherein the boundary or side can have any perimeter shape and can have any three-dimensional shape, including flat, curved, or angular, wherein the boundary or side can be continuous or discontinuous. While the term "surface" generally refers to the outermost boundary of an object with no implied depth, when the term "pores" is used in reference to a surface, it refers to both the surface opening and the depth to which the pores extend beneath the surface into the substrate.

Method of Melt-stabilizing a Material.

Oxidation of polyethylene can occur through a free radical pathway, as shown in the following sequence:

RH+IN→R. Initiation
R.+$O_2$→ROO.
ROO.+RH→ROOH+R. Propagation
ROOH→RO.+HO.
RO.+RH→ROH+R Chain Branching
HO.+RH→HOH+R.
ROO.(RO. etc.)→Inert Products Termination
ROO.+AH→ROOH+A.
RO.+AH→ROH+A. Inhibition (stabilization)
HO.+AH→HOH+A.
wherein
RH=polymer (e.g., polyethylene, UHMWPE)
IN=initiator (e.g., irradiation)
AH=inhibitor (e.g., free-radical scavenging antioxidant)

Various embodiments of the present invention provide a means to reduce the oxidized layer that forms during melt-stabilization of a material including UHMWPE in an oxygen-containing environment such as air. Prior to melt-stabilizing, a liquid composition including an antioxidant vitamin E solution is applied to the exterior of the solid material including UHMWPE, such as after irradiation. During the melt-stabilization method, the applied antioxidant penetrates the exterior of the material, scavenging the free radicals present in the outer layer that would normally be oxidized.

In various embodiments, the present invention provides a method of melt-stabilizing a material including UHMWPE. The method can include obtaining or providing a solid material including UHMWPE including a first concentration of free-radicals. The method can include coating at least part of the solid material with a liquid composition including at least one antioxidant, to provide a coated solid material. The method can include heating the coated solid material in an environment including oxygen, the heating sufficient to melt at least part of the UHMWPE, to provide a heated material. The method can also include solidifying the heated material, to provide a melt-stabilized material including UHMWPE including a second concentration of free-radicals, wherein the second concentration of free-radicals is less than the first concentration of free-radicals.

The first concentration of free-radicals in the solid material including UHMWPE can be any suitable concentration, such as about $1 \times 10^{15}$ spins/gram to about $1 \times 10^{20}$ spins/g, $1 \times 10^{16}$ spins/g to $1 \times 10^{18}$ spins/g, or about $1 \times 10^{15}$ spin/g or less, or about $1 \times 10^{16}$ spins/g, $1 \times 10^{17}$, $1 \times 10^{18}$, $1 \times 10^{19}$, $1 \times 10^{20}$, $1 \times 10^{21}$, $1 \times 10^{22}$, $1 \times 10^{23}$, $1 \times 10^{24}$, $1 \times 10^{25}$, $1 \times 10^{26}$, $1 \times 10^{27}$, $1 \times 10^{28}$, $1 \times 10^{29}$, or about $1 \times 10^{30}$ spins/g or more. The number of spins per gram of the material can be measured in any suitable fashion, such as by electron spin resonance (ESR). The first concentration of free-radicals can be a concentration in the UHMWPE or a concentration in all the materials in the solid material including the UHMWPE. The first concentration of free-radicals can be a concentration in a part or localized area of the solid material, or can be a concentration throughout the entire solid material including the UHMWPE. In some embodiments, the first concentration of free-radicals can be generated by and consistent with an amount of irradiation applied to the solid material to crosslink the UHMWPE or to crosslink other components in the solid material.

The melt-stabilization method reduces the concentration of free-radicals. The concentration of free-radicals in the UHWMPE can be reduced. The concentration of free-radicals in other materials can also optionally be reduced, for solid materials including materials in addition to UHMWPE, such as other polyethylenes or other polymers. The second concentration of free-radicals in the melt-stabilized solid material can be any suitable concentration that is lower than the first concentration of free radicals, such as about $1 \times 10^{5}$ spins/g to about $1 \times 10^{15}$ spins/g, or about $1 \times 10^{2}$ spins/g or less, or about $1 \times 10^{3}$ spins/g, $1 \times 10^{4}$ $1 \times 10^{5}$, $1 \times 10^{6}$, $1 \times 10^{7}$ $1 \times 10^{8}$, $1 \times 10^{9}$, $1 \times 10^{10}$, $1 \times 10^{11}$, $1 \times 10^{12}$, $1 \times 10^{13}$, $1 \times 10^{14}$ spins/g, $1 \times 10^{15}$ spins/g or more. The number of spins per gram of the material can be measured in any suitable fashion, such as by electron spin resonance (ESR). The second concentration of free-radicals can be a concentration in the UHMWPE or a concentration in all the materials in the solid material including the UHMWPE, corresponding to the first concentration of free-radicals. The second concentration of free-radicals can be a concentration in a part or localized area of the solid material (e.g., corresponding to a part or localized area where the first concentration of free-radicals is measured), or can be a concentration throughout the entire solid material including the UHMWPE. The second concentration of free-radicals can be any suitable proportion of the first concentration of free-radicals. For example, the second concentration of free-radicals can be about 1% to about 0.000.1% of the first concentration of free-radicals, about 0.1% to about 0.001%, or about 1% or more, or about 0.5%, 0.1, 0.05, 0.01, 0.005, 0.001, 0.000.5, or about 0.000.1% or less.

The method can be effective to generate a melt-stabilized material including UHMWPE, melt-stabilized in an environment including oxygen, that has decreased or no oxidation in a surface layer of the material, as compared to other methods for melt-stabilization in an oxygen-containing environment. The surface layer including decreased or no oxidation can be a surface layer that corresponds to the entire outer surface of the material, such as for a material including UHMWPE on the entire surface of the material (e.g., the material can be 100% UHMWPE or can have UHMWPE distributed evenly throughout). The surface layer can be a portion of the outer surface that corresponds to a portion of the outer surface of the material, such as for a material including UHMWPE on only a portion of the surface of the material, or such as for a material that was only partially coated with the liquid composition including the antioxidant.

As used herein, "oxidation index" refers to an area ratio of fourier transform infrared (FTIR) peaks at 1765-1680 $cm^{-1}$ (e.g. carbonyl peaks) to FTIR peaks 1392-1330 $cm^{-1}$ (e.g., methyl peaks), wherein the area of the carbonyl absorptions centered near 1720 $cm^{-1}$ is related to the amount of chemically bound oxygen present in the material, and the intensity (area) of the C—H absorption centered near 1370 $cm^{-1}$ is used normalize for the sample's thickness. A surface layer (e.g., the entire surface, or only part of the surface, of any suitable depth) of the melt-stabilized material can have an oxidation index that does not exceed 1 (e.g., the average oxidation index of the surface layer does not exceed an oxidation index of 1 or any portion of the surface layer does not exceed an oxidation index of 1). For example, in some embodiments, the surface layer of the melt-stabilized material has an oxidation index that does not exceed 0.5, or that is about 0.001 to about 1, 0.01 to about 0.5, or about 0.001 or less, or that is equal to or less than about 0.002, 0.003, 0.004, 0.005, 0.006, 0.008, 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.15, 0.2, 0.25, 0.3, 0.35, 0.4, 0.45, 0.5, 0.6, 0.7, 0.8, 0.9, or about 1 or more. The surface layer can be a layer of any suitable depth on the material, such as about 0 mm deep (e.g., the top surface most exposed to oxygen), or a layer about 0 mm deep to about 1 mm deep, about 0 mm deep and about 10 mm deep, or about 1 mm deep or less, or about 2 mm, 3, 4, 5, 6, 7, 8, 9, 10, 11, 12, 13, 14, 15, 16, 17, 18, 19, or about 20 mm deep or more.

In certain examples, one or more agents, e.g., bioactive agents, can be added to the material that is melt-stabilized. Such addition can be accomplished during any stage of preparation but may be desirable after any heat treatments are performed to reduce the likelihood of deactivation of the bioactive agent. Illustrative agents include, but are not limited to, an antibiotic, a steroid, a drug, a growth factor such as bone morphogenic protein, an osteocyte, an osteoclast or other cells, a vitamin, a chondroitin, a glucosamine, a glycosoaminglycan, high energy phosphates such as phosphoenolpyruvate, ATP, 5'-AMP and other small molecule biologics or other chemical or biological agents. In some examples, the material that is melt-stabilized can be loaded with stem cells, and the material can act as a scaffold to permit growth and differentiation of bone or cartilage within the polymer framework. The presence of an antioxidant in the material that is melt-stabilized (e.g., via mixture with the UHMWPE, or via coating) can act to prevent degradation of the scaffold in its use environment and may also provide some oxidative protection to the bioactive agent or stem cells loaded into the scaffold.

In certain examples, subsequent to or after production of the melt-stabilized material, the material can be molded, compressed, consolidated or otherwise processed to provide a desired shape, part size or other physical attributes to render the part suitable for its intended use.

In certain embodiments, additional components may be combined with the material that is melt-stabilized at any time during the process. In one embodiment, tribological components such as metal and/or ceramic articulating components and/or preassembled bipolar components may be joined with the material that is melt-stabilized. In other embodiments, metal backing (e.g., plates or shields) may be added. In further embodiments, surface components such a trabecular metal, fiber metal, Sulmesh™ coating, meshes, cancellous titanium, and/or metal or polymer coatings may be added to or joined with the material that is melt-stabilized. Radiomarkers or radiopacifiers such as tantalum, steel and/or titanium balls, wires, bolts or pegs may be added. Locking features such as rings, bolts, pegs, snaps and/or cements/adhesives can be added. These additional components may be used to form sandwich implant designs, radiomarked implants, metal-backed implants to prevent direct bone contact, functional growth surfaces, and/or implants with locking features.

Solid Material Including UHMWPE.

The method includes obtaining or providing a solid material comprising UHMWPE comprising a first concentration of free-radicals. Any suitable proportion of the solid material can be the UHMWPE, such as about 1 wt % to about 100 wt % of the solid material, about 90 wt % to about 100 wt %, or about 1 wt % or less, or about 2, 3, 4, 5, 10, 15, 20, 25, 30, 35, 40, 45, 50, 55, 60, 65, 70, 75, 80, 85, 90, 95, 96, 97, 98, 99, or about 99.9 wt % or more. The UHMWPE can form a homogeneous or heterogeneous mixture with other components in the solid material.

UHWMPE is a semi crystalline, linear homopolymer of ethylene, which in some embodiments can be produced by stereospecific polymerization with a Ziegler-Natta catalyst at low pressure (6-8 bar) and low temperature (66-80° C.). The synthesis of UHMWPE can result in a fine granular powder. The molecular weight and its distribution can be controlled by process parameters such as temperature, time and pressure. UHMWPE generally has a molecular weight of at least about 2,000,000 g/mol. Suitable UHMWPE materials for use as raw materials may be in the form of a powder or mixture of powders. Examples of suitable UHMWPE materials include GUR® 1020 and GUR® 1050 available from Ticona Engineering Polymers.

In addition to UHMWPE, the solid material can include any other suitable component. In certain embodiments, the UHWMPE can be combined with another crosslinkable polymer. The crosslinkable polymer can be any polymer that can be cross-linked using radiation, a chemical crosslinking agent or that can be physically cross-linked under suitable conditions. In some examples, the polymer can be a thermoplastic polymer such as, for example, an acrylonitrile butadiene styrene (ABS) polymer, an acrylic polymer, a celluloid polymer, a cellulose acetate polymer, a cycloolefin copolymer (COC), an ethylene-vinyl acetate (EVA) polymer, an ethylene vinyl alcohol (EVOH) polymer, a fluoroplastic, an ionomer, an acrylic/PVC alloy, a liquid crystal polymer (LCP), a polyacetal polymer (POM or acetal), a polyacrylate polymer, a polyacrylonitrile polymer (PAN or acrylonitrile), a polyamide polymer (PA or nylon), a polyamide-imide polymer (PAD, a polyaryletherketone polymer (PAEK or ketone), a polybutadiene polymer (PBD), a polybutylene polymer (PB), a polybutylene terephthalate polymer (PBT), a polycaprolactone polymer (PCL), a polychlorotrifluoroethylene polymer (PCTFE), a polyethylene terephthalate polymer (PET), a polycyclohexylene dimethylene terephthalate polymer (PCT), a polycarbonate polymer, a polyhydroxyalkanoate polymer (PHA), a polyketone polymer (PK), a polyester polymer, a polyethylene polymer (PE), a polyetheretherketone polymer (PEEK), a polyetherketoneketone polymer (PEKK), a polyetherimide polymer (PEI), a polyethersulfone polymer (PES), a polyethylenechlorinate polymer (PEC), a polyimide polymer (PI), a polylactic acid polymer (PLA), a polymethylpentene polymer (PMP), a polyphenylene oxide polymer (PPO), a polyphenylene sulfide polymer (PPS), a polyphthalamide polymer (PPA), a polypropylene polymer, a polystyrene polymer (PS), a polysulfone polymer (PSU), a polytrimethylene terephthalate polymer (PTT), a polyurethane polymer (PU), a polyvinyl acetate polymer (PVA), a polyvinyl chloride polymer (PVC), a polyvinylidene chloride polymer (PVDC), and a styrene-acrylonitrile polymer (SAN). Illustrative types of polyethylene in addition to the UHMWPE include, for example, ultra low molecular weight polyethylene (ULMWPE), high molecular weight polyethylene (HMWPE), high density polyethylene (HDPE), high density cross-linked polyethylene (HDXLPE), cross-linked polyethylene (PEX or XLPE), medium density polyethylene (MDPE), low density polyethylene (LDPE), linear low density polyethylene (LLDPE) and very low density polyethylene (VLDPE). In some examples, a polypropylene can be used. A polypropylene may be particularly desirable where the final product is a mesh, stent, breast implant material, suture material or other medical device. In one alternative, a polypropylene (or other polymer) may be used as one layer in a multi-layered medical device. Illustrative polypropylenes include, but are not limited to, a homopolymeric polypropylene, a block copolymeric polypropylene, and a random copolymeric polypropylene. In certain examples, the polymers used in the compositions described herein can be copolymerized with one or more monomers or polymers. The solid material can be a consolidated mixture of UHMWPE and any other suitable component, wherein the consolidation can include any suitable consolidation technique such as compression molding, direct compression molding, hot isostatic pressing, ram extrusion, high pressure crystallization, injection molding, sintering, and a combination thereof.

In certain examples, the solid material can include one or more suitable additives that impart a desired physical or chemical property. Illustrative suitable additives include, but are not limited to radiopaque materials, antimicrobial materials such as silver ions, antibiotics, and microparticles and/or nanoparticles serving various functions. Preservatives, colorants and other conventional additives may also be used.

In some embodiments, the solid material is an irradiated material. In some embodiments, the method includes performing the irradiation, whereas in other embodiments, the material has been irradiated prior to the initiation of the method. In some embodiments, the UHMWPE in the solid material has been irradiated, such as to crosslink the UHMWPE and optionally other components in the solid material as well. In some embodiments, the method includes irradiating UHMWPE or irradiating a pre-irradiated mixture of UHMWPE and other components to provide the solid material including the UHMWPE, wherein the pre-irradiated mixture can be free of prior irradiation or can have been exposed to prior irradiation. In some embodiments, the method includes irradiating UHMWPE and optionally other components, then combining the irradiated material with other materials in any suitable fashion to provide the solid material including the UHMWPE. In some examples, the UHMWPE or mixture of UHMWPE and other components can be irradiatively crosslinked to provide the solid material, either in the presence of absence an antioxidant (e.g., such as any antioxidant described herein, in any concentration and having a homogenous or heterogeneous distribution within the UHMWPE), before the coating with antioxidant and the subsequent melt-stabilization.

Irradiation to provide the solid material can be any suitable irradiation. The irradiation can be visible light radiation, infrared radiation, ultraviolet radiation, electron beam radiation, gamma radiation, or X-ray radiation. Where ionizing radiation is employed to effect the crosslinking reaction, the radiation can be obtained from any suitable source such as an atomic pile, a resonant transformer accelerator, a Van de Graaff electron accelerator, a Linac electron accelerator, a betatron, a synchrotron, a cyclotron, or the like. Radiation from these sources will produce ionizing radiation such as electrons, protons, neutrons, deuterons, gamma rays, X rays, alpha particles, and beta particles. Where ionizing radiation is used, a sufficient radiation dose rate and/or absorbed dose can be used to induce crosslinking and/or control the degree of crosslinking. In some embodiments, during the irradiation, the temperature of the UHMWPE or mixture of UHMWPE and other components can be maintained below the melting point of the same. In some embodiments, during the irradiation, the temperature of the UHMWPE or mixture of UHMWPE and other components can be allowed to rise above the melting point of the same. In some embodiments, the UHMWPE or mixture of UHMWPE and other components can be preheated prior to irradiation, such as to a temperature above room temperature and below or above the melting point of the UHMWPE or mixture of UHMWPE and other components, such as about 50° C. to about 110° C., 115° C., 120° C., 125° C., 130° C., 140° C., 145° C., or to about 150° C., such that at the time of irradiation onset the material has a preheated temperature. In various embodiments, the UHMWPE or mixture of UHMWPE and other components can be preheated to a temperature below the melting point of the same, then subsequently irradiated while maintaining the temperature of the preheated UHMWPE or mixture of UHMWPE and other components below the melting point of the same. The solid material can optionally be consolidated before a preheating step and before an irradiation step.

In various embodiments, the solid material, or the UHMWPE in the solid material, is produced by irradiating the material, such as with electron-beam irradiation or gamma irradiation, using a total dose of about 1 kGy to about 100,000 kGy, 10 kGy to about 1000 kGy, about 50 kGy to about 200 kGy, 65 kGy to 100 kGy, or about 1 kGy or less, or about 5, 10, 15, 20, 25, 50, 75, 100, 125, 150, 175, 200, 250, 300, 400, 500, 750, 1,000, 1,250, 1,500, 1,750, 2,000, 2,500, 3,000, 4,000, 5,000, 7,500, 10,000, 15,000, 20,000, 25,000, 50,000, 75,000, or about 100,000 kGy or more.

In certain examples, irradiative crosslinking can be performed in the presence of an additive that can promote or deter crosslinking, depending on the desired level of crosslinking in the solid material. Illustrative crosslinking promoters include, but are not limited to, trimethylolpropane triacrylate, trimethylolpropane trimethacrylate, pentaerythritol tetraacrylate, and pentaerythritol tetramethacrylate. In certain instances, one or more antioxidants can be present to reduce the degree of crosslinking. Alternatively, other reagents that can scavenge free radicals can be present to reduce the degree of crosslinking in the solid material.

In certain embodiments, before crosslinking irradiation, a material including UHMWPE can be prepared via a number of known processes to form a blend, such as a blend with another polymer or a blend with an antioxidant. Such processes include physical mixing, mixing with the aid of a solvent, mixing with the aid of a solvent (e.g., $CO_2$) under supercritical temperature and pressure conditions, and ultrasonic mixing. Suitable mixing processes of these types are also described, for example, in U.S. Pat. Nos. 6,448,315 and 6,277,390, the disclosures of which are hereby incorporated by reference. Consolidation can be performed after blending.

Coating.

In various embodiments, the method includes coating at least part of the solid material with a liquid composition comprising at least one antioxidant, to provide a coated solid material. The coating can be any suitable coating method that applies the antioxidant in the liquid composition sufficiently such that the antioxidant can penetrate a surface layer of the solid material and protect the solid material from oxidation by oxygen in the air during melt-stabilizing. For example, the coating can allow the antioxidant in the liquid composition to penetrate into the UHMWPE on the surface of the solid material and protect the UHMWPE in the solid material from oxidation by oxygen in the air, as described herein. The coating can be performed using any suitable coating process, such as one or more of brushing, dipping, soaking, immersion with agitation or stirring, spraying, and the like.

The coating can be sufficient to penetrate any suitable depth from the surface of the solid material where the coating is applied, such as about 0 mm to about 1 mm, about 0 mm to about 10 mm deep, about 0 mm to about 20 mm deep, about 1 mm or less, or about 1.5 mm, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 mm or more. In various embodiments, the depth of penetration of the coating can depend on various factors, such as the duration of time the liquid composition including the antioxidant is allowed to contact the solid material, the temperature used during the contacting (e.g., the temperature of the liquid composition, the temperature of the solid material, or both), the solubility of the liquid composition in the solid material, the molecular size of the antioxidant, the molecular weight of the antioxidant. In various embodiments, the coating can be performed such that the liquid composition does not penetrate past a certain depth of the solid material. For example, in some embodiments, the coating penetrates the solid material no deeper than about 1 mm or less, or about 1.5 mm, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19 mm, or about 20 mm or more. In some embodiments, the coating does not penetrate past the surface layer, wherein the non-surface layer portions of the solid material are substantially free of the liquid composition.

The coating can include coating any suitable proportion of the total surface area of the solid material. The coating can be sufficient to contact at least some of the UHMWPE in the solid material and the liquid composition (e.g., the antioxidant in the liquid composition), wherein the UHMWPE can be on the surface or proximate to the surface (e.g., within 1 mm to about 10 mm). In an embodiment wherein the solid material only has exposed UHMWPE on a portion of the surface, or only has UHMWPE within about 1-10 mm of only a portion of the surface, the method can optionally include only coating the part of the surface of the solid material that includes the UHMWPE or that is proximate to UHMWPE. For example, the coating can include coating about 1% to about 100% of the total surface area of the solid material, about 50% to about 100%, about 90% to about 100%, or about 1% or less, or about 2%, 3, 4, 5, 10, 15, 20, 25, 30, 35, 40, 45, 50, 55, 60, 65, 70, 75, 80, 85, 90, 91, 92, 93, 94, 95, 96, 97, 98, 99, 99.5, 99.9, 99.99, or about 99.999% or more.

The coating can be sufficient to provide any suitable weight gain to the solid material, such that the antioxidant is suitably applied to the solid material. For example, the coating can be sufficient to provide a weight gain of about 0.000.01 g per cm$^2$ surface area of the solid material to about 0.1 g/cm$^2$ surface area, about 0.000.1 g/cm$^2$ surface area to about 0.1 g/cm$^2$ surface area, about 0.000.01 g/cm$^2$ surface area or less, or about 0.000.1 g/cm$^2$ surface area, 0.000.2, 0.000.5, 0.000.8, 0.001, 0.005, 0.01, 0.05, or about 0.1 g/cm$^2$ surface area or more.

The liquid including the antioxidant can be any suitable composition. The liquid can include any suitable optional component in addition to the antioxidant. The liquid can include one antioxidant, or multiple antioxidants. The liquid can include no carrier fluid, one carrier fluid, or multiple carrier fluids. The carrier liquid can be any suitable carrier liquid. The carrier liquid can be water (e.g., di-ionized water), or an aqueous solution (e.g., saline). The carrier liquid can be an organic solvent, such as any suitable organic solvent, such as acetone, methanol, ethanol, or propanol (e.g., isopropanol or normal propanol). The carrier liquid, if present, can be any suitable proportion of the liquid including the antioxidant, such as about 1 wt % to about 99 wt %, 5 wt % to about 95 wt %, or about 1 wt % or less, or about 2 wt %, 3, 4, 5, 10, 15, 20, 25, 30, 35, 40, 45, 50, 55, 60, 65, 70, 75, 80, 85, 90, 91, 92, 93, 94, 95, 96, 97, 98, or about 99 wt % or more.

The antioxidant can be any suitable antioxidant that allows the method to effectively produce melt-stabilized materials including UHMWPE having less or no oxidized layer when melt-stabilized in an oxygen-containing environment. The antioxidant can be a suitable free-radical scavenger, such that the antioxidant neutralizes a free-radical before it can react with oxygen to form an oxidized species. The antioxidant or the multiple antioxidants can be any suitable wt % of the liquid composition, such as about 0.01 wt % to about 100 wt % of the liquid composition, about 5 wt % to about 100 wt %, about 0.01 wt % or less, or about 0.1 wt %, 1, 2, 3, 4, 5, 6, 7, 8, 9, 10, 15, 20, 25, 30, 35, 40, 45, 50, 55, 60, 65, 70, 75, 80, 85, 90, 91, 92, 93, 94, 95, 96, 97, 98, 99, 99.5, 99.9, 99.99, or about 99.999 wt % of the composition or more.

In various embodiments, the antioxidant can be at least one of a tocopherol, a tocopherol phosphite (a tocopherol including a phosphite protecting group), a tocotrienol, vitamin E, vitamin E acetate, Irganox® 1010 (pentaerythritol tetrakis(3-(3,5-di-tert-butyl-4-hydroxyphenyl)propionate)), Tinuvin® 622 LD (butanedioic acid dimethyl ester/4-hydroxy-2,2,6,6-tetramethyl-1-piperidine ethanol copolymer), tannic acid, bilberry extract, vitamin C (e.g., ascorbyl palmitate or other lipid soluble forms), a carotene (e.g., vitamin A, lycopene), a flavonoid (e.g., flavonol), an isoflavonoid, a neoflavonoid, a lignin (e.g., enterodiol), quinine, ubiquinone (e.g., coenzyme Q10), vitamin K1, a metal (e.g., selenium), glutathione, propyl gallate, octyl gallate, lauryl gallate, resveratrol, rosmarinic acid, rutin, 5-aminosalicylic acid, butylated hydroxy anisole (BHA), butylated hydroxy toluene (BHT), a phenolic compound (e.g., t-butyl hydroquinone), and a monomeric or polymeric hindered amine stabilizer (e.g., derivatives of 2,2,6,6-tetramethylpiperidine). In some embodiments, the antioxidant can be at least one of vitamin E, vitamin E acetate, vitamin E phosphite (vitamin E including a phosphite protecting group), pentaerythritoltetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, rosemary oil, and bilberry extract. In various embodiments, vitamin E phosphite or a tocopherol phosphite can be used, as described in U.S. Pat. No. 8,399,535, which can be deprotected to provide vitamin E or a tocopherol, respectively, using a suitable deprotection means, such as hydrolysis (e.g., exposure to water with optional acid or base).

As used herein, "vitamin E" (e.g., alone or as a derivative such as vitamin E acetate) can refer to at least one of racemic alpha-tocopherol, RRR-alpha-tocopherol, SRR-alpha-tocopherol, SSR-alpha-tocopherol, SRS-alpha-tocopherol, SSS-alpha-tocopherol, RSR-alpha-tocopherol, RRS-alpha-tocopherol, RSS-alpha-tocopherol, racemic beta-tocopherol, RRR-beta-tocopherol, SRR-beta-tocopherol, SSR-beta-tocopherol, SRS-beta-tocopherol, SSS-beta-tocopherol, RSR-beta-tocopherol, RRS-beta-tocopherol, RSS-beta-tocopherol, racemic gamma-tocopherol, RRR-gamma-tocopherol, SRR-gamma-tocopherol, SSR-gamma-tocopherol, SRS-gamma-tocopherol, SSS-gamma-tocopherol, RSR-gamma-tocopherol, RRS-gamma-tocopherol, RSS-gamma-tocopherol, racemic delta-tocopherol, RRR-delta-tocopherol, SRR-delta-tocopherol, SSR-delta-tocopherol, SRS-delta-tocopherol, SSS-delta-tocopherol, RSR-delta-tocopherol, RRS-delta-tocopherol, and RSS-delta-tocopherol.

A tocopherol can have the structure:

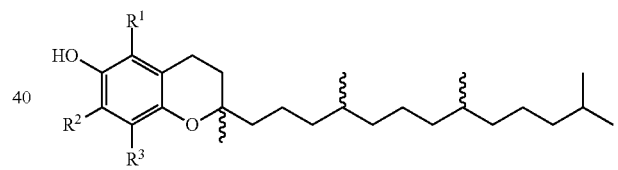

wherein $R^1$, $R^2$, and $R^3$ are each independently selected from hydrogen, substituted or unsubstituted $(C_1-C_{10})$alkyl, and substituted or unsubstituted $(C_1-C_{10})$alkenyl. The stereochemistry of the tocopherol can be racemic or at least one of RRR, SRR, SSR, SRS, RSR, RRS, RSS, and SSS. In some embodiments, $R^1$, $R^2$, and $R^3$ are each $(C_1-C_{10})$alkyl, such as methyl (e.g., alpha-tocopherol). In some embodiments, $R^1$ and $R^3$ are each $(C_1-C_{10})$alkyl, such as methyl, and $R^2$ is hydrogen (beta-tocopherol). In some embodiments, $R^2$ and $R^3$ are each $(C_1-C_{10})$alkyl, such as methyl, and $R^1$ is hydrogen (gamma-tocopherol). In some embodiments, $R^1$ and $R^2$ are each hydrogen and $R^3$ is $(C_1-C_{10})$alkyl, such as methyl (delta-tocopherol).

A tocotrienol can have the structure:

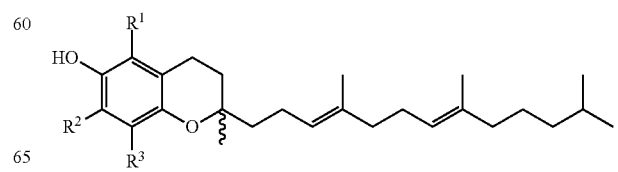

wherein $R^1$, $R^2$, and $R^3$ are each independently selected from hydrogen, substituted or unsubstituted ($C_1$-$C_{10}$)alkyl, and substituted or unsubstituted ($C_1$-$C_{10}$)alkenyl. The stereochemistry of the tocotrienol can be racemic or at least one of R and S. In some embodiments, $R^1$, $R^2$, and $R^3$ are each ($C_1$-$C_{10}$)alkyl, such as methyl (e.g., alpha-tocotrienol). In some embodiments, $R^1$ and $R^3$ are each ($C_1$-$C_{10}$)alkyl, such as methyl, and $R^2$ is hydrogen (beta-tocotrienol). In some embodiments, $R^2$ and $R^3$ are each ($C_1$-$C_{10}$)alkyl, such as methyl, and $R^1$ is hydrogen (gamma-tocotrienol). In some embodiments, $R^1$ and $R^2$ are each hydrogen and $R^3$ is ($C_1$-$C_{10}$)alkyl, such as methyl (delta-tocotrienol). A tocopherol or tocotrienol can be naturally occurring or synthetic.
Heating.

The method can include heating the coated solid material in an environment comprising oxygen, the heating sufficient to melt at least part of the UHMWPE, to provide a heated material. The heating can melt any suitable amount of the coated solid material, or of the UHMWPE in the coated solid material, such as about 1 vol % to about 100 vol %, or about 1 vol % or less, or about 2 vol %, 3, 4, 5, 6, 7, 8, 9, 10, 15, 20, 25, 30, 35, 40, 45, 50, 55, 60, 65, 70, 75, 80, 85, 90, 95, 96, 97, 98, or about 99 vol % or more. The heating is sufficient to melt-stabilize the coated solid material, such that at least some of the free radicals in the coated solid material (e.g., free radicals in the UHMWPE) can recombine or otherwise be neutralized.

The heating can occur in an environment including any suitable amount of oxygen. For example, the heating can occur in an environment including ambient air, having about 20-21 vol % oxygen. The heating can occur in an environment having about 1 vol % to about 50 vol % oxygen, about 10 vol % to about 30 vol % oxygen, about 1 vol % oxygen or less, or about 2 vol %, 3, 4, 5, 6, 8, 10, 12, 14, 16, 18, 20, 22, 24, 26, 28, 30, 32, 34, 36, 38, 40, 42, 44, 46, 48, or about 50 vol % oxygen or more.

The heating heats the coated solid material to any suitable temperature, such as about 100° C. to about 400° C., about 140° C. to about 160° C., about 100° C. or less, or about 110° C., 120, 130, 140, 150, 160, 170, 180, 190, 200, 220, 240, 260, 280, 300, 320, 340, 360, 380, or about 400° C. or more. The coated solid material can be heated for any suitable duration, such as about 1 minute to about 7 days, or about 1 hour to about 48 hours, or about 1 minute or less, or about 2 minutes, 3, 4, 5, 10, 15, 20, 25, 30, 35, 40, 45, 50, 55 minutes, 1 hour, 1.5, 2, 2.5, 3, 3.5, 4, 4.5, 5, 6, 7, 8, 9, 10, 11, 12, 13, 14, 15, 16, 17, 18, 19, 20, 21, 22, 23 hours, 1 day, 1.5, 2, 2.5, 3, 3.5, 4, 4.5, 5, 5.5, 6, 6.5 days, or about 7 days or more.
Solidifying.

The method can include solidifying the heated material, to provide a melt-stabilized material comprising UHMWPE comprising a second concentration of free-radicals, wherein the second concentration of free-radicals is less than the first concentration of free-radicals. The solidifying can be any suitable solidifying, such that the melted material is allowed to solidify. The solidifying can include allowing the heated material to cool to a temperature below the melting point of the heated material, such as to room temperature. The solidifying can occur in ambient conditions, or the solidifying can occur in a chilled environment. The solidifying can occur in any medium, such as in a gas (e.g., air,) or in a liquid (e.g., water).
Melt-stabilized Material and Medical Implant Including the Same.

In various embodiments, the present invention provides a melt-stabilized material made by any suitable embodiment of a method described herein. For example, in various embodiments, the present invention provides an oxygen-containing-environment-melt-stabilized material comprising UHMWPE, the melt-stabilized material being free of post-melt-stabilization oxidized surface layer removal greater than about 1 mm depth, 1.5, 2, 2.5, 3, 3.5, 4, 4.5, 5, 5.5, or greater than about 6 mm depth, wherein the UHMWPE in a surface layer of the melt-stabilized material has an oxidation index that does not exceed 1.

In some embodiments, the present invention provides a medical implant that includes any suitable embodiment of a melt stabilized material made by an embodiment of a method described herein. A method of making the melt-stabilized material can include generating a medical implant from the material, such that the method is a method of making a medical implant. In some embodiments, various amounts of the surface of the melt-stabilized material can be removed during processing and machining the material into the desired shape for the implant, such as about 0 mm to about 1 mm, about 0 mm to about 5 mm, about 0 mm to about 10 mm, about 0.1 mm or less, or about 0.5 mm, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 mm or more. In some embodiments, the medical implant can be an orthopedic implant. In various embodiments, the medical implant can form or be part of an artificial hip, hip liner, knee, knee liner, disk replacement, shoulder, elbow, foot, ankle, finger, mandible, or bearings in an artificial heart.

EXAMPLES

Various embodiments of the present invention can be better understood by reference to the following Examples which are offered by way of illustration. The present invention is not limited to the Examples given herein.

Example 1

Preparation of Samples

Ticona GUR® 1050 UHMWPE powder was compression molded into 1.75 inch thick nominal slabs that were 8.75× 10.5 inch, width×length, and then quarter sectioned into 4.3×5.2×1.75 inch blocks.

Example 2

Irradiation of Samples

Blocks from Example 1 were double vacuum packaged in foil lined bags with nitrogen purging to eliminate oxygen from the package, and then gamma irradiated to about 90 kGy under the low oxygen environment (about 0.5 vol % $O_2$).

Example 3a

Melt-Stabilization with No Irradiation

A block from Example 1 was melt-stabilized by heating to 150° C. for 14 hours.

Example 3b

Melt-stabilization with No Antioxidant Treatment

A block from Example 2 was melt-stabilized by heating to 150° C. for 14 hours, which is above the irradiated UHMWPE melting point of about 138° C. as determined by DSC analysis.

Examples 4a-f

Melt-stabilization with Antioxidant Treatment (Vitamin E)

One block from Example 2 was treated by wiping the exterior of the block with a paper towel saturated with a) neat vitamin E (all racemic D,L-α-tocopherol), and one block each was similarly wiped with the following solution ratios of parts by weight vitamin E and parts by weight isopropanol respectively: b) 75:25; c) 50:50; d) 25:75; e) 10:90; f) 5:95. The blocks were then melt-stabilized by heating to 150° C. for 14 hours.

Examples 5a-c

Melt-stabilization with Antioxidant Treatment (Various)

One block from Example 2 was sectioned into quarters. Each quarter was then treated with the following solutions by wiping the exterior surfaces with a saturated paper towel: (a) 40% by weight Irganox® 1010 (pentaerythritol tetrakis (3-(3,5-di-tert-butyl-4-hydroxyphenyl)propionate)) dissolved in acetone; (b) 33% by weight Tinuvin® 622LD (butanedioic acid dimethyl ester/4-hydroxy-2,2,6,6-tetramethyl-1-piperidine ethanol copolymer) dissolved in dichloromethane; (c) 20% by weight tannic acid (2,3-dihydroxy-5-({[(2R,3R,4S,5R,6R)-3,4,5,6-tetrakis({3,4-dihydroxy-5-[(3,4,5-trihydroxyphenyl)carbonyloxy]phenyl}carbonyloxy)oxan-2-yl]methoxy}carbonyl)phenyl 3,4,5-trihydroxybenzoate) dissolved in de-ionized water; (d) 20% by weight bilberry extract (fresh freeze-dried bilberry powder from Eclectic Institute, having about 130 mg of anthcyanins per 3 grams of bilberry extract powder) dissolved in de-ionized water. The blocks were then melt-stabilized by heating to 150° C. for 14 hours.

Examples 6a-d

Melt-stabilization with Antioxidant Treatment (Vitamin E)

One half of a block from Example 2 was sectioned into quarters. One quarter section was then treated with the following solutions by wiping the exterior surfaces with a saturated paper towel: (a) Control, no treatment; (b) vitamin E, neat; (c) 25% by weight vitamin E dissolved in isopropanol; (d) vitamin E acetate, neat, wherein the vitamin E and vitamin E acetate were all racemic D,L-α-tocopherol. The blocks were then melt-stabilized by heating to 150° C. for 14 hours.

Example 7

Oxidation Index

Oxidation levels were determined through the blocks at center from top to bottom and side to side of each block, bottom denoting the surface the block was setting on during the melt stabilization process. The FTIR Oxidation Index (OI) was determined per ASTM F2102-06. Following the ASTM F2102-06 protocol, 100-200 micron thick films were microtomed from the block of material, with the top indicative of the initial incident irradiation face. The film was scanned with an FTIR spectrophotometer using an indexing microscopic attachment to obtain infrared spectra at 200 micron intervals across the entire length of the film. The oxidation index at various locations scanned was then calculated using the ratio of the oxidation peak (1765-1680 $cm^{-1}$, centered at 1720 $cm^{-1}$) to a control peak that does not change with irradiation (1392-1330 $cm^{-1}$, centered at 1370 $cm^{-1}$). Table 1 gives data from the surface to a depth where the OI decreases to below 0.1, given for each face in the materials from Examples 1 and 3-6.

TABLE 1

| | | | FTIR data oxidation index (OI). VE is vitamin E. | | | | |
|---|---|---|---|---|---|---|---|
| No. | Depth (μm) | Top OI | Bottom OI | Side 1 OI | Side 2 OI | Treatment | FIGS. |
| 1 | 0 | −0.0273 | −0.0407 | — | — | as-molded | 1a-b |
| | 200 | −0.0350 | −0.0329 | — | — | as-molded | |
| | 400 | −0.0637 | −0.0551 | — | — | as-molded | |
| | 600 | −0.0310 | −0.0255 | — | — | as-molded | |
| | 800 | −0.0347 | −0.0314 | — | — | as-molded | |
| | 1000 | −0.0305 | −0.0326 | — | — | as-molded | |
| | 1200 | −0.0393 | −0.0410 | — | — | as-molded | |
| | 1400 | −0.0234 | −0.0415 | — | — | as-molded | |
| | 1600 | −0.0386 | −0.0376 | — | — | as-molded | |
| 3a | 0 | 1.0556 | 2.8864 | — | — | as-molded, melt stabilized | 2a-b |
| | 200 | 0.3736 | 0.5774 | — | — | as-molded, melt stabilized | |
| | 400 | 0.2357 | 0.2380 | — | — | as-molded, melt stabilized | |
| | 600 | 0.1602 | 0.1536 | — | — | as-molded, melt stabilized | |
| | 800 | 0.1585 | 0.1201 | — | — | as-molded, melt stabilized | |
| | 1000 | 0.1207 | 0.1023 | — | — | as-molded, melt stabilized | |
| | 1200 | 0.1120 | 0.0901 | — | — | as-molded, melt stabilized | |
| | 1400 | 0.1027 | 0.0765 | — | — | as-molded, melt stabilized | |
| | 1600 | 0.0931 | 0.0980 | — | — | as-molded, melt stabilized | |
| 3b | 0 | 1.1943 | 7.5130 | 3.0618 | 1.8762 | melt stabilized gamma control | 3a-f |
| | 200 | 0.4420 | 1.8610 | 0.8719 | 0.5869 | melt stabilized gamma control | |
| | 400 | 0.2726 | 0.5850 | 0.3102 | 0.2587 | melt stabilized gamma control | |
| | 600 | 0.1594 | 0.2773 | 0.1690 | 0.1732 | melt stabilized gamma control | |

TABLE 1-continued

FTIR data oxidation index (OI). VE is vitamin E.

| No. | Depth (μm) | Top OI | Bottom OI | Side 1 OI | Side 2 OI | Treatment | FIGS. |
|---|---|---|---|---|---|---|---|
| | 800 | 0.1170 | 0.1552 | 0.1274 | 0.1247 | melt stabilized gamma control | |
| | 1000 | 0.0879 | 0.1266 | 0.1085 | 0.1176 | melt stabilized gamma control | |
| | 1200 | 0.0729 | 0.1038 | 0.0995 | 0.0992 | melt stabilized gamma control | |
| | 1400 | 0.0726 | 0.1016 | 0.0892 | 0.0868 | melt stabilized gamma control | |
| | 1600 | 0.0612 | 0.0873 | 0.0843 | 0.0855 | melt stabilized gamma control | |
| 4a | 0 | 0.0470 | 0.0423 | 0.0624 | 0.0486 | neat vitamin E | 4a-f |
| | 200 | 0.0469 | 0.0341 | 0.0459 | 0.0341 | neat vitamin E | |
| | 400 | 0.0314 | 0.0232 | 0.0292 | 0.0216 | neat vitamin E | |
| | 600 | 0.0201 | 0.0168 | 0.0175 | 0.0136 | neat vitamin E | |
| | 800 | 0.0142 | 0.0124 | 0.0114 | 0.0086 | neat vitamin E | |
| | 1000 | 0.0094 | 0.0108 | 0.0077 | 0.0061 | neat vitamin E | |
| | 1200 | 0.0074 | 0.0097 | 0.0056 | 0.0053 | neat vitamin E | |
| | 1400 | 0.0066 | 0.0090 | 0.0043 | 0.0050 | neat vitamin E | |
| | 1600 | 0.0068 | 0.0076 | 0.0038 | 0.0049 | neat vitamin E | |
| 4c | 0 | 0.0496 | 0.0518 | 0.0516 | 0.0528 | 50% vitamin E | 5a-f |
| | 200 | 0.0409 | 0.0392 | 0.0396 | 0.0492 | 50% vitamin E | |
| | 400 | 0.0248 | 0.0271 | 0.0249 | 0.0355 | 50% vitamin E | |
| | 600 | 0.0150 | 0.0174 | 0.0154 | 0.0220 | 50% vitamin E | |
| | 800 | 0.0099 | 0.0135 | 0.0112 | 0.0151 | 50% vitamin E | |
| | 1000 | 0.0070 | 0.0104 | 0.0086 | 0.0118 | 50% vitamin E | |
| | 1200 | 0.0050 | 0.0091 | 0.0069 | 0.0101 | 50% vitamin E | |
| | 1400 | 0.0037 | 0.0058 | 0.0038 | 0.0086 | 50% vitamin E | |
| | 1600 | 0.0034 | 0.0061 | 0.0053 | 0.0064 | 50% vitamin E | |
| 4d | 0 | 0.0502 | 0.0464 | 0.0546 | 0.0616 | 25% vitamin E | 6a-f |
| | 200 | 0.0374 | 0.0315 | 0.0444 | 0.0424 | 25% vitamin E | |
| | 400 | 0.0241 | 0.0196 | 0.0342 | 0.0243 | 25% vitamin E | |
| | 600 | 0.0144 | 0.0105 | 0.0205 | 0.0163 | 25% vitamin E | |
| | 800 | 0.0105 | 0.0088 | 0.0122 | 0.0123 | 25% vitamin E | |
| | 1000 | 0.0079 | 0.0061 | 0.0081 | 0.0095 | 25% vitamin E | |
| | 1200 | 0.0059 | 0.0043 | 0.0059 | 0.0064 | 25% vitamin E | |
| | 1400 | 0.0053 | 0.0035 | 0.0052 | 0.0058 | 25% vitamin E | |
| | 1600 | 0.0038 | 0.0030 | 0.0038 | 0.0043 | 25% vitamin E | |
| 4e | 0 | 0.0573 | 0.0554 | 0.0574 | 0.0540 | 10% vitamin E | 7a-f |
| | 200 | 0.0457 | 0.0417 | 0.0507 | 0.0453 | 10% vitamin E | |
| | 400 | 0.0321 | 0.0281 | 0.0325 | 0.0357 | 10% vitamin E | |
| | 600 | 0.0185 | 0.0195 | 0.0188 | 0.0265 | 10% vitamin E | |
| | 800 | 0.0121 | 0.0141 | 0.0125 | 0.0210 | 10% vitamin E | |
| | 1000 | 0.0077 | 0.0125 | 0.0105 | 0.0177 | 10% vitamin E | |
| | 1200 | 0.0066 | 0.0105 | 0.0075 | 0.0150 | 10% vitamin E | |
| | 1400 | 0.0032 | 0.0099 | 0.0051 | 0.0127 | 10% vitamin E | |
| | 1600 | 0.0006 | 0.0081 | 0.0048 | 0.0121 | 10% vitamin E | |
| 4f | 0 | 2.5615 | 0.3771 | 1.3418 | 3.5155 | 5% vitamin E | 8a-f |
| | 200 | 1.3597 | 0.1337 | 0.3616 | 1.6612 | 5% vitamin E | |
| | 400 | 0.5724 | 0.0939 | 0.1253 | 0.5737 | 5% vitamin E | |
| | 600 | 0.2301 | 0.0481 | 0.0641 | 0.2012 | 5% vitamin E | |
| | 800 | 0.0929 | 0.0412 | 0.0398 | 0.0932 | 5% vitamin E | |
| | 1000 | 0.0458 | 0.0341 | 0.0323 | 0.0474 | 5% vitamin E | |
| | 1200 | 0.0242 | 0.0262 | 0.0255 | 0.0305 | 5% vitamin E | |
| | 1400 | 0.0207 | 0.0199 | 0.0210 | 0.0227 | 5% vitamin E | |
| | 1600 | 0.0140 | 0.0180 | 0.0191 | 0.0179 | 5% vitamin E | |
| 5a | 0 | 0.2912 | 0.3379 | 0.2745 | 0.3693 | 40% Irganox ® 1010 | 9a-f |
| | 200 | 0.2825 | 0.3262 | 0.2589 | 0.3607 | 40% Irganox ® 1010 | |
| | 400 | 0.2822 | 0.2955 | 0.2393 | 0.3483 | 40% Irganox ® 1010 | |
| | 600 | 0.2916 | 0.2717 | 0.2265 | 0.3148 | 40% Irganox ® 1010 | |
| | 800 | 0.2534 | 0.2359 | 0.2267 | 0.2638 | 40% Irganox ® 1010 | |
| | 1000 | 0.2165 | 0.2168 | 0.2179 | 0.2264 | 40% Irganox ® 1010 | |
| | 1200 | 0.1811 | 0.1940 | 0.1756 | 0.2129 | 40% Irganox ® 1010 | |
| | 1400 | 0.1704 | 0.1681 | 0.1565 | 0.1804 | 40% Irganox ® 1010 | |
| | 1600 | 0.1551 | 0.1465 | 0.1434 | 0.2029 | 40% Irganox ® 1010 | |
| | 1800 | 0.1531 | 0.1372 | 0.1554 | 0.1794 | 40% Irganox ® 1010 | |
| | 2000 | 0.1339 | 0.1208 | 0.1525 | 0.1445 | 40% Irganox ® 1010 | |
| | 2200 | 0.1274 | 0.1113 | 0.1218 | 0.1152 | 40% Irganox ® 1010 | |
| | 2400 | 0.1092 | 0.0937 | 0.0894 | 0.0904 | 40% Irganox ® 1010 | |
| | 2600 | 0.1102 | 0.0945 | 0.0692 | 0.0723 | 40% Irganox ® 1010 | |
| | 2800 | 0.0696 | 0.1042 | 0.0578 | 0.0640 | 40% Irganox ® 1010 | |
| | 3000 | 0.0546 | 0.0902 | 0.0481 | 0.0436 | 40% Irganox ® 1010 | |
| | 3200 | 0.0497 | 0.0961 | 0.0451 | 0.0311 | 40% Irganox ® 1010 | |
| | 3400 | 0.0360 | 0.0736 | 0.0468 | 0.0223 | 40% Irganox ® 1010 | |
| | 3600 | 0.0344 | 0.0498 | 0.0423 | 0.0259 | 40% Irganox ® 1010 | |
| | 3800 | 0.0347 | 0.0396 | 0.0331 | 0.0208 | 40% Irganox ® 1010 | |
| | 4000 | 0.0200 | 0.0330 | 0.0273 | 0.0141 | 40% Irganox ® 1010 | |
| | 4200 | 0.0170 | 0.0219 | 0.0175 | 0.0095 | 40% Irganox ® 1010 | |
| | 4400 | 0.0152 | 0.0210 | 0.0075 | 0.0089 | 40% Irganox ® 1010 | |

TABLE 1-continued

FTIR data oxidation index (OI). VE is vitamin E.

| No. | Depth (μm) | Top OI | Bottom OI | Side 1 OI | Side 2 OI | Treatment | FIGS. |
|---|---|---|---|---|---|---|---|
| | 4600 | 0.0129 | 0.0212 | 0.0064 | −0.0003 | 40% Irganox ® 1010 | |
| | 4800 | 0.0962 | 0.0213 | 0.0035 | 0.0038 | 40% Irganox ® 1010 | |
| | 5000 | 0.0009 | 0.0186 | −0.0011 | 0.0020 | 40% Irganox ® 1010 | |
| 5b | 0 | 0.2454 | 0.0891 | 0.5180 | 0.2539 | 33% Tinuvin ® 622 LD | 10a-f |
| | 200 | 0.2230 | 0.0763 | 0.2061 | 0.1561 | 33% Tinuvin ® 622 LD | |
| | 400 | 0.0969 | 0.0755 | 0.1215 | 0.1335 | 33% Tinuvin ® 622 LD | |
| | 600 | 0.0683 | 0.0549 | 0.1187 | 0.0955 | 33% Tinuvin ® 622 LD | |
| | 800 | 0.0887 | 0.0542 | 0.1597 | 0.1813 | 33% Tinuvin ® 622 LD | |
| | 1000 | 0.0781 | 0.0625 | 0.1251 | 0.2039 | 33% Tinuvin ® 622 LD | |
| | 1200 | 0.0978 | 0.0564 | 0.0970 | 0.2865 | 33% Tinuvin ® 622 LD | |
| | 1400 | 0.0735 | 0.0769 | 0.1106 | 0.8192 | 33% Tinuvin ® 622 LD | |
| | 1600 | 0.1291 | 0.1169 | 0.0960 | 0.0976 | 33% Tinuvin ® 622 LD | |
| | 1800 | 0.1322 | 2.2416 | 0.6927 | 0.0248 | 33% Tinuvin ® 622 LD | |
| | 2000 | 0.3524 | 0.0590 | 0.3119 | 0.0145 | 33% Tinuvin ® 622 LD | |
| | 2200 | 0.0763 | 0.0131 | 0.1168 | 0.0126 | 33% Tinuvin ® 622 LD | |
| | 2400 | 0.0166 | 0.0100 | 0.0430 | 0.0082 | 33% Tinuvin ® 622 LD | |
| | 2600 | 0.0019 | 0.0092 | 0.0409 | 0.0098 | 33% Tinuvin ® 622 LD | |
| | 2800 | 0.0032 | 0.0046 | 0.0291 | 0.0484 | 33% Tinuvin ® 622 LD | |
| | 3000 | 0.0011 | 0.0054 | 0.0228 | 0.0093 | 33% Tinuvin ® 622 LD | |
| | 3200 | 0.0059 | 0.0050 | 0.0189 | 0.0100 | 33% Tinuvin ® 622 LD | |
| | 3400 | 0.0039 | 0.0037 | 0.0221 | 0.0063 | 33% Tinuvin ® 622 LD | |
| | 3600 | −0.0007 | 0.0028 | 0.0220 | 0.0083 | 33% Tinuvin ® 622 LD | |
| | 3800 | −0.0026 | 0.0040 | 0.0355 | 0.0079 | 33% Tinuvin ® 622 LD | |
| | 4000 | −0.0035 | −0.0015 | 0.0350 | 0.0066 | 33% Tinuvin ® 622 LD | |
| 5c | 0 | 2.8956 | 0.1039 | 1.0009 | 2.0181 | 20% tannic acid | 11a-f |
| | 200 | 0.7501 | 0.0957 | 0.3616 | 1.0582 | 20% tannic acid | |
| | 400 | 0.3036 | 0.0881 | 0.2061 | 0.3974 | 20% tannic acid | |
| | 600 | 0.1763 | 0.0812 | 0.1421 | 0.1987 | 20% tannic acid | |
| | 800 | 0.1262 | 0.0722 | 0.1259 | 0.1347 | 20% tannic acid | |
| | 1000 | 0.1094 | 0.0659 | 0.1045 | 0.1052 | 20% tannic acid | |
| | 1200 | 0.0830 | 0.0599 | 0.0902 | 0.0925 | 20% tannic acid | |
| | 1400 | 0.0768 | 0.0561 | 0.0876 | 0.0820 | 20% tannic acid | |
| | 1600 | 0.0698 | 0.0526 | 0.0821 | 0.0746 | 20% tannic acid | |
| | 1800 | 0.0664 | 0.0490 | 0.0814 | 0.0656 | 20% tannic acid | |
| | 2000 | 0.0652 | 0.0475 | 0.0737 | 0.0588 | 20% tannic acid | |
| | 2200 | 0.0567 | 0.0397 | 0.0644 | 0.0524 | 20% tannic acid | |
| | 2400 | 0.0476 | 0.0382 | 0.0555 | 0.0489 | 20% tannic acid | |
| | 2600 | 0.0538 | 0.0361 | 0.0572 | 0.0452 | 20% tannic acid | |
| | 2800 | 0.0420 | 0.0326 | 0.0554 | 0.0392 | 20% tannic acid | |
| | 3000 | 0.0391 | 0.0265 | 0.0459 | 0.0348 | 20% tannic acid | |
| | 3200 | 0.0353 | 0.0301 | 0.0384 | 0.0326 | 20% tannic acid | |
| | 3400 | 0.0378 | 0.0261 | 0.0438 | 0.0297 | 20% tannic acid | |
| | 3600 | 0.0305 | 0.0224 | 0.0398 | 0.0285 | 20% tannic acid | |
| | 3800 | 0.0272 | 0.0204 | 0.0332 | 0.0254 | 20% tannic acid | |
| | 4000 | 0.0231 | 0.0177 | 0.0299 | 0.0223 | 20% tannic acid | |
| | 4200 | 0.0258 | 0.0173 | 0.0220 | 0.0172 | 20% tannic acid | |
| | 4400 | 0.0200 | 0.0200 | 0.0238 | 0.0137 | 20% tannic acid | |
| | 4600 | 0.0190 | 0.0153 | 0.0167 | 0.0119 | 20% tannic acid | |
| | 4800 | 0.0142 | 0.0146 | 0.0170 | 0.0121 | 20% tannic acid | |
| | 5000 | 0.0123 | 0.0163 | 0.0150 | 0.0086 | 20% tannic acid | |
| 5d | 0 | 1.9041 | 2.0875 | 3.2816 | 2.1536 | 20% bilberry extract | 12a-f |
| | 200 | 0.5650 | 0.9137 | 0.7882 | 0.5717 | 20% bilberry extract | |
| | 400 | 0.2568 | 0.4284 | 0.3170 | 0.2559 | 20% bilberry extract | |
| | 600 | 0.1644 | 0.2647 | 0.2014 | 0.1552 | 20% bilberry extract | |
| | 800 | 0.1298 | 0.2093 | 0.1606 | 0.1273 | 20% bilberry extract | |
| | 1000 | 0.1172 | 0.1803 | 0.1325 | 0.1166 | 20% bilberry extract | |
| | 1200 | 0.1040 | 0.1620 | 0.1169 | 0.1034 | 20% bilberry extract | |
| | 1400 | 0.0933 | 0.1467 | 0.1072 | 0.0916 | 20% bilberry extract | |
| | 1600 | 0.0902 | 0.1352 | 0.0907 | 0.0873 | 20% bilberry extract | |
| | 1800 | 0.0833 | 0.1257 | 0.0942 | 0.0769 | 20% bilberry extract | |
| | 2000 | 0.0778 | 0.1177 | 0.0891 | 0.0714 | 20% bilberry extract | |
| | 2200 | 0.0741 | 0.1077 | 0.0806 | 0.0663 | 20% bilberry extract | |
| | 2400 | 0.0661 | 0.1031 | 0.0711 | 0.0610 | 20% bilberry extract | |
| | 2600 | 0.0634 | 0.0950 | 0.0649 | 0.0523 | 20% bilberry extract | |
| | 2800 | 0.0592 | 0.0835 | 0.0639 | 0.0488 | 20% bilberry extract | |
| | 3000 | 0.0518 | 0.0787 | 0.0472 | 0.0456 | 20% bilberry extract | |
| | 3200 | 0.0502 | 0.0705 | 0.0443 | 0.0455 | 20% bilberry extract | |
| | 3400 | 0.0471 | 0.0639 | 0.0361 | 0.0351 | 20% bilberry extract | |
| | 3600 | 0.0406 | 0.0584 | 0.0441 | 0.0350 | 20% bilberry extract | |
| | 3800 | 0.0356 | 0.0544 | 0.0378 | 0.0281 | 20% bilberry extract | |
| | 4000 | 0.0335 | 0.0509 | 0.0311 | 0.0281 | 20% bilberry extract | |
| | 4200 | 0.0301 | 0.0482 | 0.0355 | 0.0222 | 20% bilberry extract | |
| | 4400 | 0.0307 | 0.0396 | 0.0188 | 0.0192 | 20% bilberry extract | |
| | 4600 | 0.0259 | 0.0404 | 0.0234 | 0.0189 | 20% bilberry extract | |

TABLE 1-continued

FTIR data oxidation index (OI). VE is vitamin E.

| No. | Depth (μm) | Top OI | Bottom OI | Side 1 OI | Side 2 OI | Treatment | FIGS. |
|---|---|---|---|---|---|---|---|
|  | 4800 | 0.0235 | 0.0351 | 0.0233 | 0.0164 | 20% bilberry extract |  |
|  | 5000 | 0.0233 | 0.0352 | 0.0239 | 0.0121 | 20% bilberry extract |  |
| 6a | 0 | 4.6042 | 2.5503 | 2.8320 | 0.8326 | melt stabilized gamma control | 13a-d |
|  | 200 | 1.0881 | 0.6840 | 0.7344 | 0.2703 | melt stabilized gamma control |  |
|  | 400 | 0.3657 | 0.3027 | 0.3305 | 0.1248 | melt stabilized gamma control |  |
|  | 600 | 0.1936 | 0.1657 | 0.1605 | 0.0699 | melt stabilized gamma control |  |
|  | 800 | 0.1197 | 0.1073 | 0.1166 | 0.0554 | melt stabilized gamma control |  |
|  | 1000 | 0.0897 | 0.0844 | 0.0892 | 0.0408 | melt stabilized gamma control |  |
|  | 1200 | 0.0822 | 0.0677 | 0.0769 | 0.0303 | melt stabilized gamma control |  |
|  | 1400 | 0.0672 | 0.0683 | 0.0667 | 0.0328 | melt stabilized gamma control |  |
|  | 1600 | 0.0647 | 0.0679 | 0.0604 | 0.0226 | melt stabilized gamma control |  |
| 6b | 0 | 0.0319 | 0.0199 | 0.0403 | 0.0050 | neat vitamin E | 14a-d |
|  | 200 | 0.0300 | 0.0116 | 0.0219 | 0.0015 | neat vitamin E |  |
|  | 400 | 0.0180 | 0.0067 | 0.0116 | −0.0023 | neat vitamin E |  |
|  | 600 | 0.0129 | 0.0061 | 0.0099 | −0.0034 | neat vitamin E |  |
|  | 800 | 0.0105 | 0.0022 | 0.0017 | −0.0050 | neat vitamin E |  |
|  | 1000 | 0.0078 | 0.0018 | 0.0034 | −0.0050 | neat vitamin E |  |
|  | 1200 | 0.0032 | 0.0000 | 0.0030 | −0.0071 | neat vitamin E |  |
|  | 1400 | 0.0045 | −0.0050 | 0.0021 | 0.0003 | neat vitamin E |  |
|  | 1600 | 0.0024 | 0.0068 | 0.0033 | −0.0034 | neat vitamin E |  |
| 6c | 0 | 0.0494 | 0.0303 | 0.0487 | 0.0174 | 25% vitamin E | 15a-d |
|  | 200 | 0.0378 | 0.0221 | 0.0480 | 0.0154 | 25% vitamin E |  |
|  | 400 | 0.0196 | 0.0200 | 0.0285 | 0.0069 | 25% vitamin E |  |
|  | 600 | 0.0137 | 0.0102 | 0.0181 | 0.0077 | 25% vitamin E |  |
|  | 800 | 0.0059 | 0.0049 | 0.0199 | 0.0111 | 25% vitamin E |  |
|  | 1000 | 0.0071 | 0.0084 | 0.0197 | 0.0054 | 25% vitamin E |  |
|  | 1200 | 0.0057 | 0.0038 | 0.0072 | 0.0049 | 25% vitamin E |  |
|  | 1400 | 0.0121 | 0.0044 | 0.0137 | 0.0082 | 25% vitamin E |  |
|  | 1600 | 0.0092 | 0.0033 | 0.0205 | 0.0071 | 25% vitamin E |  |
| 6d | 0 | 3.7299 | 0.0800 | 4.5697 | 1.8594 | neat vitamin E-acetate | 16a-d |
|  | 200 | 2.7189 | 0.0569 | 1.1214 | 0.8907 | neat vitamin E-acetate |  |
|  | 400 | 0.6873 | 0.0440 | 0.3072 | 0.3641 | neat vitamin E-acetate |  |
|  | 600 | 0.2644 | 0.0388 | 0.1591 | 0.2402 | neat vitamin E-acetate |  |
|  | 800 | 0.1416 | 0.0345 | 0.0986 | 0.1524 | neat vitamin E-acetate |  |
|  | 1000 | 0.0991 | 0.0334 | 0.0905 | 0.1084 | neat vitamin E-acetate |  |
|  | 1200 | 0.0883 | 0.0299 | 0.0698 | 0.0793 | neat vitamin E-acetate |  |
|  | 1400 | 0.0842 | 0.0299 | 0.0594 | 0.0629 | neat vitamin E-acetate |  |
|  | 1600 | 0.0909 | 0.0370 | 0.0598 | 0.0578 | neat vitamin E-acetate |  |

FIGS. 1-16 illustrates oxidation index versus depth and trans-vinylene index versus depth from the top to bottom, side to middle, middle to side, or side to side, for Examples 1 and 3-6.

Figure 1B:
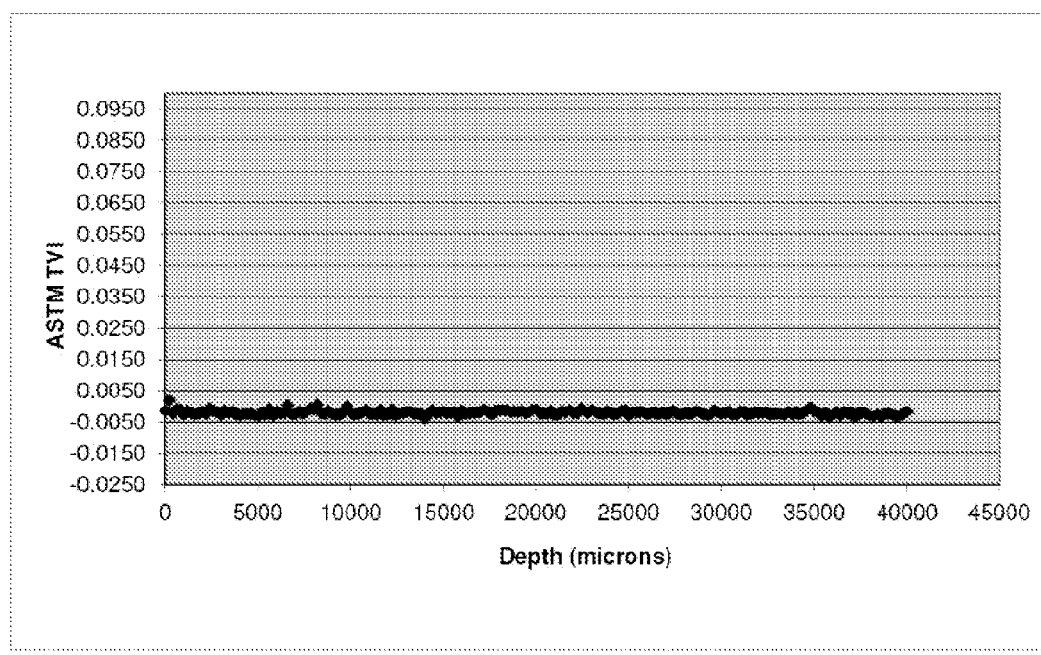
FIG. 1b illustrates trans-vinylene index versus depth from the top to the bottom of the sample of Example 1, in accordance with various embodiments.

FIG. 1a illustrates oxidation index versus depth from the top to the bottom of the sample of Example 1. FIG. 1b illustrates trans-vinylene index versus depth from the top to the bottom of the sample of Example 1. The trans-vinylene index throughout the Examples is determined as the area of the infrared absorption peak centered near 965 cm$^{-1}$ to the area of the of the C—H absorption peak centered near 1370 cm$^{-1}$. The area of the trans-vinylene absorptions (—C═C—) centered near 965 cm$^{-1}$ is related to the amount of crosslinking experienced by the material when exposed to ionizing radiation. Polymer main chain unsaturation in the form of trans-vinyl groups are a side reaction during crosslinking via ionizing radiation such as gamma, x-ray and electron beam. The correlation between TVI and actual received radiation dose can depend on the nature of the irradiation conditions, for example, radiation source (gamma or electron beam), temperature, dose rate, and oxygen level. The amount of unsaturation formation can be directly correlated with the amount of irradiation (i.e dose), and can be used as a dosimeter for a given material and irradiation method combination.

Figure 2A:
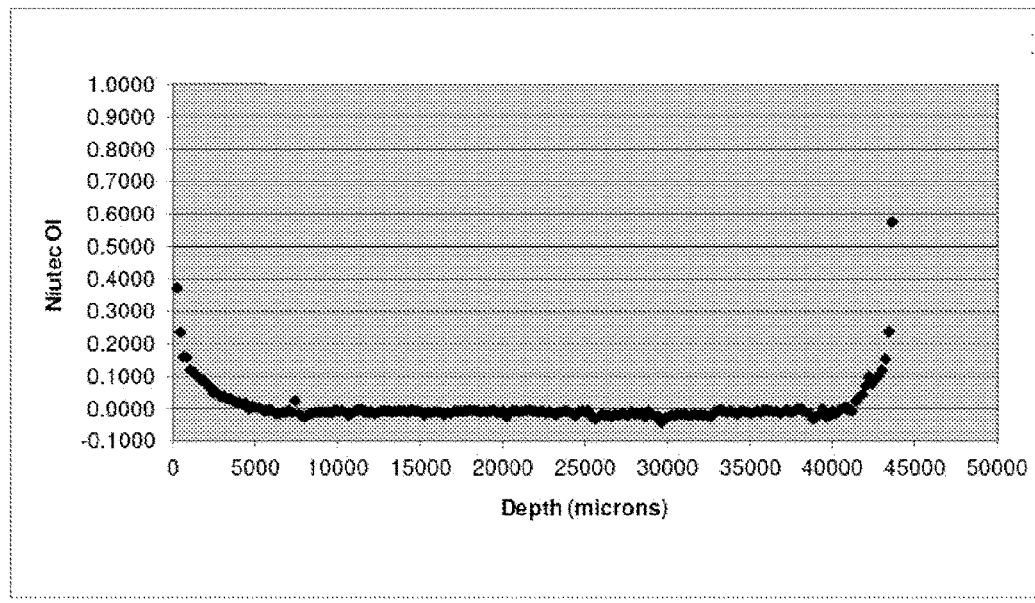
FIG. 2a illustrates oxidation index versus depth from the top to the bottom of the sample of Example 3a, in accordance with various embodiments.
Figure 2B:
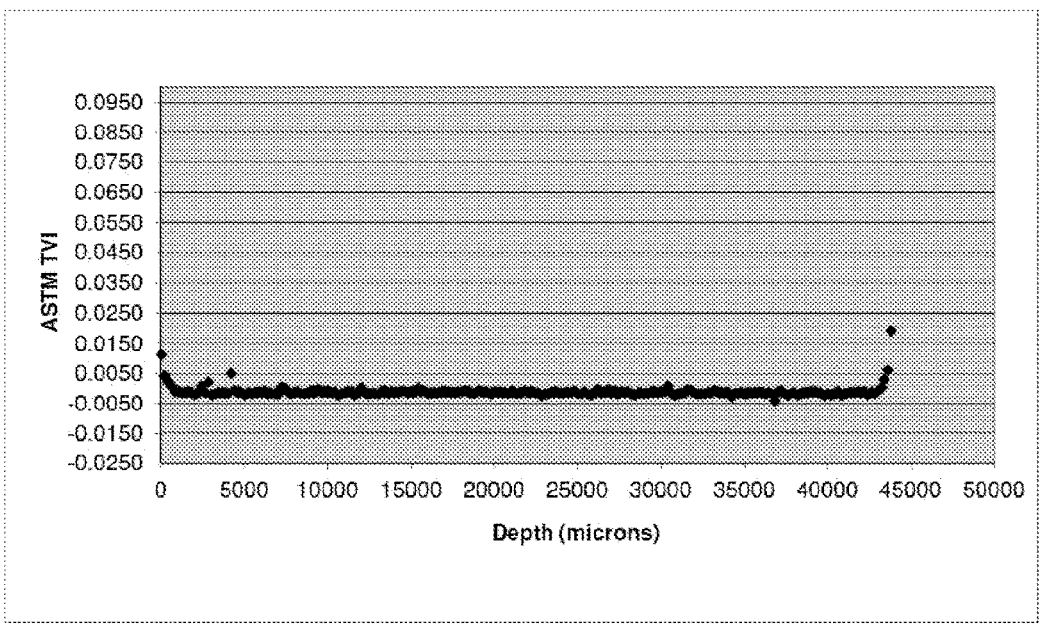
FIG. 2b illustrates trans-vinylene index versus depth from the top to the bottom of the sample of Example 3a, in accordance with various embodiments.

FIG. 2a illustrates oxidation index versus depth from the top to the bottom of the sample of Example 3a. FIG. 2b illustrates trans-vinylene index versus depth from the top to the bottom of the sample of Example 3a.

Figure 3A:
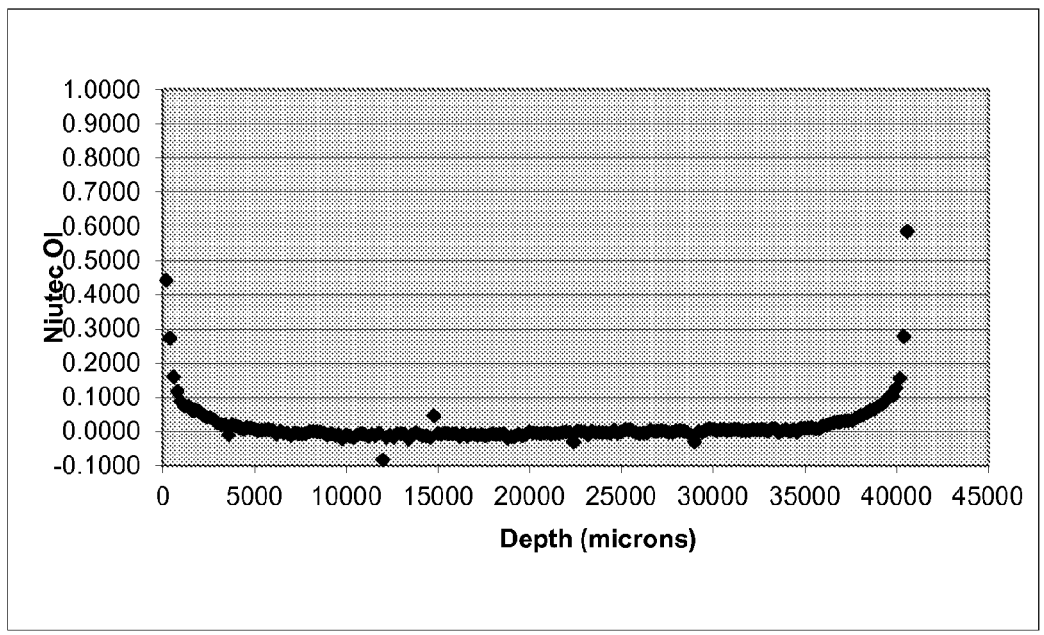
FIG. 3a illustrates oxidation index versus depth from the top to the bottom of the sample of Example 3b, in accordance with various embodiments.
Figure 3B:
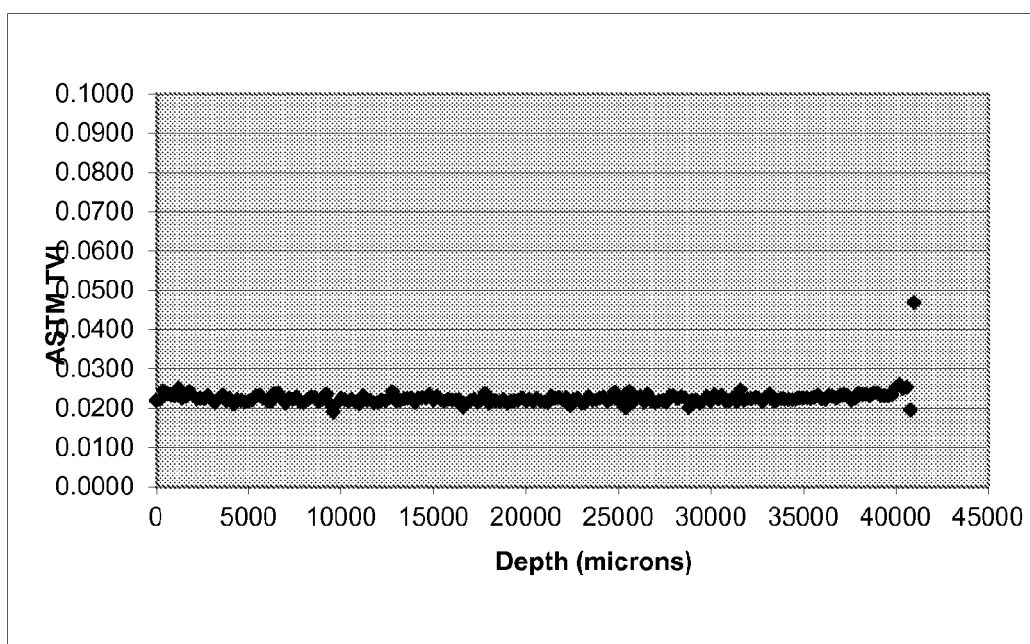
FIG. 3b illustrates trans-vinylene index versus depth from the top to the bottom of the sample of Example 3b, in accordance with various embodiments.
Figure 3C:
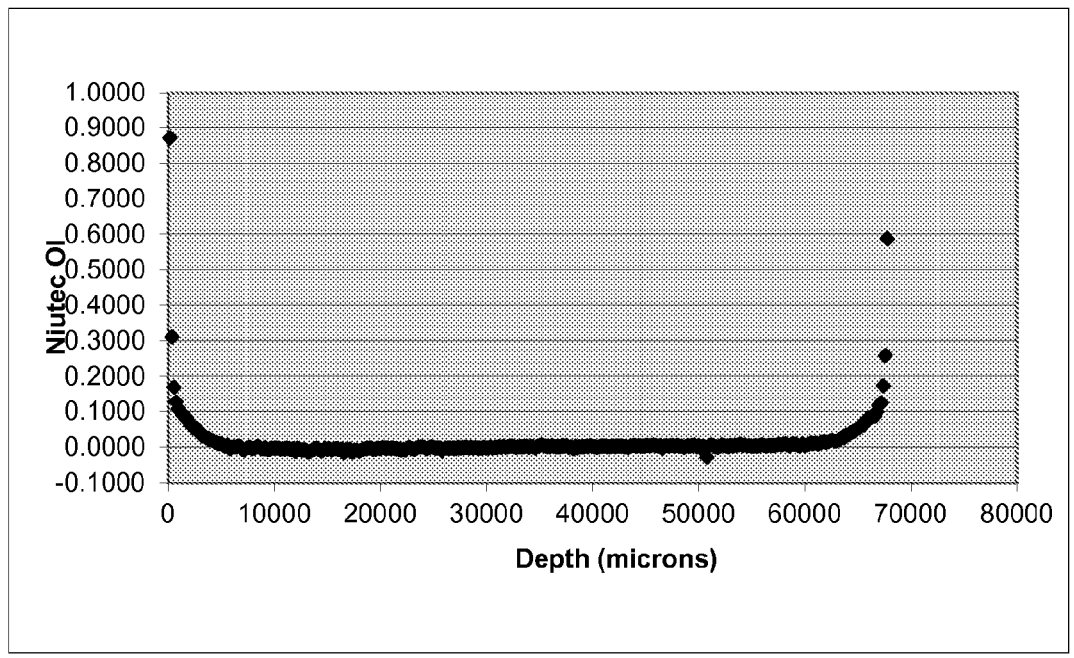
FIG. 3c illustrates oxidation index versus depth from side to side of the sample of Example 3b, in accordance with various embodiments.
Figure 3D:
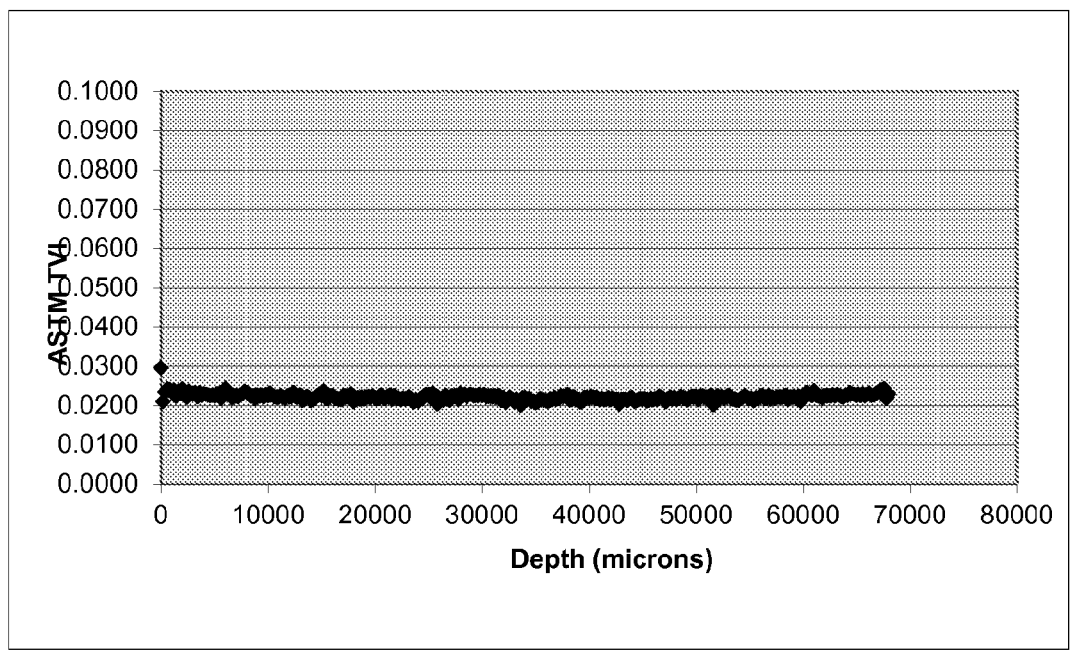
FIG. 3d illustrates trans-vinylene index versus depth from side to side of the sample of Example 3b, in accordance with various embodiments.

FIG. 3a illustrates oxidation index versus depth from the top to the bottom of the sample of Example 3b. FIG. 3b illustrates trans-vinylene index versus depth from the top to the bottom of the sample of Example 3b. FIG. 3c illustrates oxidation index versus depth from side to side of the sample of Example 3b. FIG. 3d illustrates trans-vinylene index versus depth from side to side of the sample of Example 3b.

Figure 4A:
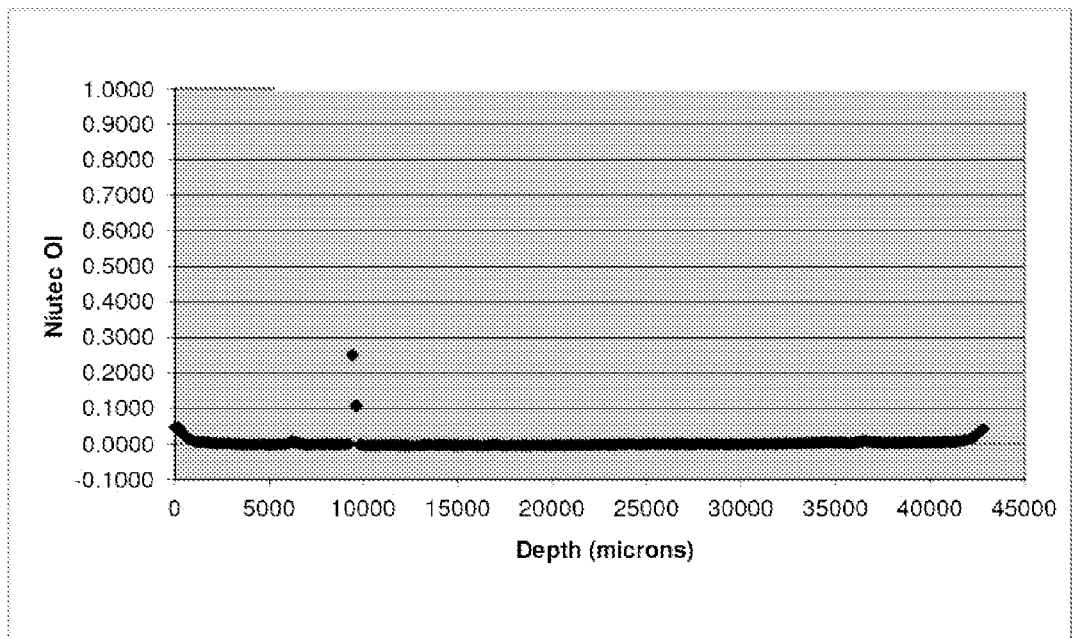
FIG. 4a illustrates oxidation index versus depth from the top to the bottom of the sample of Example 4a, in accordance with various embodiments.
Figure 4B:
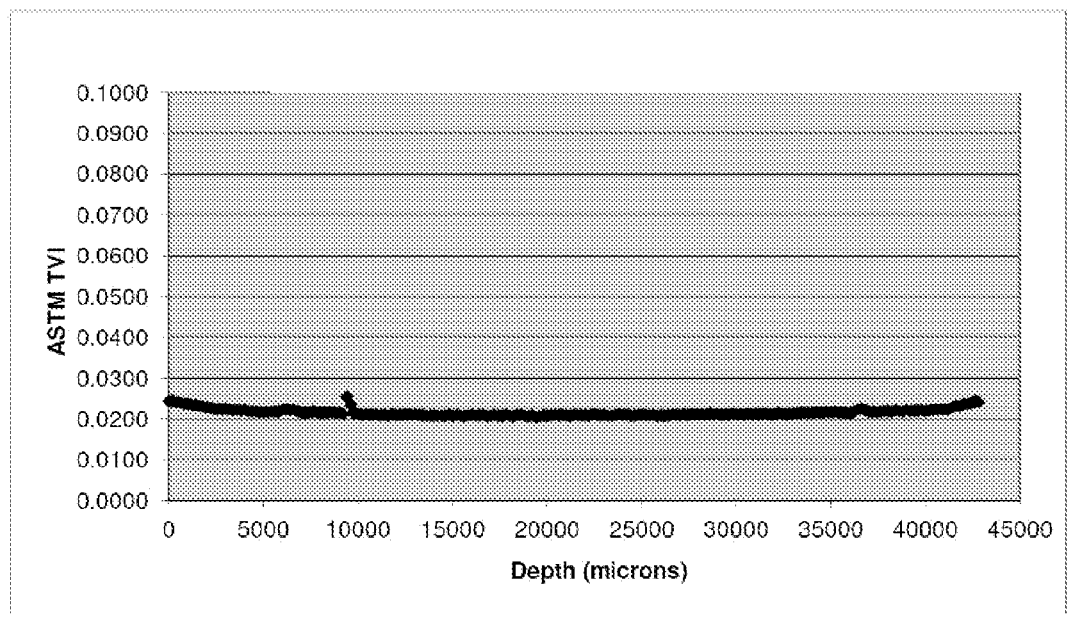
FIG. 4b illustrates trans-vinylene index versus depth from the top to the bottom of the sample of Example 4a, in accordance with various embodiments.
Figure 4C:
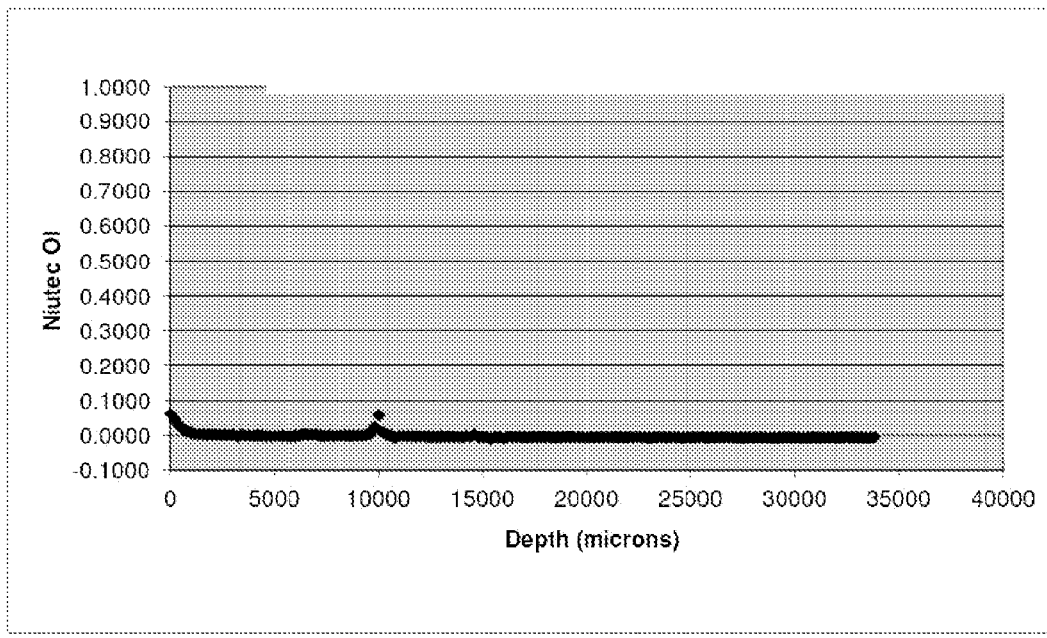
FIG. 4c illustrates oxidation index versus depth from side to middle of the sample of Example 4a, in accordance with various embodiments.
Figure 4D:
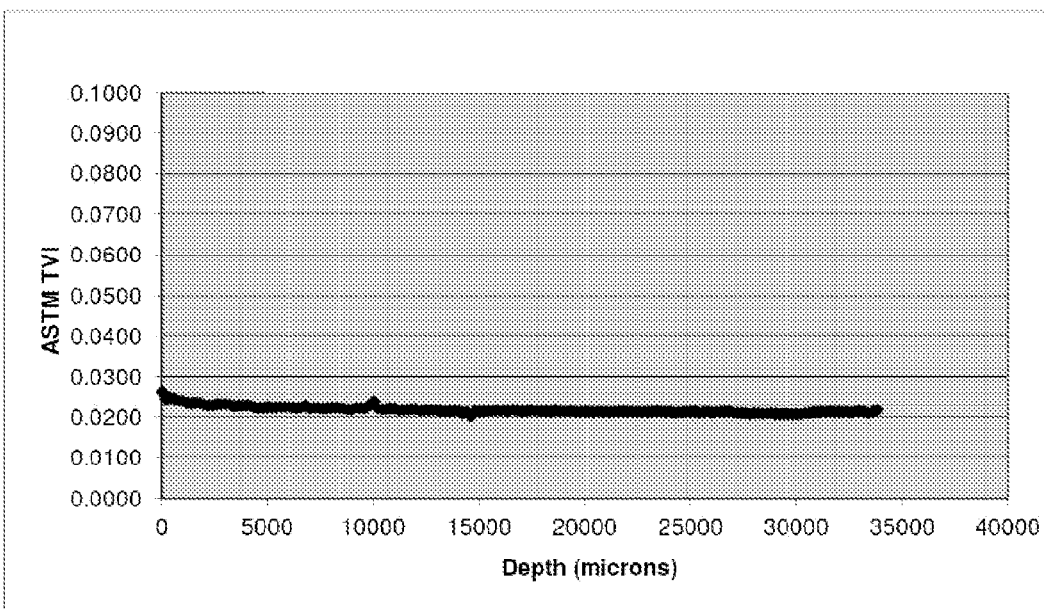
FIG. 4d illustrates trans-vinylene index versus depth from side to middle of the sample of Example 4a, in accordance with various embodiments.
Figure 4E:
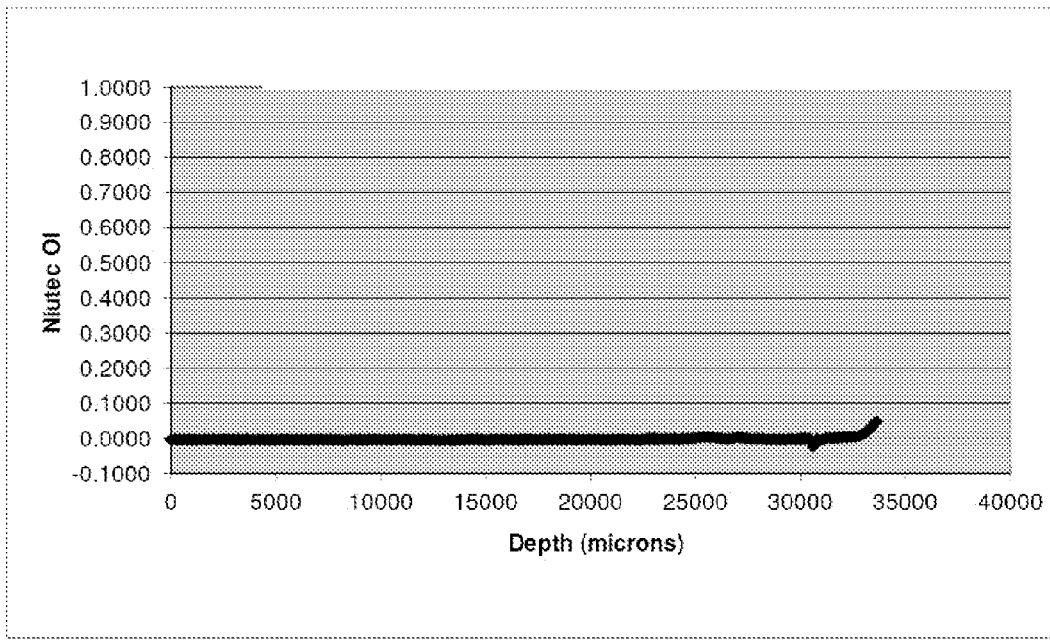
FIG. 4e illustrates oxidation index versus depth from middle to side of the sample of Example 4a, in accordance with various embodiments.
Figure 4F:
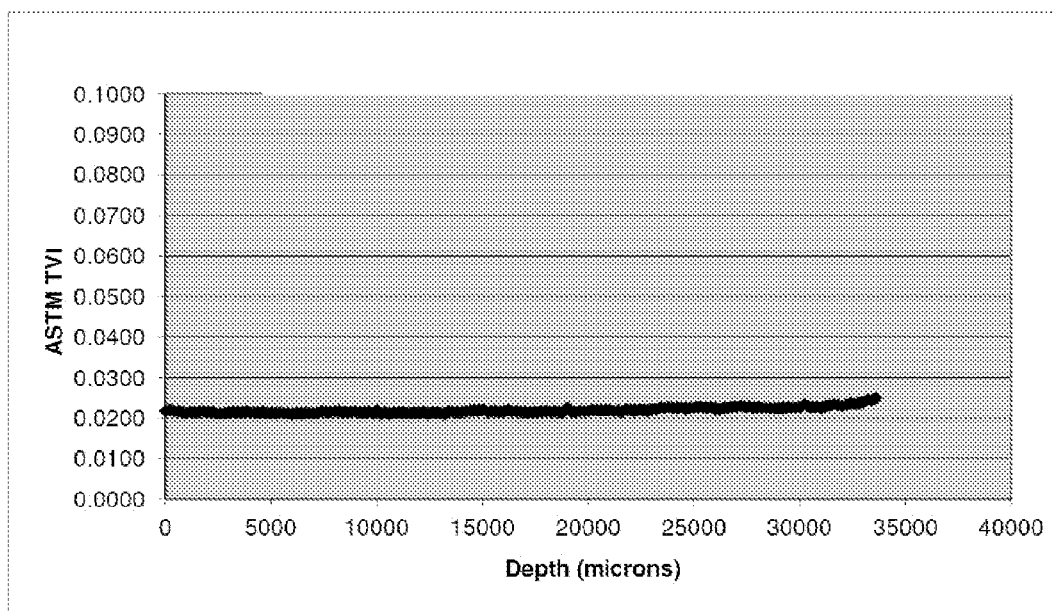
FIG. 4f illustrates trans-vinylene index versus depth from middle to side of the sample of Example 4a, in accordance with various embodiments.

FIG. 4a illustrates oxidation index versus depth from the top to the bottom of the sample of Example 4a. FIG. 4b illustrates trans-vinylene index versus depth from the top to the bottom of the sample of Example 4a. FIG. 4c illustrates oxidation index versus depth from side to middle of the sample of Example 4a. FIG. 4d illustrates trans-vinylene index versus depth from side to middle of the sample of Example 4a. FIG. 4e illustrates oxidation index versus depth from middle to side of the sample of Example 4a. FIG. 4f illustrates trans-vinylene index versus depth from middle to side of the sample of Example 4a.

Figure 5A:
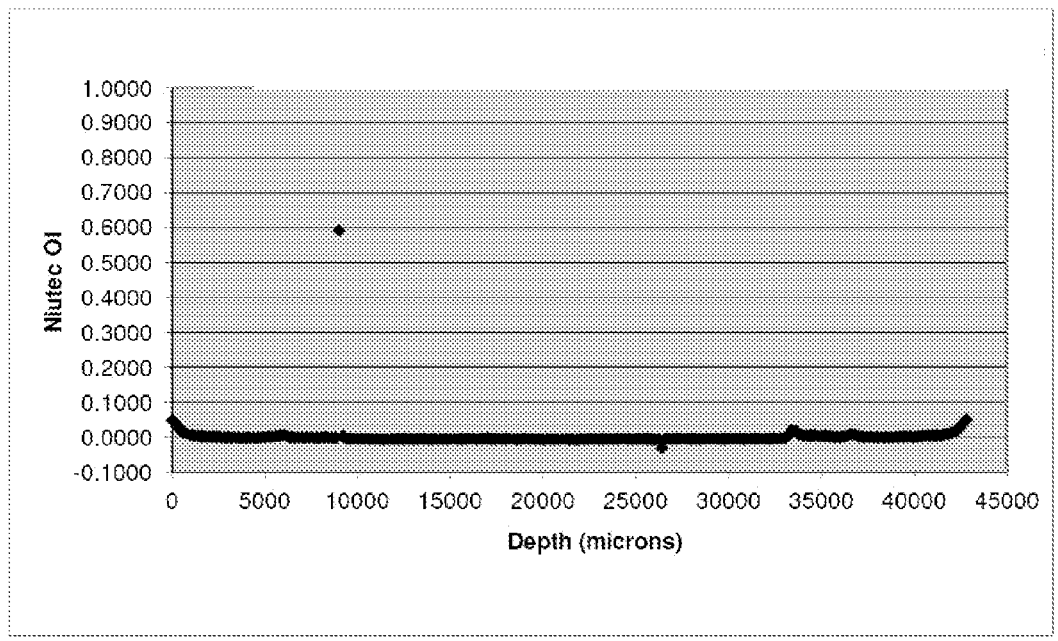
FIG. 5a illustrates oxidation index versus depth from the top to the bottom of the sample of Example 4c, in accordance with various embodiments.
Figure 5B:
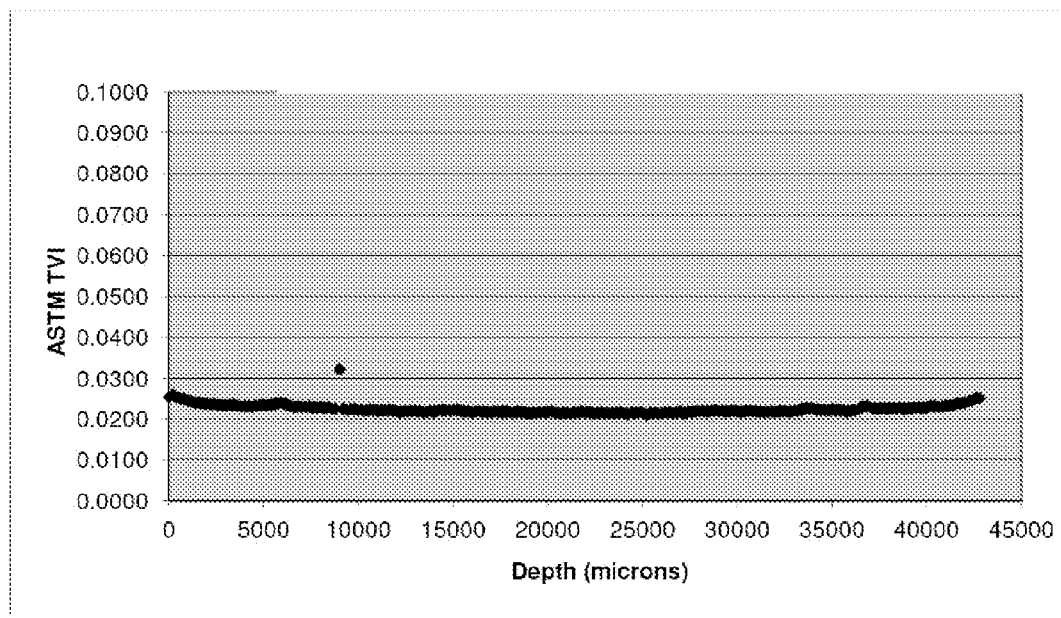
FIG. 5b illustrates trans-vinylene index versus depth from the top to the bottom of the sample of Example 4c, in accordance with various embodiments.
Figure 5C:
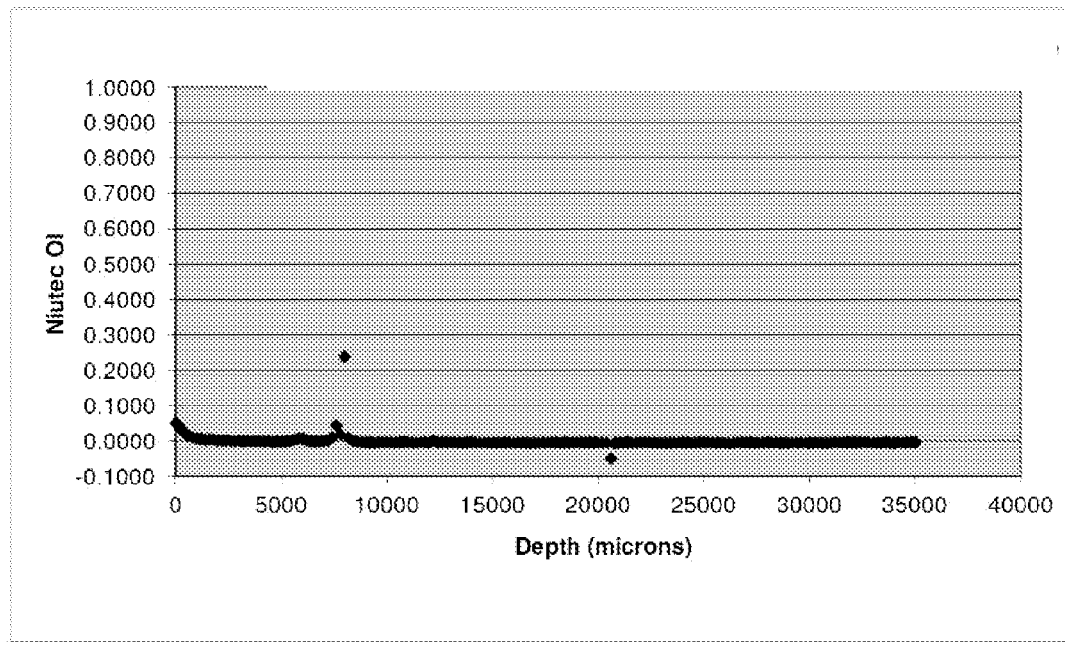
FIG. 5c illustrates oxidation index versus depth from side to middle of the sample of Example 4c, in accordance with various embodiments.
Figure 5D:
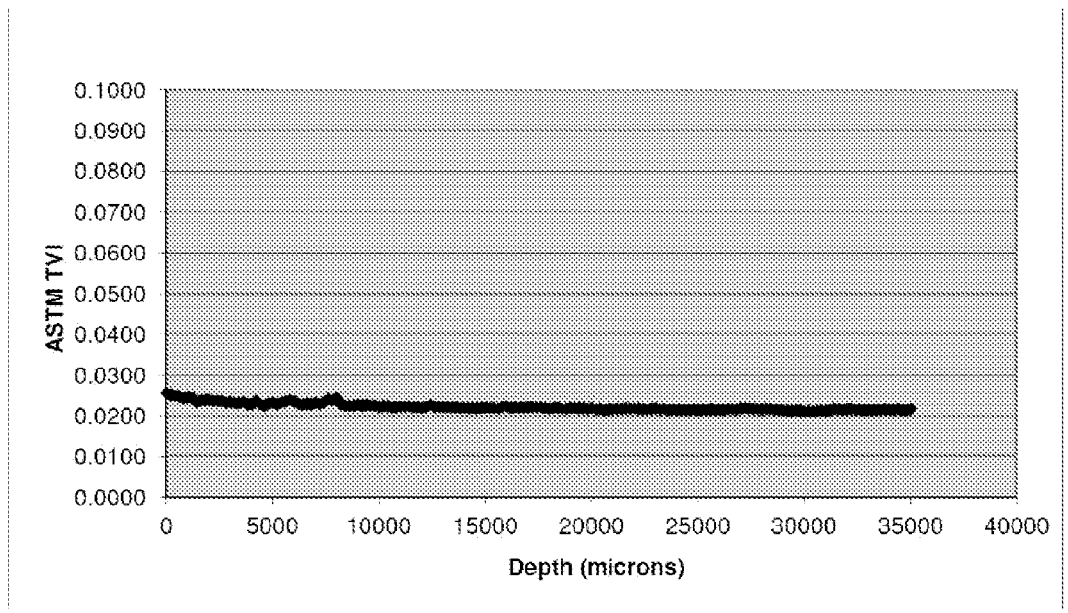
FIG. 5d illustrates trans-vinylene index versus depth from side to middle of the sample of Example 4c, in accordance with various embodiments.
Figure 5E:
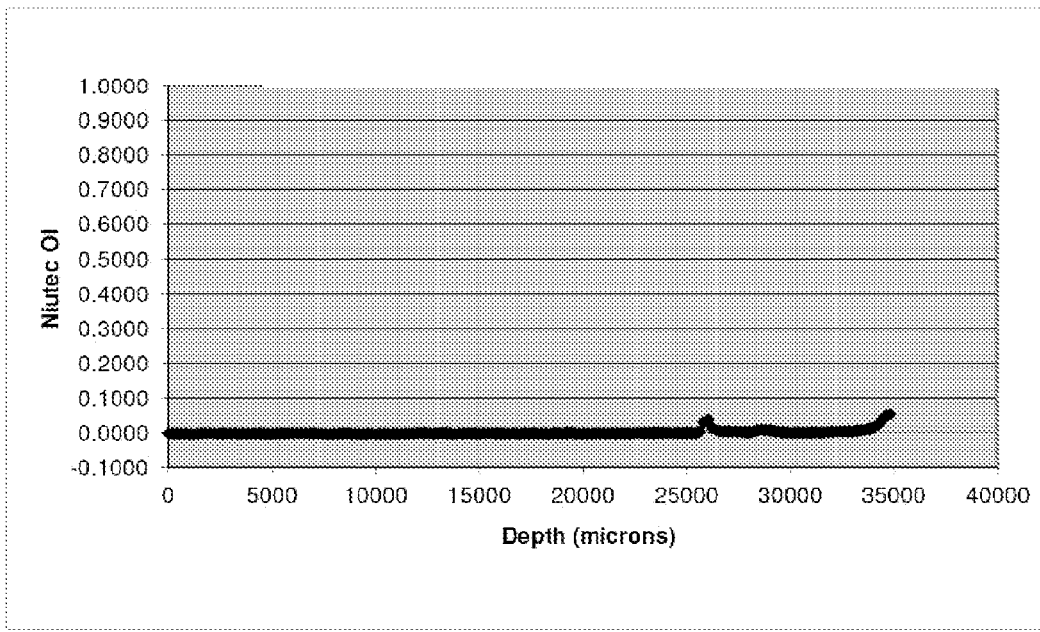
FIG. 5e illustrates oxidation index versus depth from middle to side of the sample of Example 4c, in accordance with various embodiments.
Figure 5F:
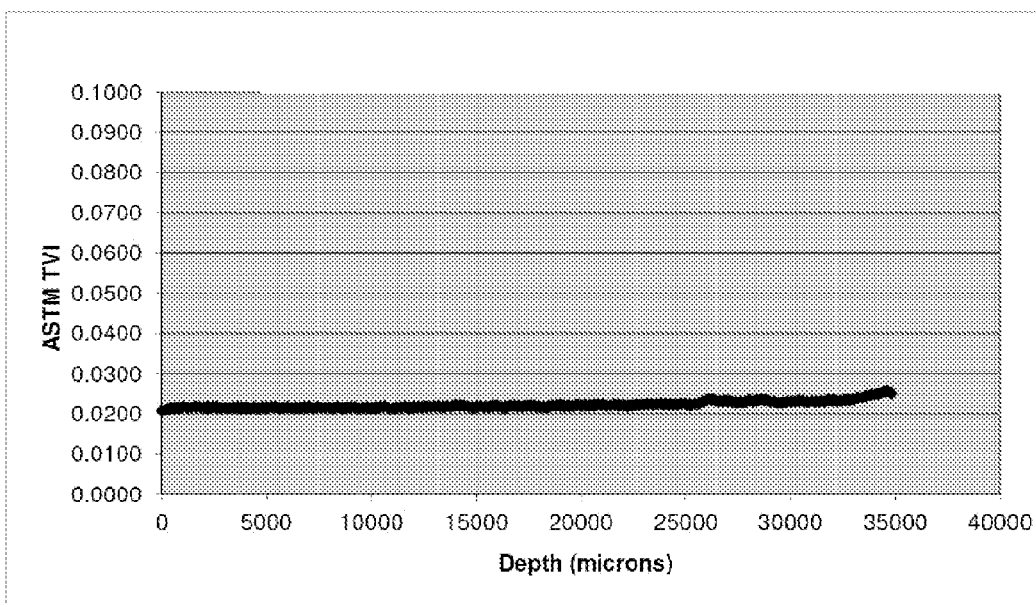
FIG. 5f illustrates trans-vinylene index versus depth from middle to side of the sample of Example 4c, in accordance with various embodiments.

FIG. 5a illustrates oxidation index versus depth from the top to the bottom of the sample of Example 4c. FIG. 5b illustrates trans-vinylene index versus depth from the top to the bottom of the sample of Example 4c. FIG. 5c illustrates oxidation index versus depth from side to middle of the sample of Example 4c. FIG. 5d illustrates trans-vinylene index versus depth from side to middle of the sample of Example 4c. FIG. 5e illustrates oxidation index versus depth from middle to side of the sample of Example 4c. FIG. 5f illustrates trans-vinylene index versus depth from middle to side of the sample of Example 4c.

Figure 6A:
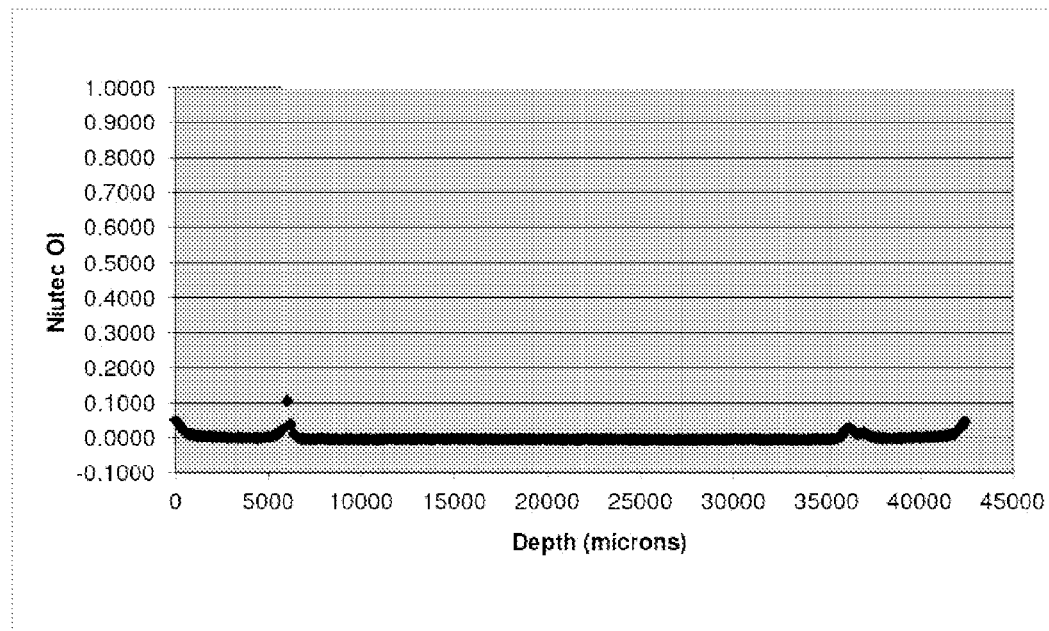
FIG. 6a illustrates oxidation index versus depth from the top to the bottom of the sample of Example 4d, in accordance with various embodiments.
Figure 6B:
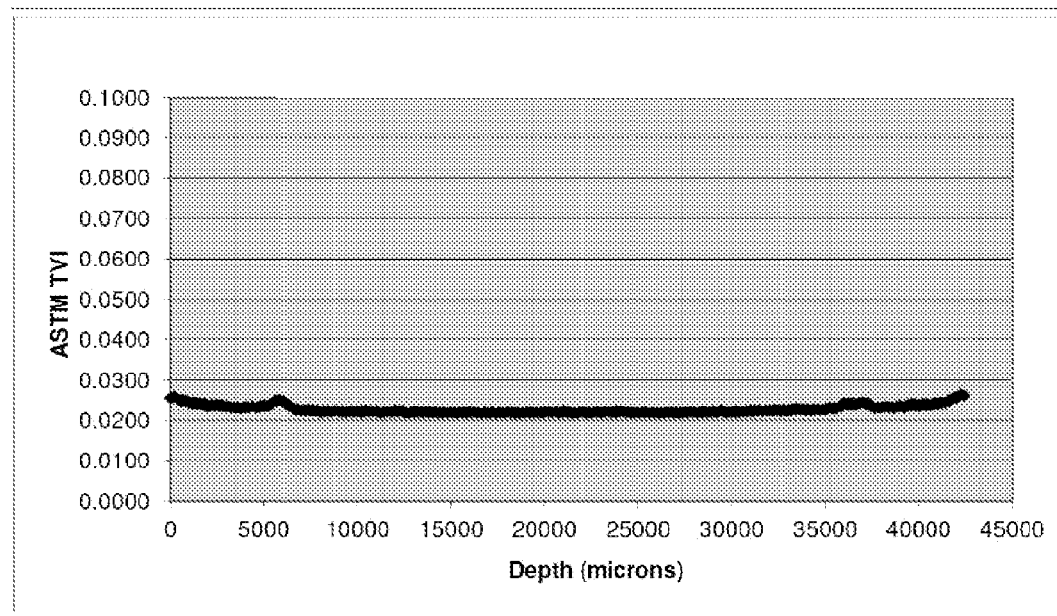
FIG. 6b illustrates trans-vinylene index versus depth from the top to the bottom of the sample of Example 4d, in accordance with various embodiments.
Figure 6C:
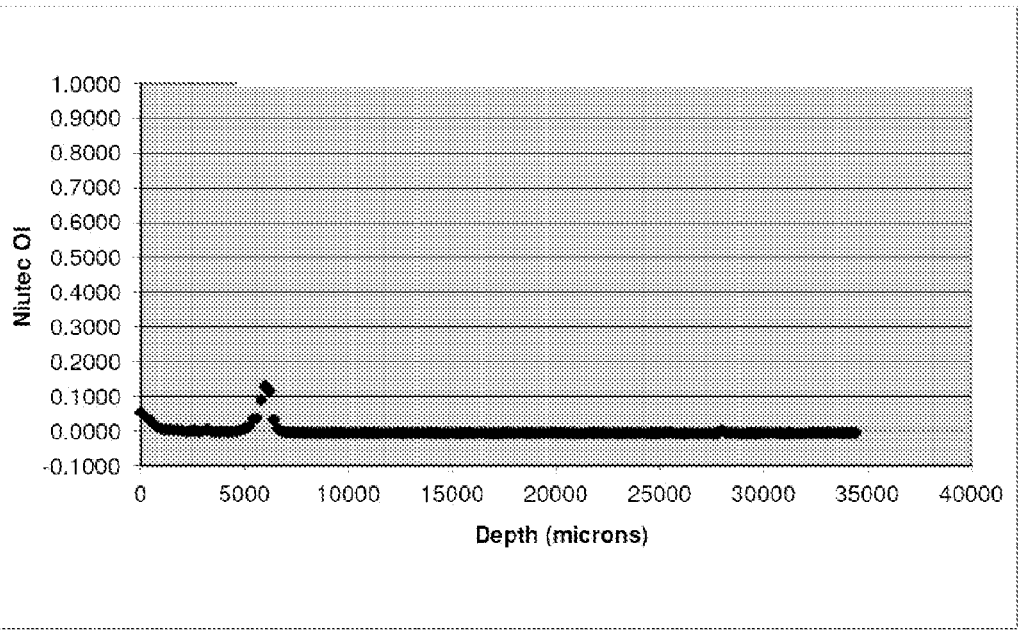
FIG. 6c illustrates oxidation index versus depth from side to middle of the sample of Example 4d, in accordance with various embodiments.
Figure 6D:
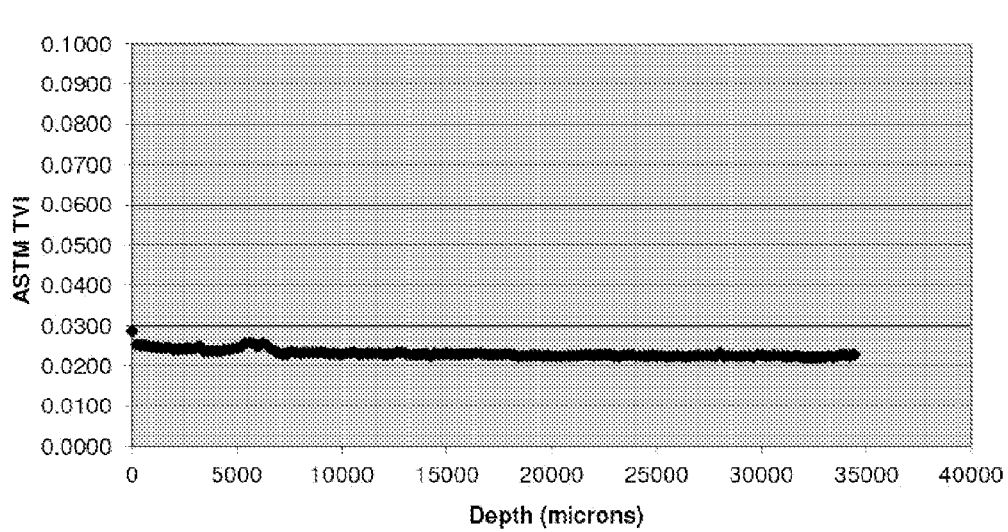
FIG. 6d illustrates trans-vinylene index versus depth from side to middle of the sample of Example 4d, in accordance with various embodiments.
Figure 6E:
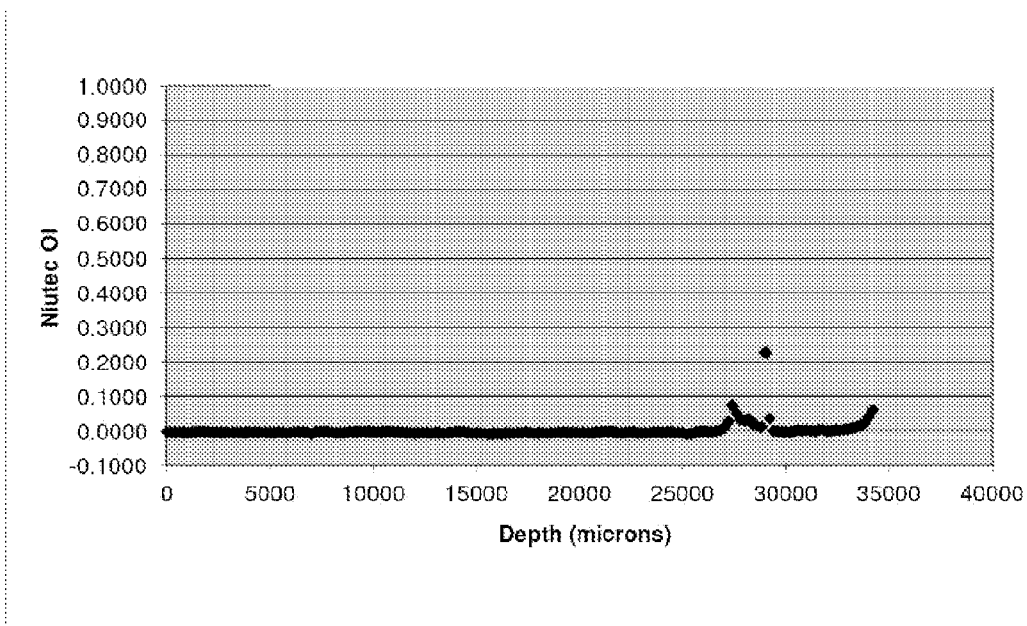
FIG. 6e illustrates oxidation index versus depth from middle to side of the sample of Example 4d, in accordance with various embodiments.
Figure 6F:
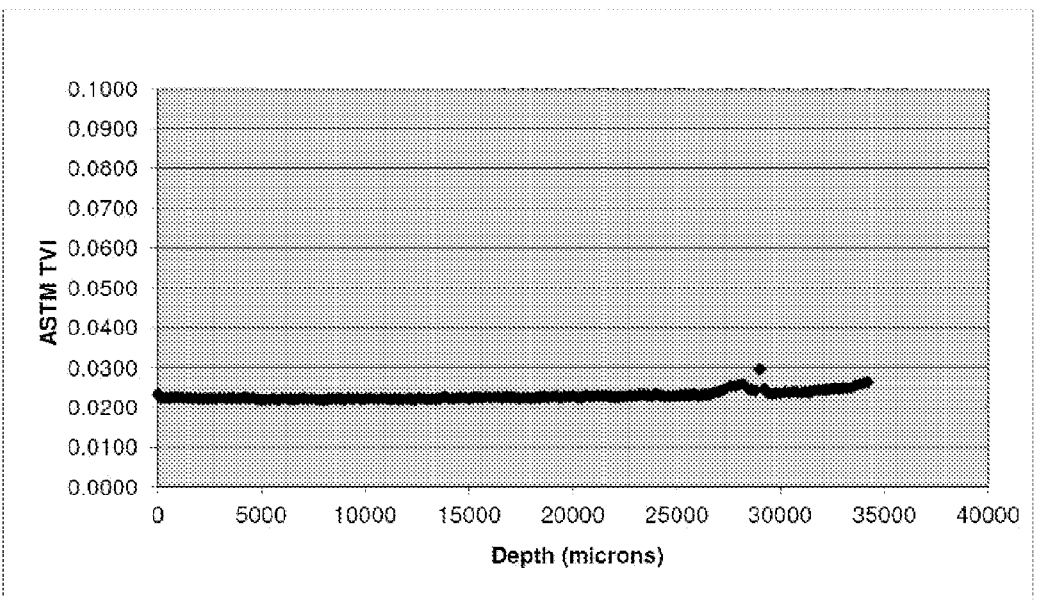
FIG. 6f illustrates trans-vinylene index versus depth from middle to side of the sample of Example 4d, in accordance with various embodiments.

FIG. 6a illustrates oxidation index versus depth from the top to the bottom of the sample of Example 4d. FIG. 6b illustrates trans-vinylene index versus depth from the top to the bottom of the sample of Example 4d. FIG. 6c illustrates oxidation index versus depth from side to middle of the sample of Example 4d. FIG. 6d illustrates trans-vinylene index versus depth from side to middle of the sample of Example 4d. FIG. 6e illustrates oxidation index versus depth from middle to side of the sample of Example 4d. FIG. 6f illustrates trans-vinylene index versus depth from middle to side of the sample of Example 4d.

Figure 7A:
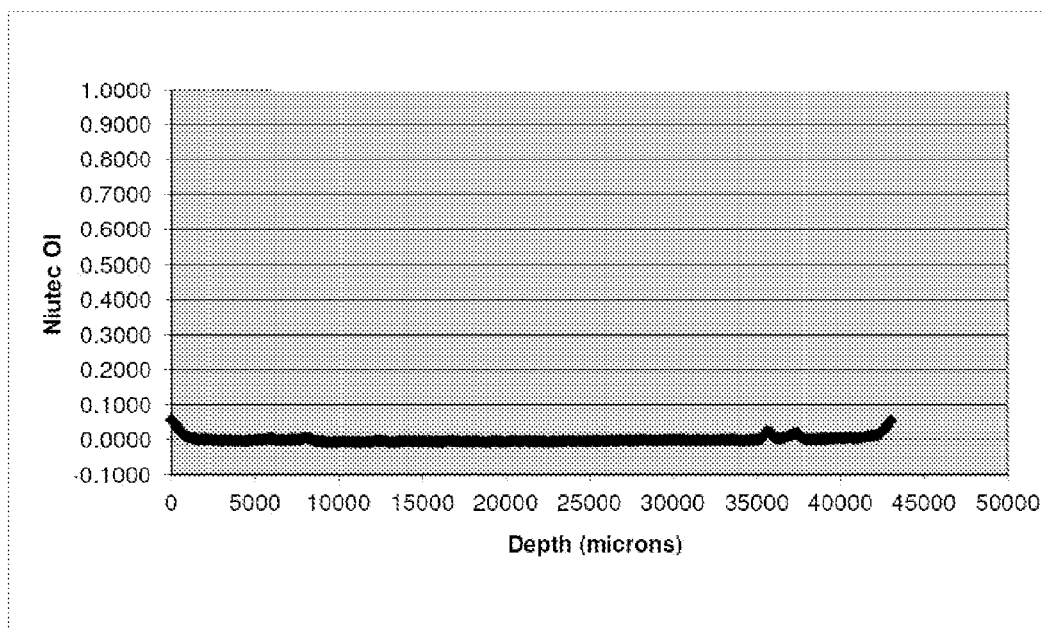
FIG. 7a illustrates oxidation index versus depth from the top to the bottom of the sample of Example 4e, in accordance with various embodiments.
Figure 7B:
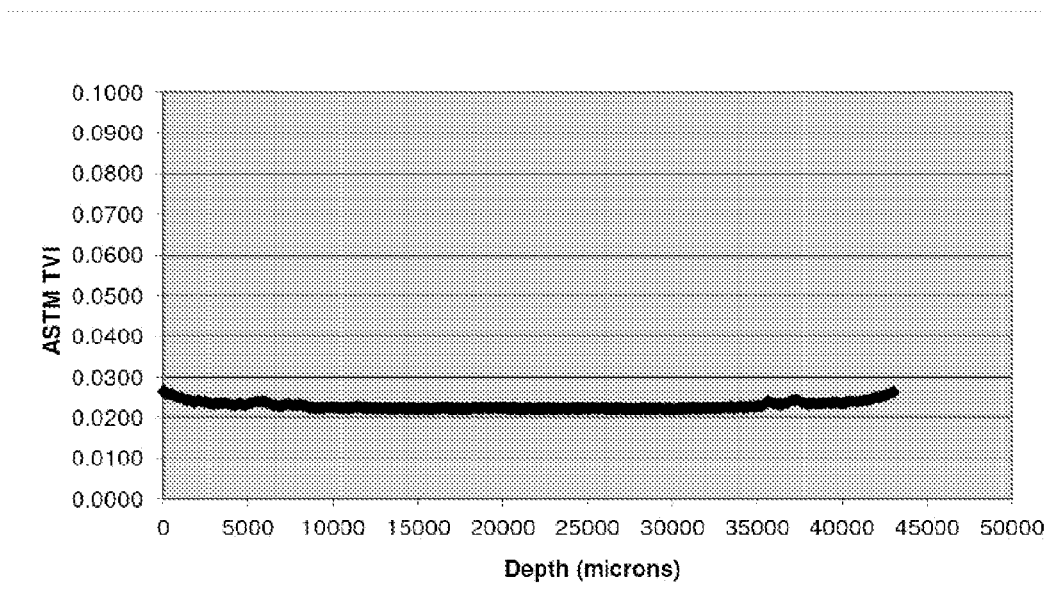
FIG. 7b illustrates trans-vinylene index versus depth from the top to the bottom of the sample of Example 4e, in accordance with various embodiments.
Figure 7C:
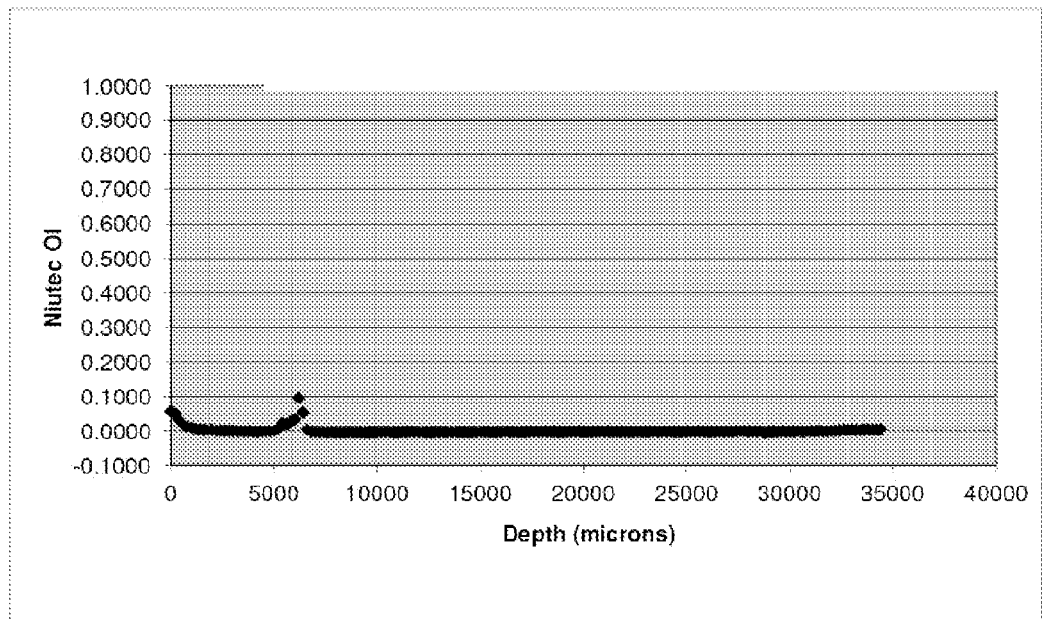
FIG. 7c illustrates oxidation index versus depth from side to middle of the sample of Example 4e, in accordance with various embodiments.
Figure 7D:
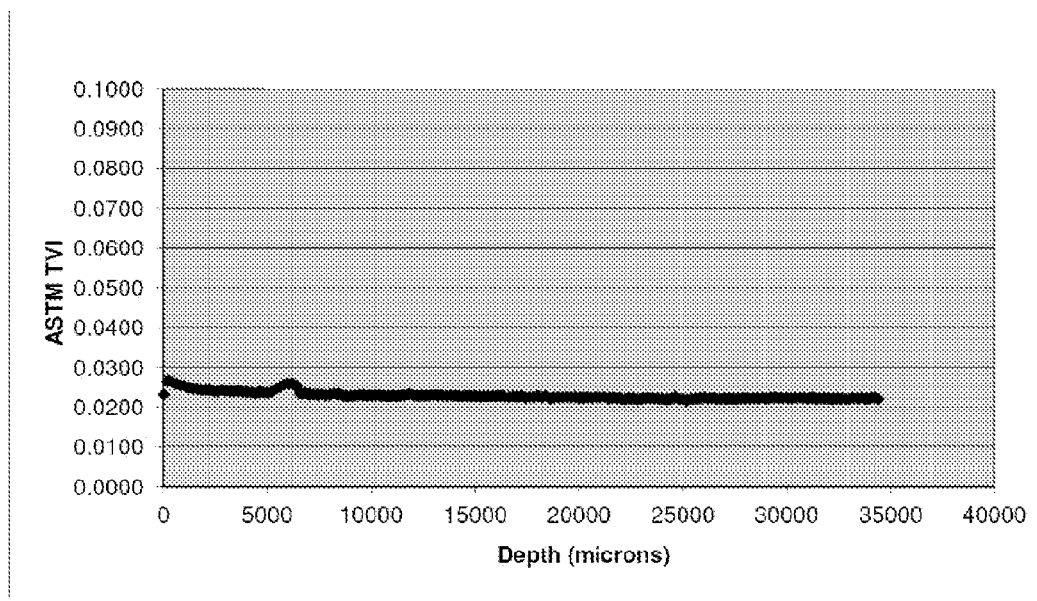
FIG. 7d illustrates trans-vinylene index versus depth from side to middle of the sample of Example 4e, in accordance with various embodiments.
Figure 7E:
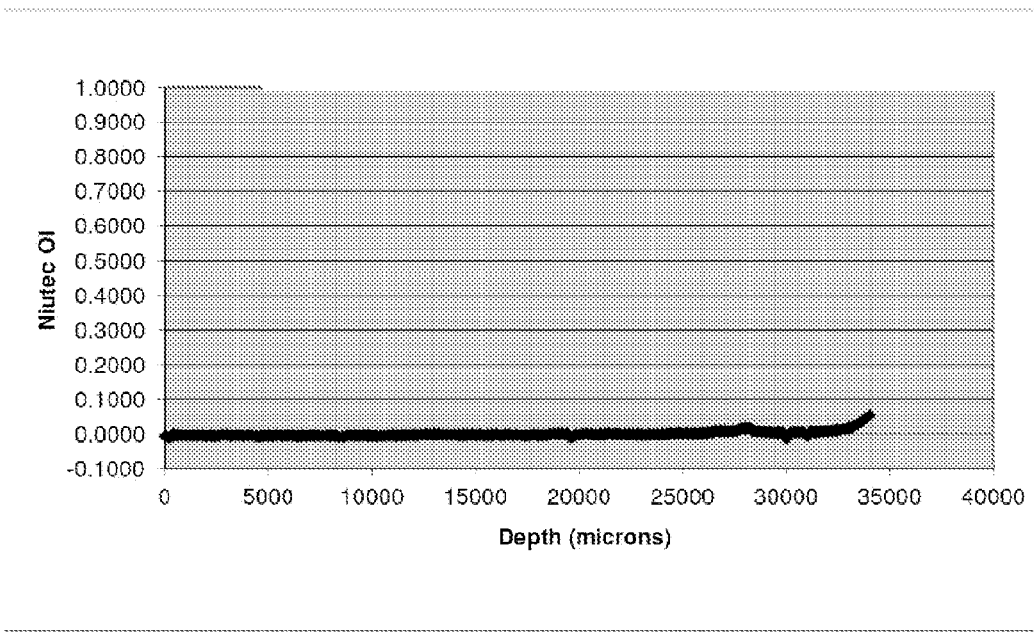
FIG. 7e illustrates oxidation index versus depth from middle to side of the sample of Example 4e, in accordance with various embodiments.
Figure 7F:
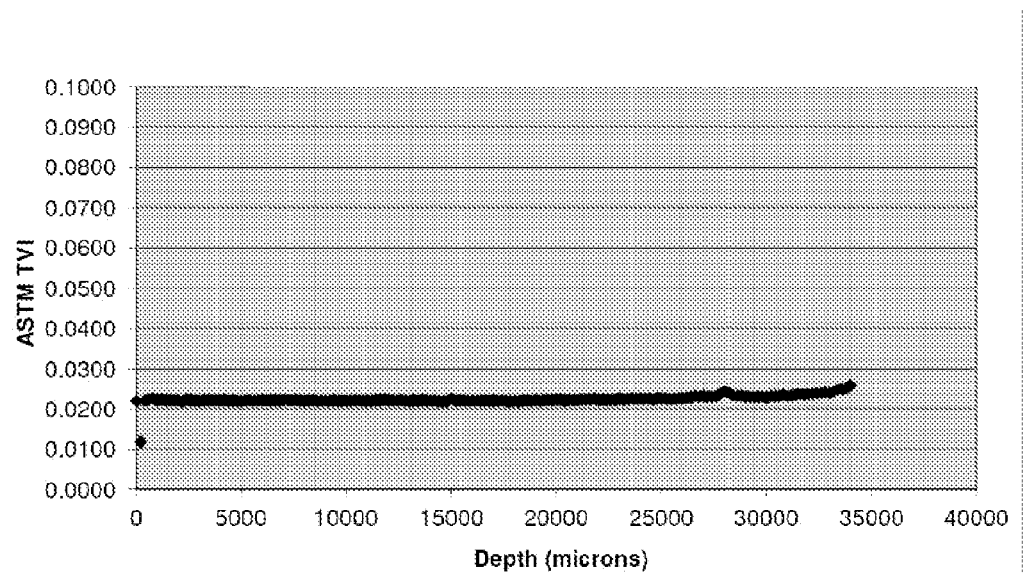
FIG. 7f illustrates trans-vinylene index versus depth from middle to side of the sample of Example 4e, in accordance with various embodiments.

FIG. 7a illustrates oxidation index versus depth from the top to the bottom of the sample of Example 4e. FIG. 7b illustrates trans-vinylene index versus depth from the top to the bottom of the sample of Example 4e. FIG. 7c illustrates oxidation index versus depth from side to middle of the sample of Example 4e. FIG. 7d illustrates trans-vinylene index versus depth from side to middle of the sample of Example 4e. FIG. 7e illustrates oxidation index versus depth from middle to side of the sample of Example 4e. FIG. 7f illustrates trans-vinylene index versus depth from middle to side of the sample of Example 4e.

Figure 8A:
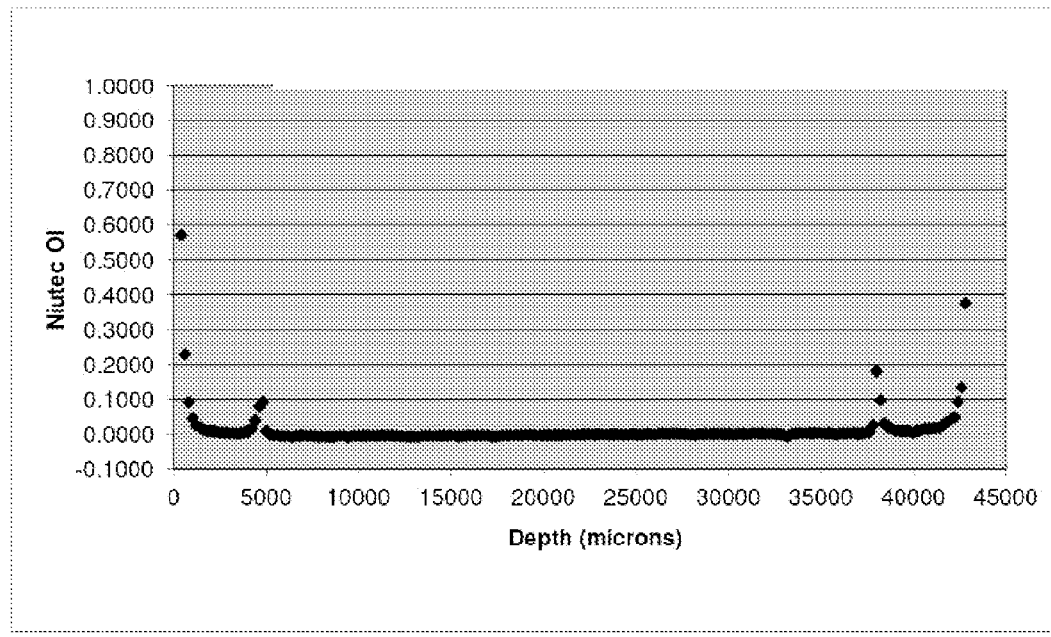
FIG. 8a illustrates oxidation index versus depth from the top to the bottom of the sample of Example 4f, in accordance with various embodiments.
Figure 8B:
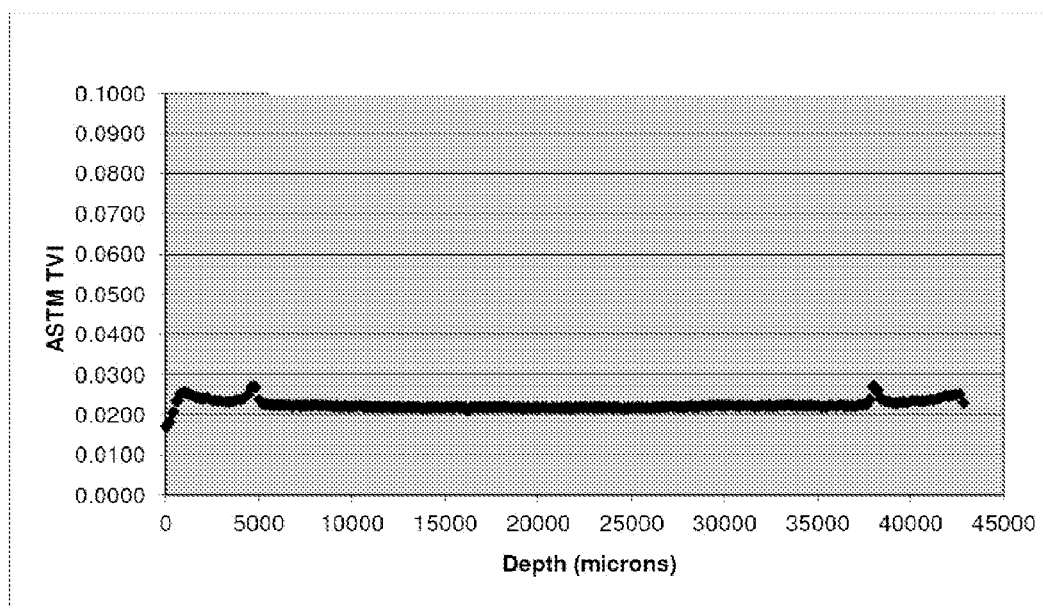
FIG. 8b illustrates trans-vinylene index versus depth from the top to the bottom of the sample of Example 4f, in accordance with various embodiments.
Figure 8C:
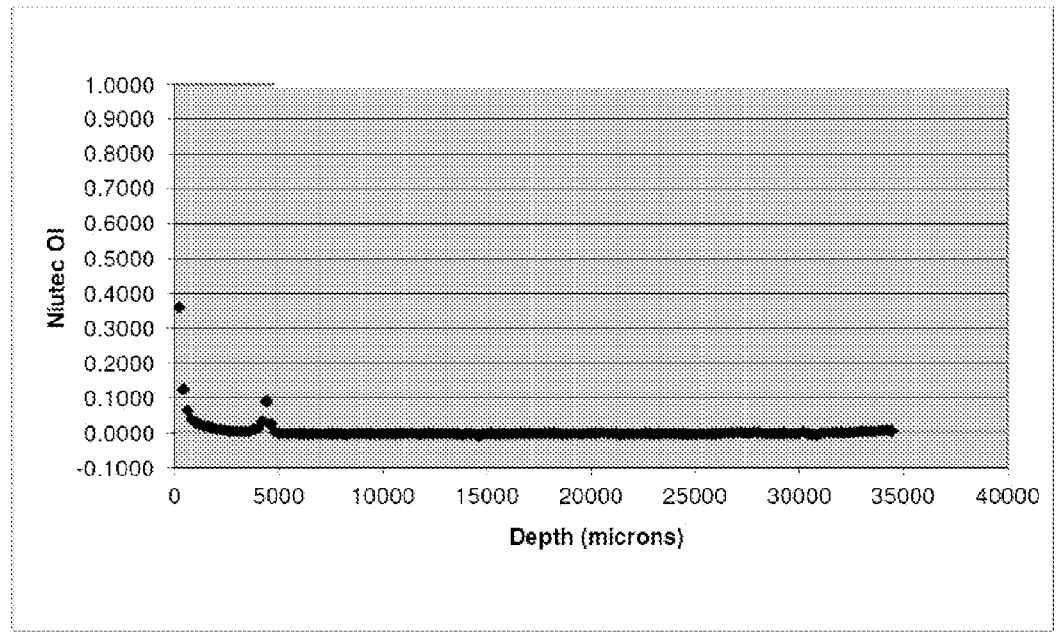
FIG. 8c illustrates oxidation index versus depth from side to side of the sample of Example 4f, in accordance with various embodiments.
Figure 8D:
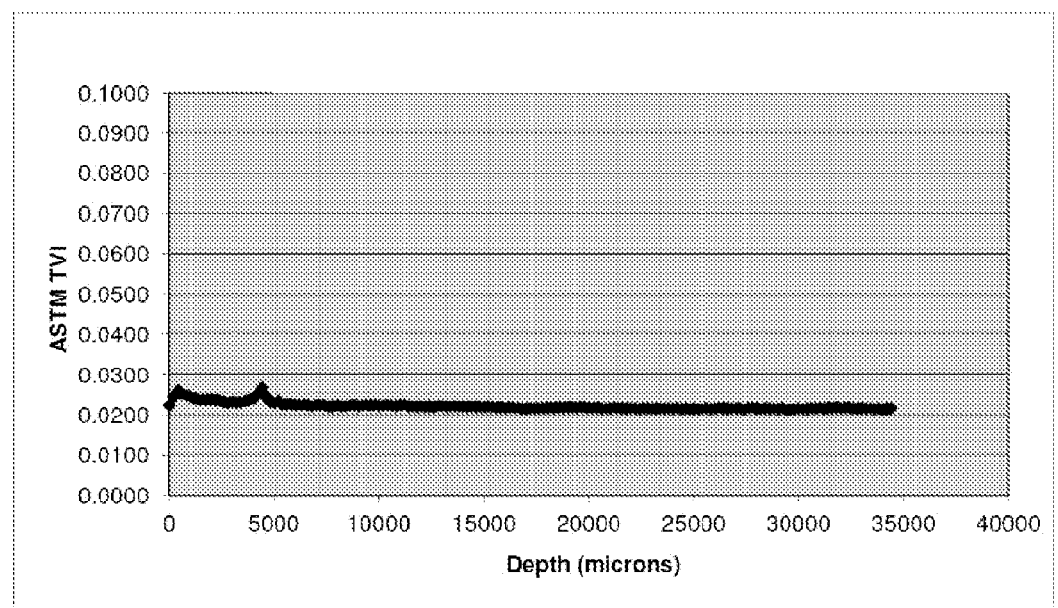
FIG. 8d illustrates trans-vinylene index versus depth from side to side of the sample of Example 4f, in accordance with various embodiments.
Figure 8E:
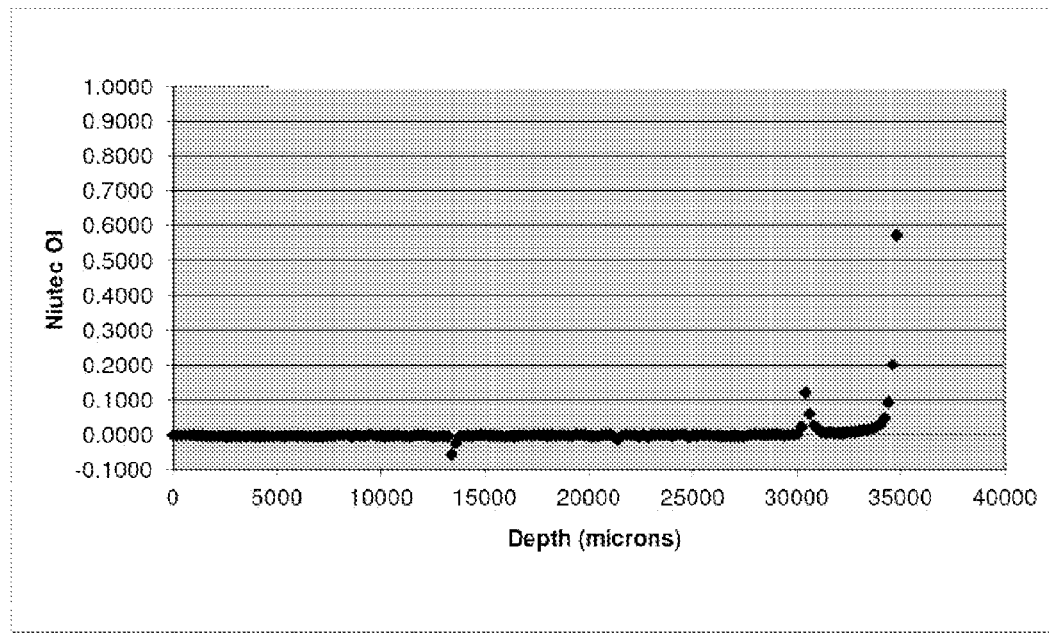
FIG. 8e illustrates oxidation index versus depth from side to middle of the sample of Example 4f, in accordance with various embodiments.
Figure 8F:
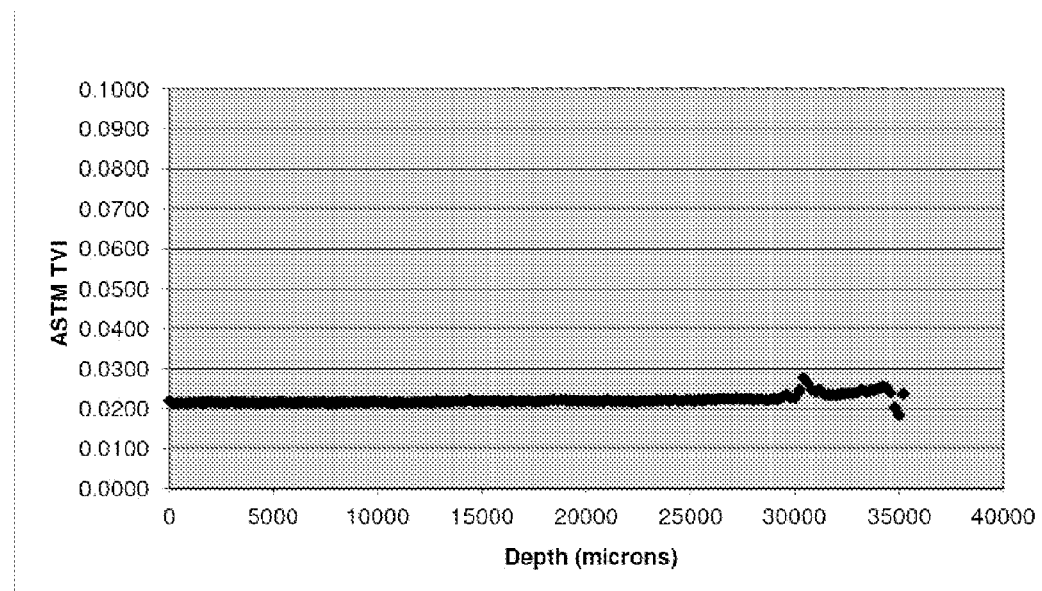
FIG. 8f illustrates trans-vinylene index versus depth from middle to side of the sample of Example 4f, in accordance with various embodiments.

FIG. 8a illustrates oxidation index versus depth from the top to the bottom of the sample of Example 4f. FIG. 8b illustrates trans-vinylene index versus depth from the top to the bottom of the sample of Example 4f. FIG. 8c illustrates oxidation index versus depth from side to side of the sample of Example 4f. FIG. 8d illustrates trans-vinylene index versus depth from side to side of the sample of Example 4f. FIG. 8e illustrates oxidation index versus depth from side to middle of the sample of Example 4f. FIG. 8f illustrates trans-vinylene index versus depth from middle to side of the sample of Example 4f.

Figure 9A:
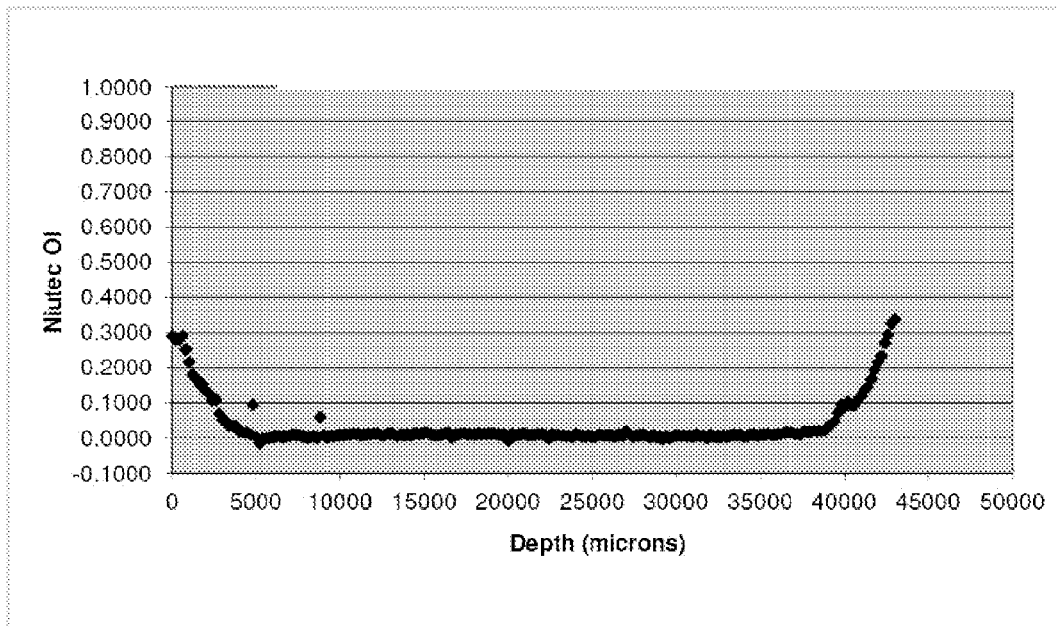
FIG. 9a illustrates oxidation index versus depth from the top to the bottom of the sample of Example 5a, in accordance with various embodiments.
Figure 9B:
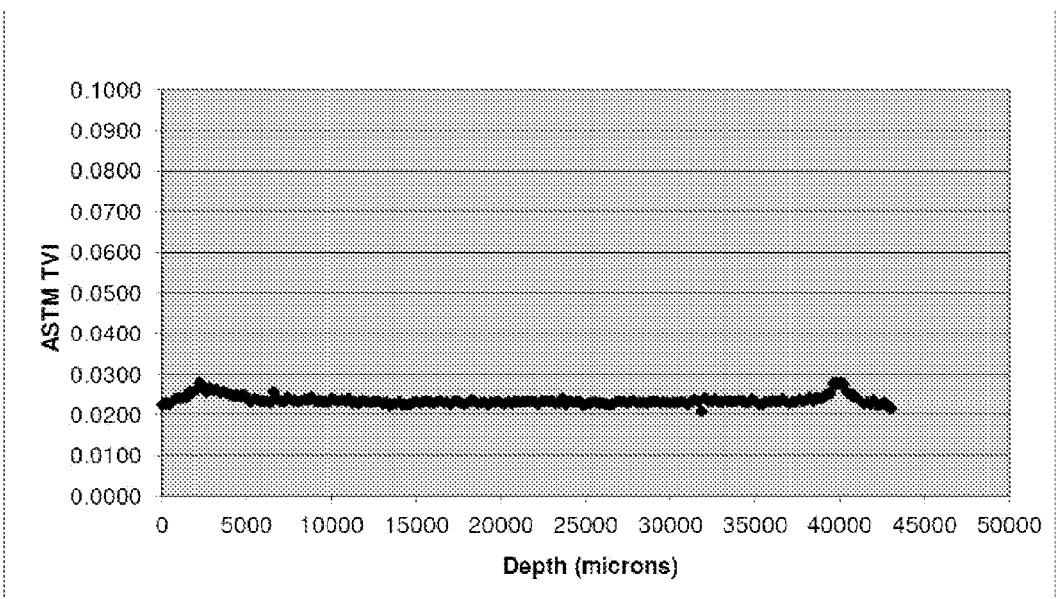
FIG. 9b illustrates trans-vinylene index versus depth from the top to the bottom of the sample of Example 5a, in accordance with various embodiments.
Figure 9C:
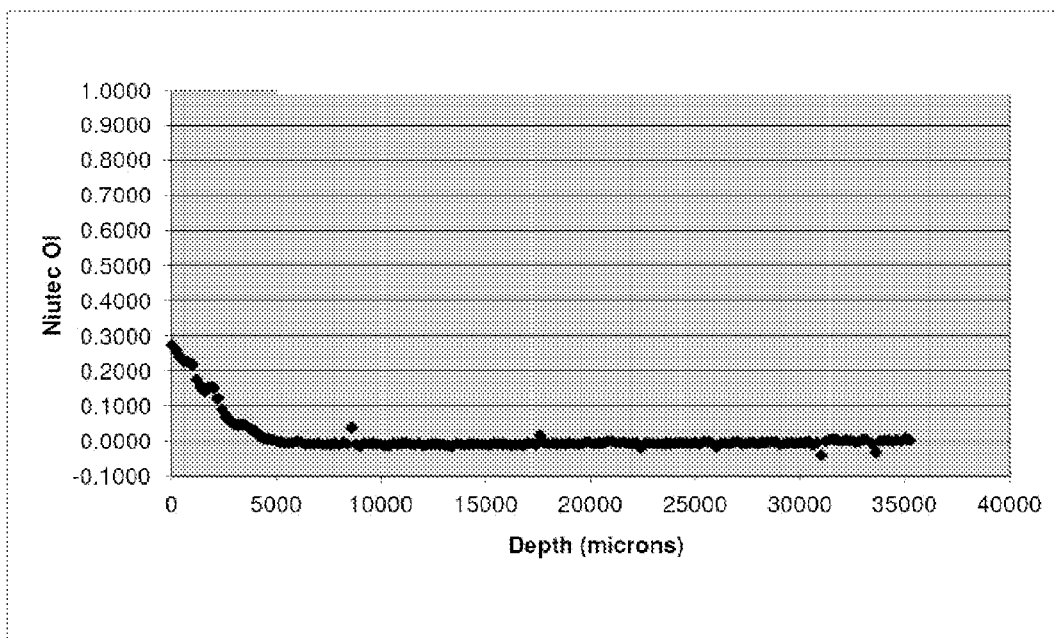
FIG. 9c illustrates oxidation index versus depth from side to middle of the sample of Example 5a, in accordance with various embodiments.
Figure 9D:
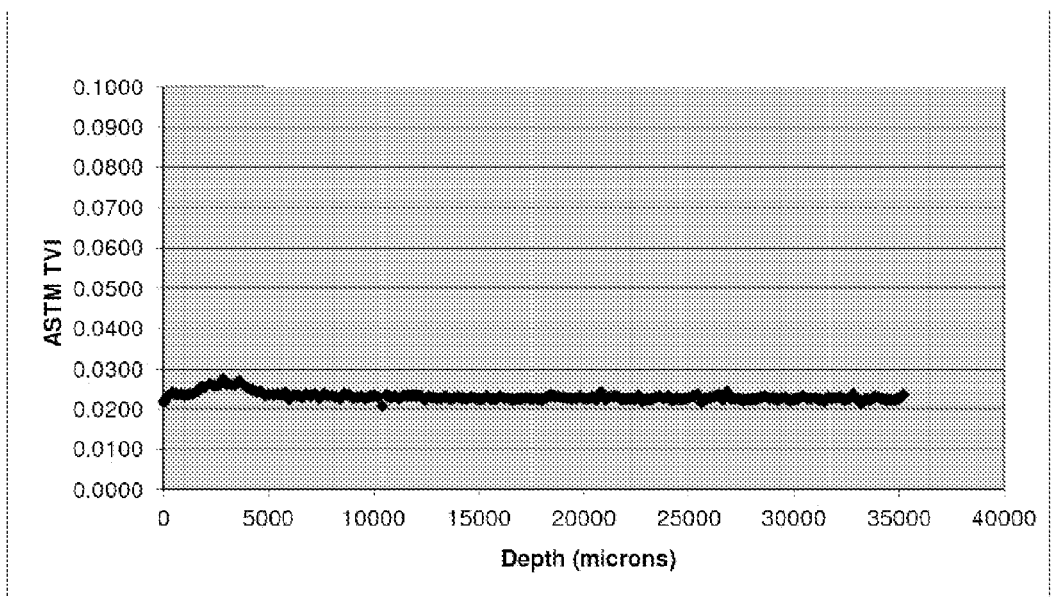
FIG. 9d illustrates trans-vinylene index versus depth from side to middle of the sample of Example 5a, in accordance with various embodiments.
Figure 9E:
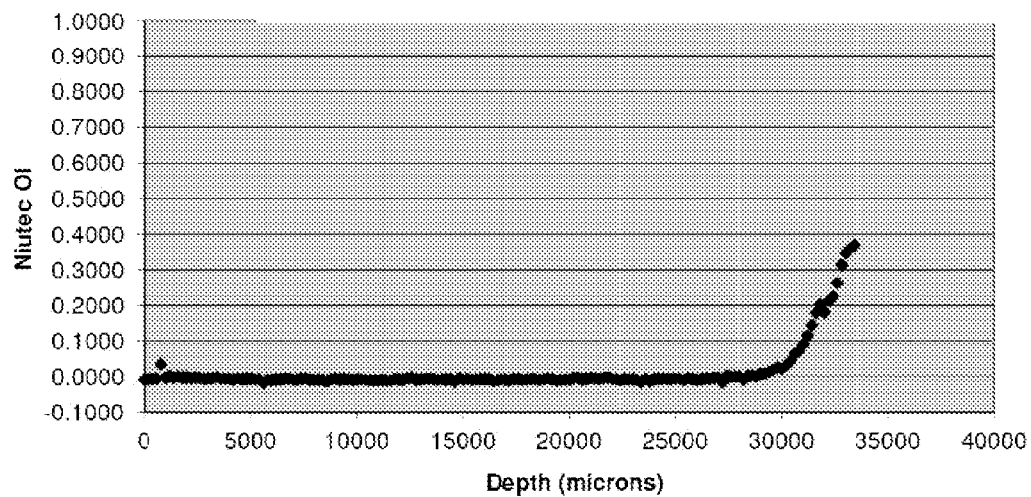
FIG. 9e illustrates oxidation index versus depth from middle to side of the sample of Example 5a, in accordance with various embodiments.
Figure 9F:
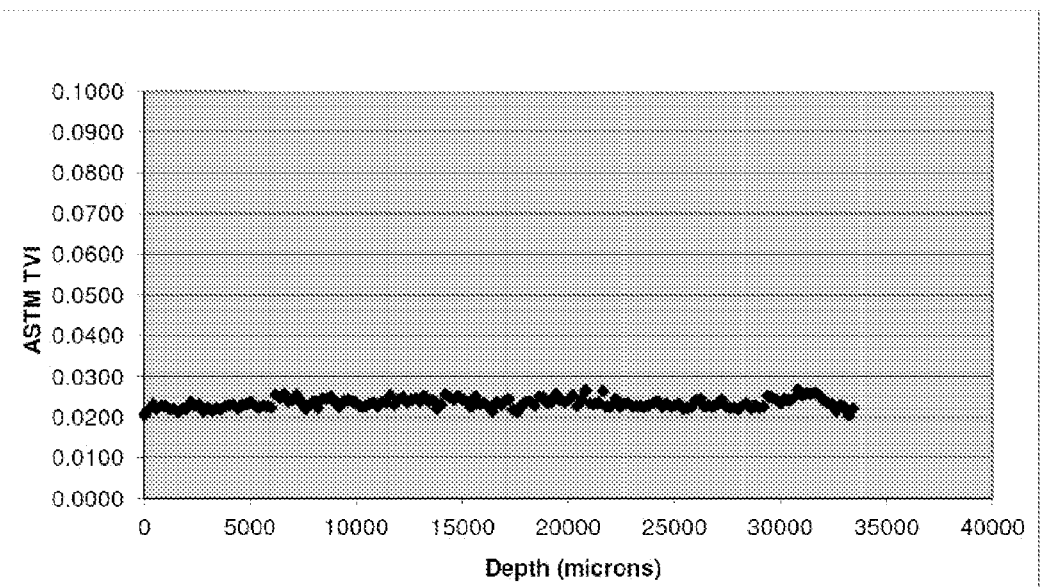
FIG. 9f illustrates trans-vinylene index versus depth from middle to side of the sample of Example 5a, in accordance with various embodiments.

FIG. 9a illustrates oxidation index versus depth from the top to the bottom of the sample of Example 5a. FIG. 9b illustrates trans-vinylene index versus depth from the top to the bottom of the sample of Example 5a. FIG. 9c illustrates oxidation index versus depth from side to middle of the sample of Example 5a. FIG. 9d illustrates trans-vinylene index versus depth from side to middle of the sample of Example 5a. FIG. 9e illustrates oxidation index versus depth from middle to side of the sample of Example 5a. FIG. 9f illustrates trans-vinylene index versus depth from middle to side of the sample of Example 5a.

Figure 10A:
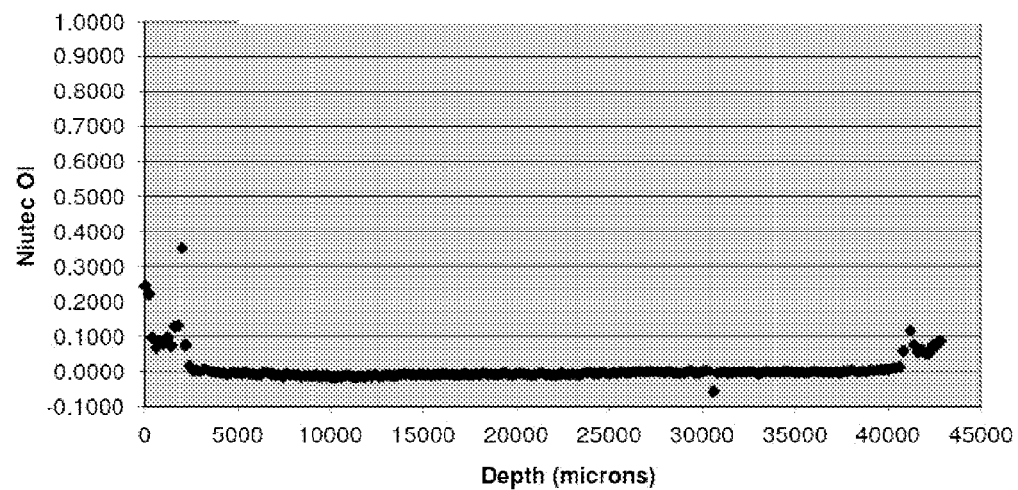
FIG. 10a illustrates oxidation index versus depth from the top to the bottom of the sample of Example 5b, in accordance with various embodiments.
Figure 10B:
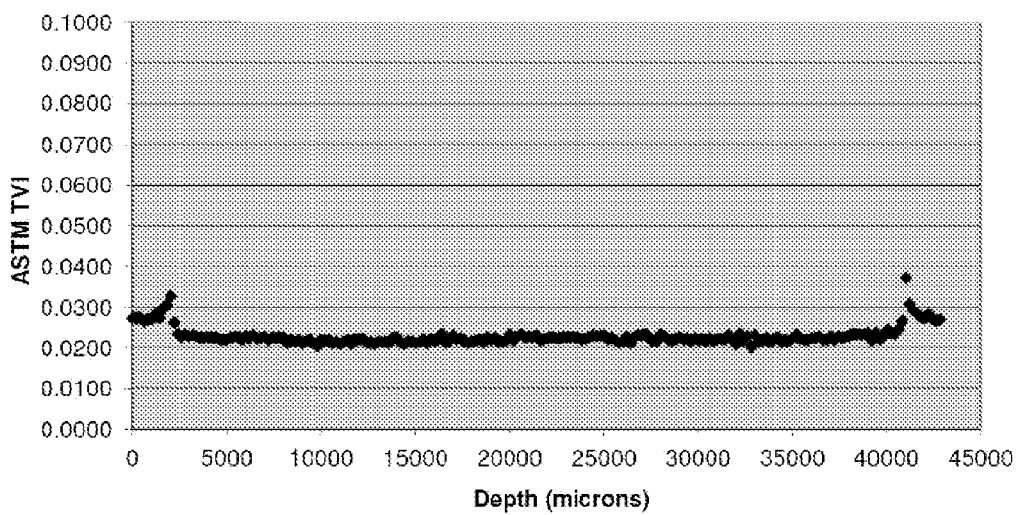
FIG. 10b illustrates trans-vinylene index versus depth from the top to the bottom of the sample of Example 5b, in accordance with various embodiments.
Figure 10C:
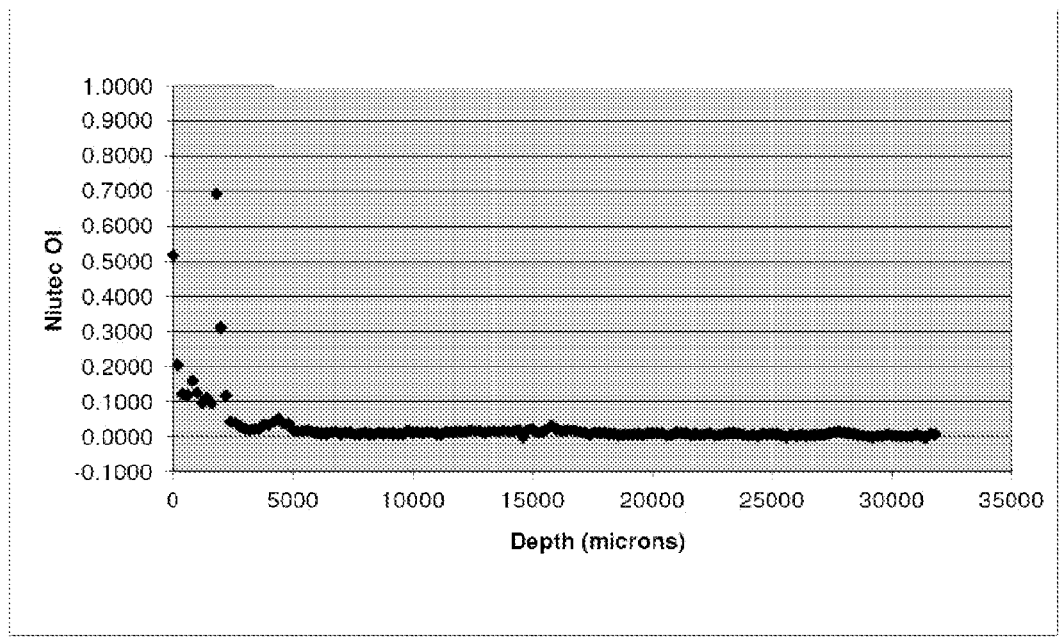
FIG. 10c illustrates oxidation index versus depth from side to middle of the sample of Example 5b, in accordance with various embodiments.
Figure 10D:
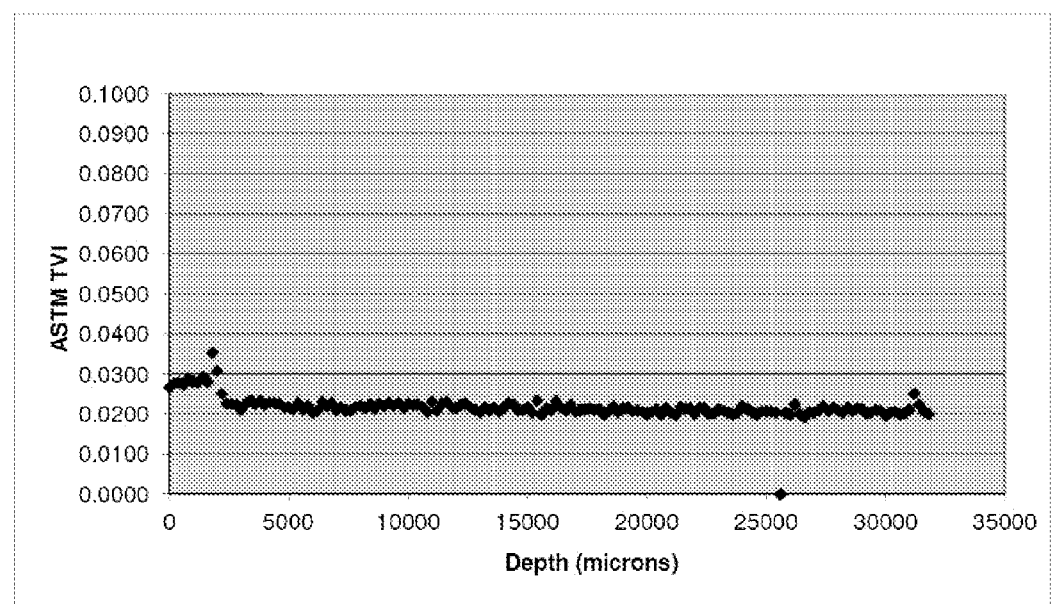
FIG. 10d illustrates trans-vinylene index versus depth from side to middle of the sample of Example 5b, in accordance with various embodiments.
Figure 10E:
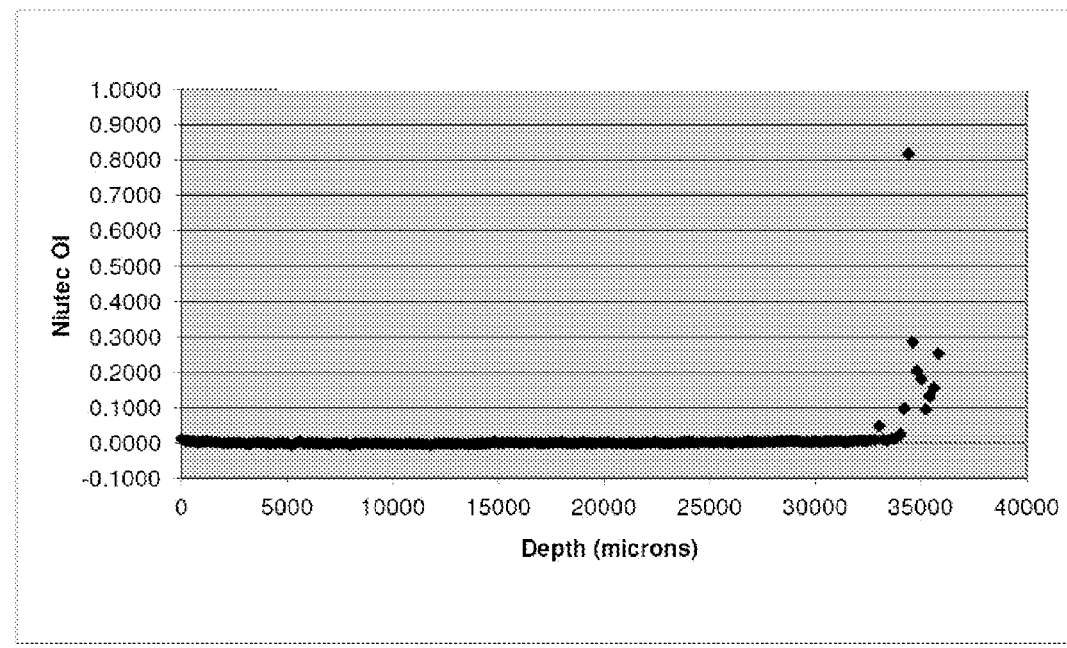
FIG. 10e illustrates oxidation index versus depth from middle to side of the sample of Example 5b, in accordance with various embodiments.
Figure 10F:
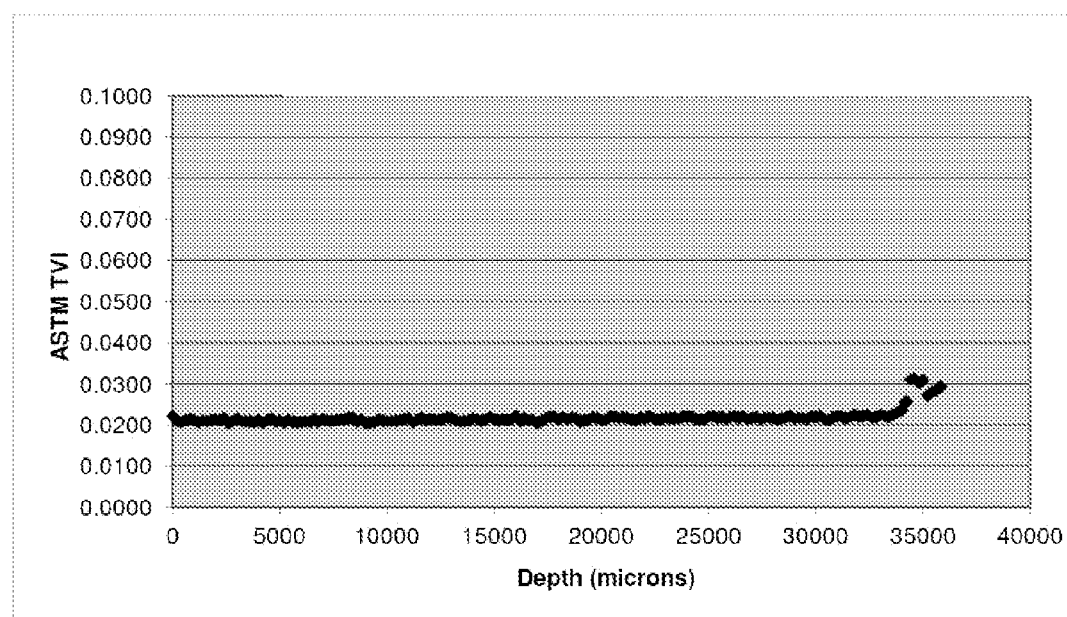
FIG. 10f illustrates trans-vinylene index versus depth from middle to side of the sample of Example 5b, in accordance with various embodiments.

FIG. 10a illustrates oxidation index versus depth from the top to the bottom of the sample of Example 5b. FIG. 10b illustrates trans-vinylene index versus depth from the top to the bottom of the sample of Example 5b. FIG. 10c illustrates oxidation index versus depth from side to middle of the sample of Example 5b. FIG. 10d illustrates trans-vinylene index versus depth from side to middle of the sample of Example 5b. FIG. 10e illustrates oxidation index versus depth from middle to side of the sample of Example 5b. FIG. 10f illustrates trans-vinylene index versus depth from middle to side of the sample of Example 5b.

Figure 11A:
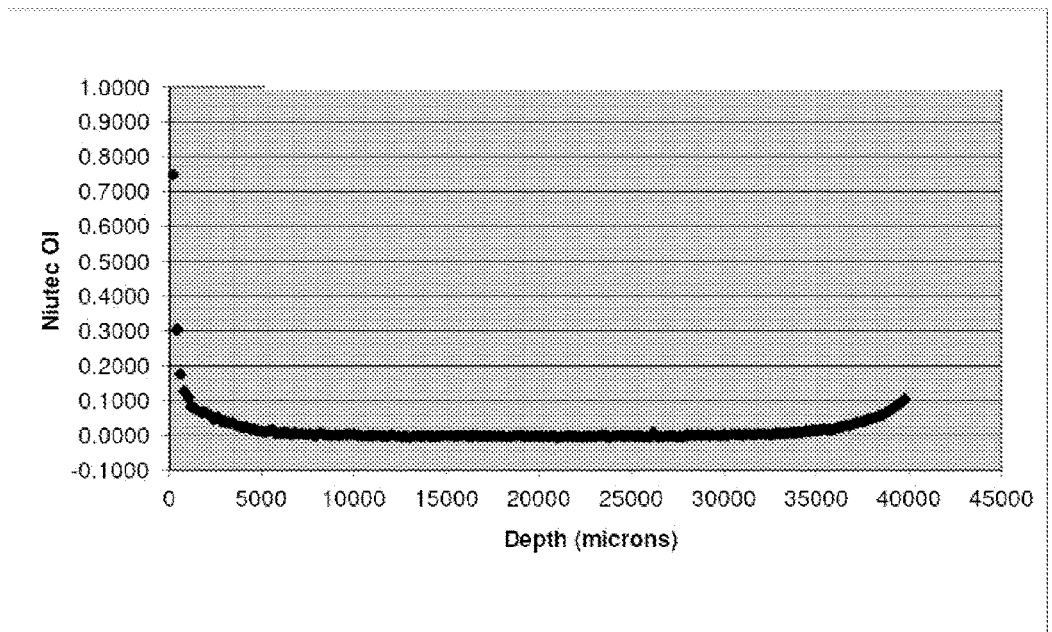
FIG. 11a illustrates oxidation index versus depth from the top to the bottom of the sample of Example 5c, in accordance with various embodiments.
Figure 11B:
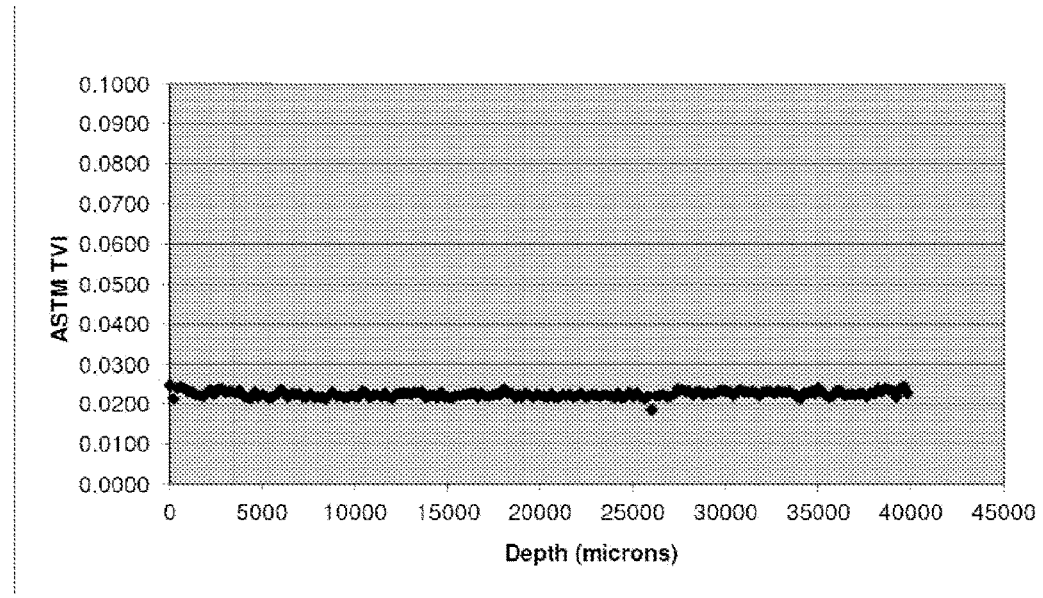
FIG. 11b illustrates trans-vinylene index versus depth from the top to the bottom of the sample of Example 5c, in accordance with various embodiments.
Figure 11C:
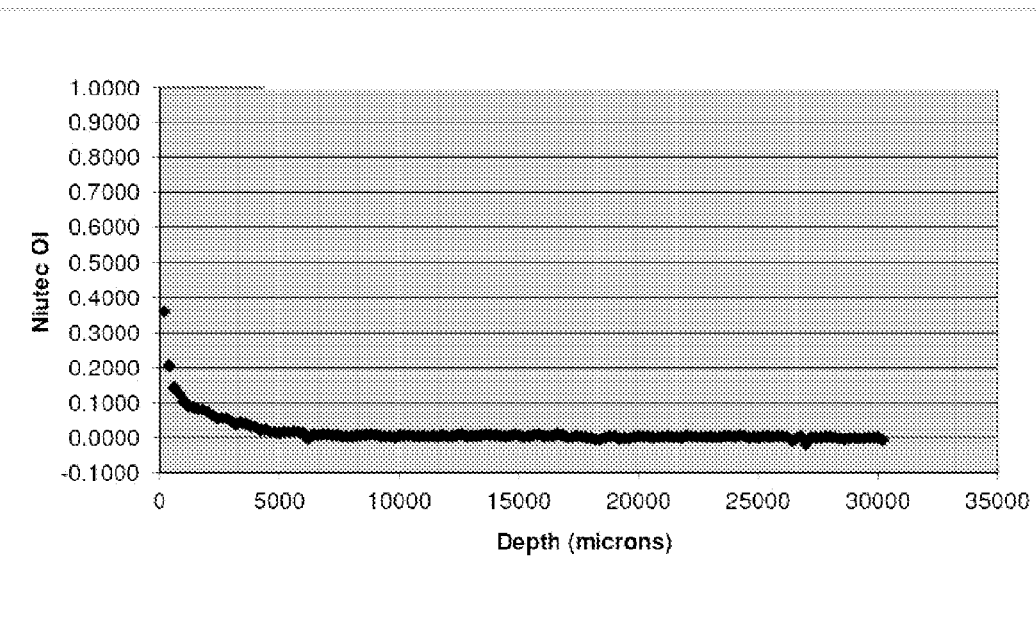
FIG. 11c illustrates oxidation index versus depth from side to middle of the sample of Example 5c, in accordance with various embodiments.
Figure 11D:
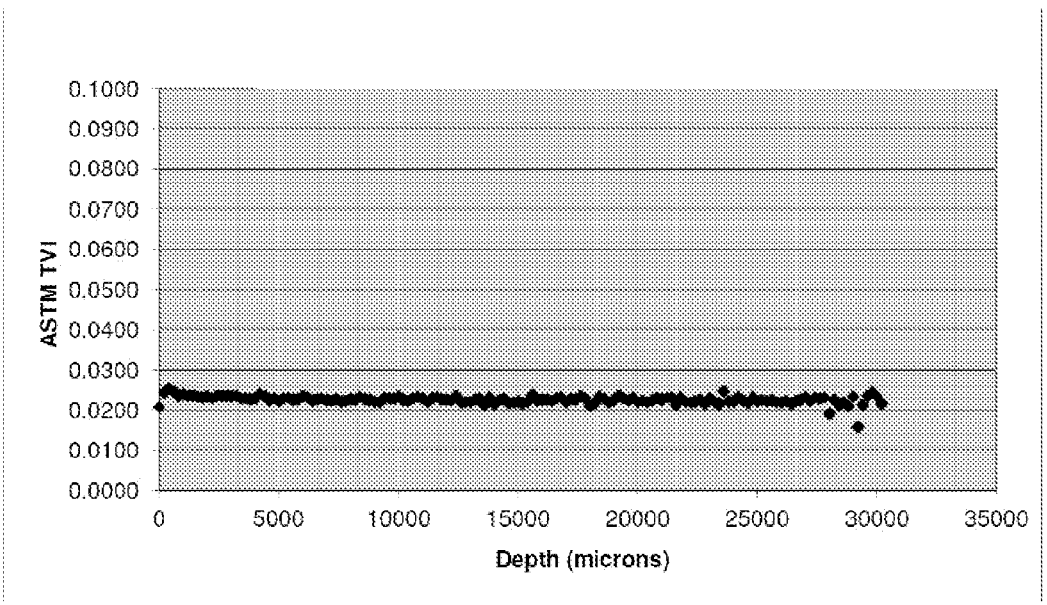
FIG. 11d illustrates trans-vinylene index versus depth from side to middle of the sample of Example 5c, in accordance with various embodiments.
Figure 11E:
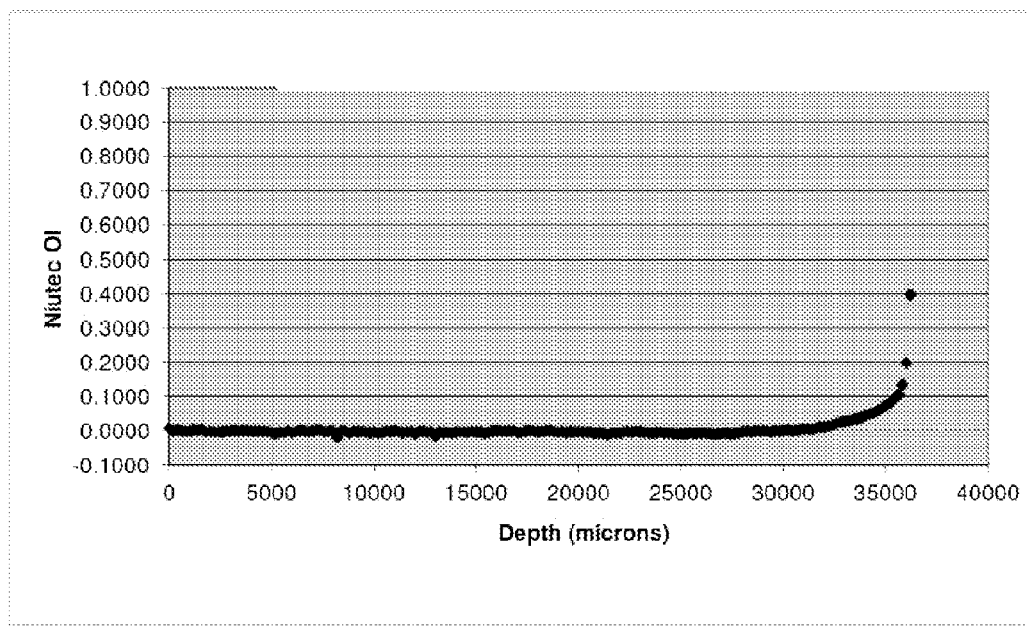
FIG. 11e illustrates oxidation index versus depth from middle to side of the sample of Example 5c, in accordance with various embodiments.
Figure 11F:
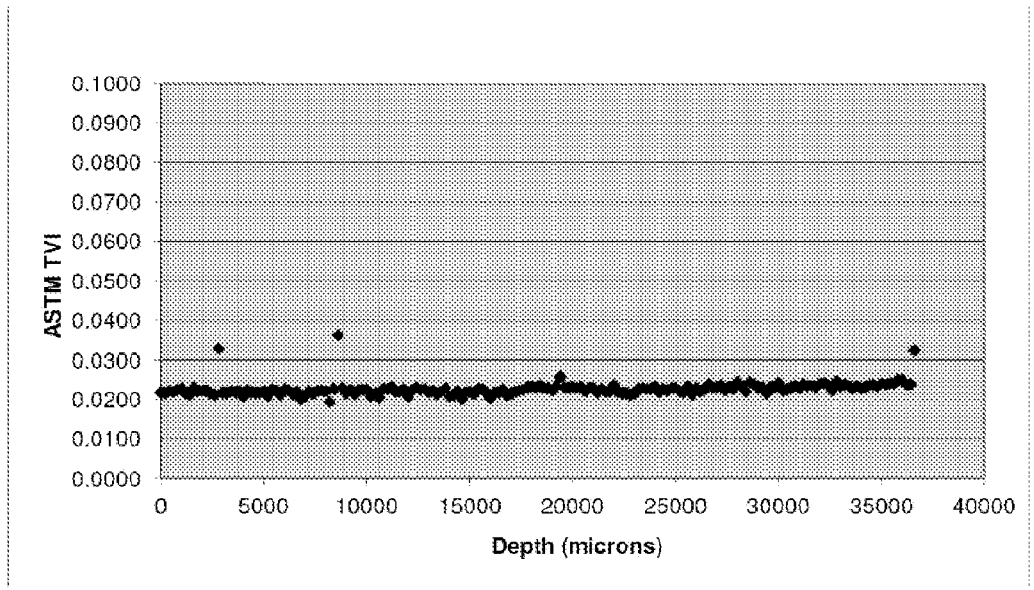
FIG. 11f illustrates trans-vinylene index versus depth from middle to side of the sample of Example 5c, in accordance with various embodiments.

FIG. 11a illustrates oxidation index versus depth from the top to the bottom of the sample of Example 5c. FIG. 11b illustrates trans-vinylene index versus depth from the top to the bottom of the sample of Example 5c. FIG. 11c illustrates oxidation index versus depth from side to middle of the sample of Example 5c. FIG. 11d illustrates trans-vinylene index versus depth from side to middle of the sample of Example 5c. FIG. 11e illustrates oxidation index versus depth from middle to side of the sample of Example 5c. FIG. 11f illustrates trans-vinylene index versus depth from middle to side of the sample of Example 5c.

Figure 12A:
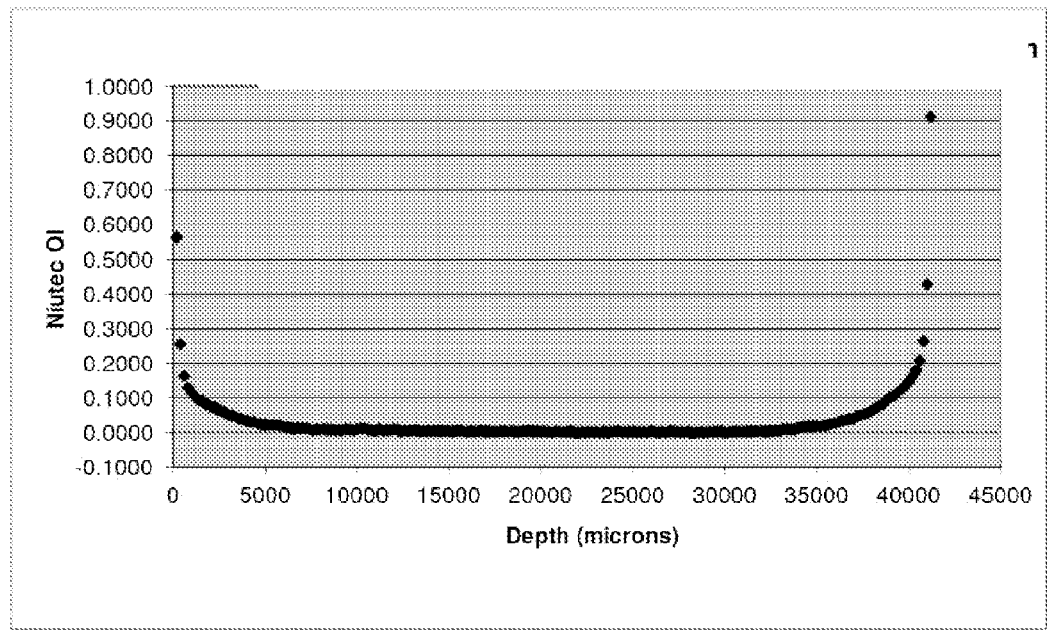
FIG. 12a illustrates oxidation index versus depth from the top to the bottom of the sample of Example 5d, in accordance with various embodiments.
Figure 12B:
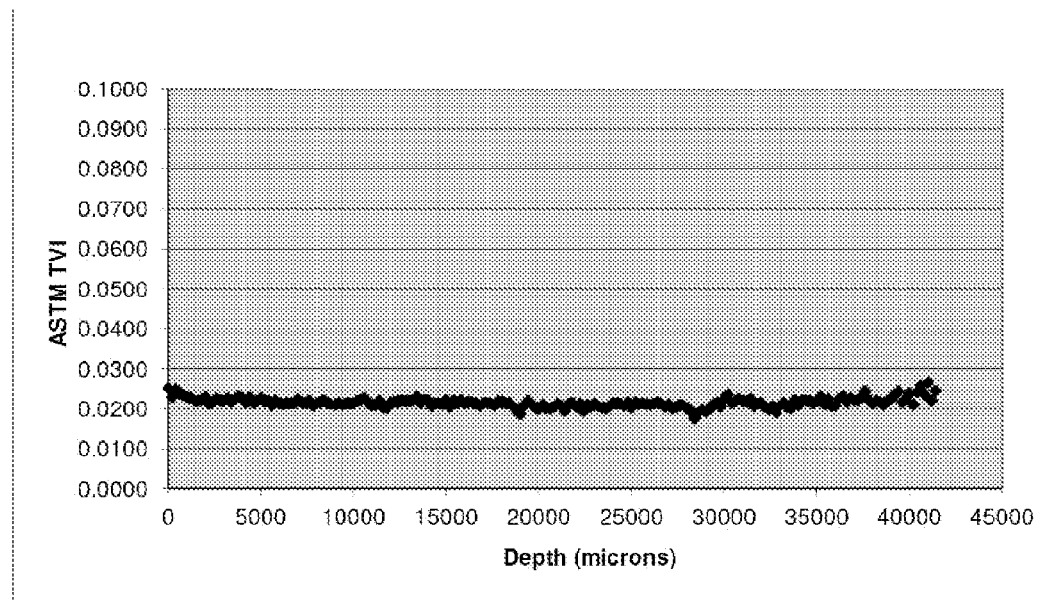
FIG. 12b illustrates trans-vinylene index versus depth from the top to the bottom of the sample of Example 5d, in accordance with various embodiments.
Figure 12C:
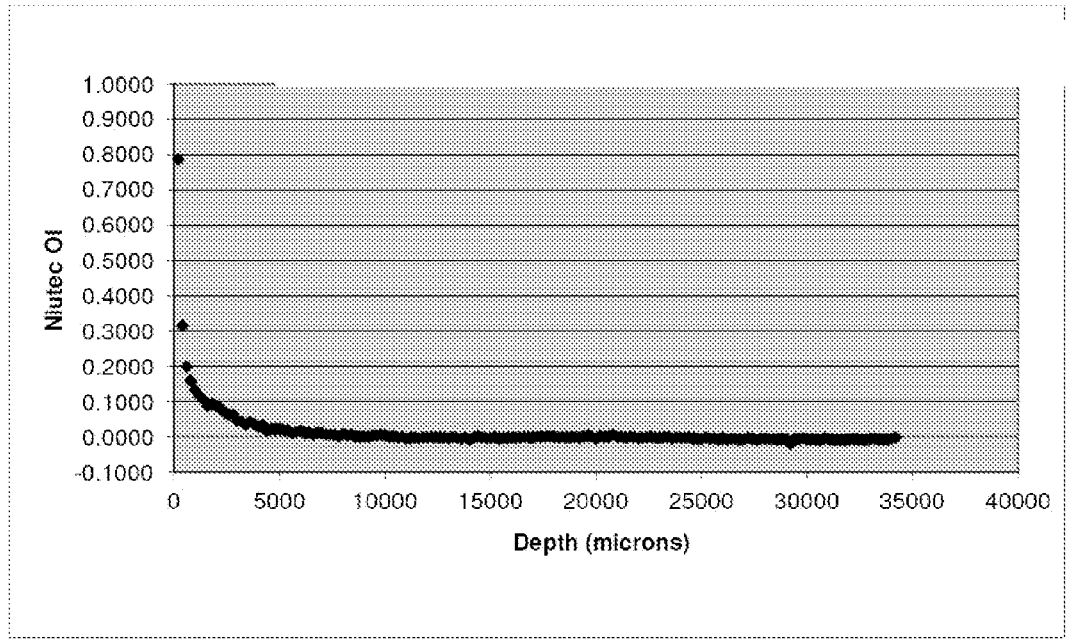
FIG. 12c illustrates oxidation index versus depth from side to middle of the sample of Example 5d, in accordance with various embodiments.
Figure 12D:
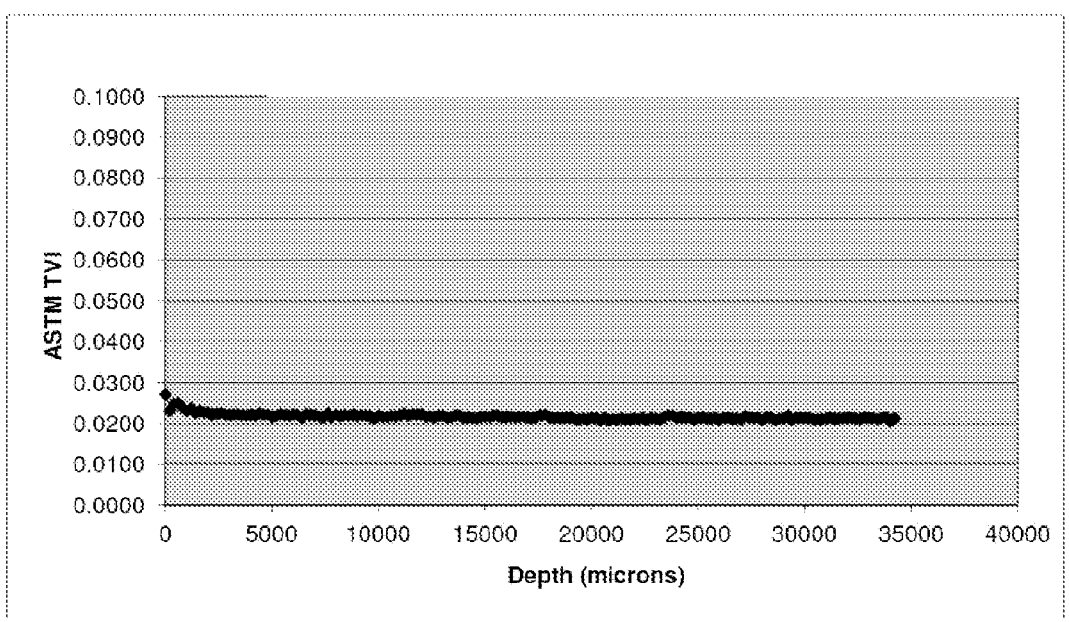
FIG. 12d illustrates trans-vinylene index versus depth from side to middle of the sample of Example 5d, in accordance with various embodiments.
Figure 12E:
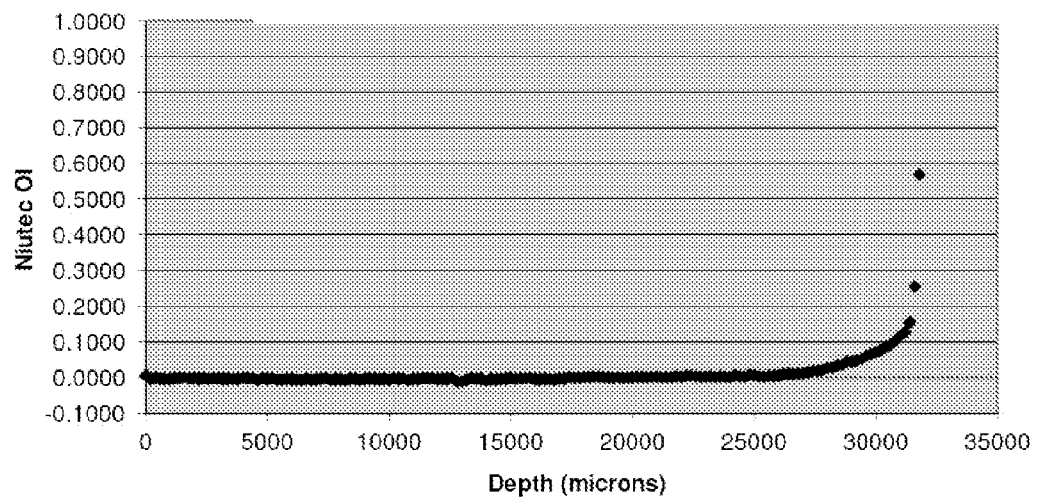
FIG. 12e illustrates oxidation index versus depth from middle to side of the sample of Example 5d, in accordance with various embodiments.
Figure 12F:
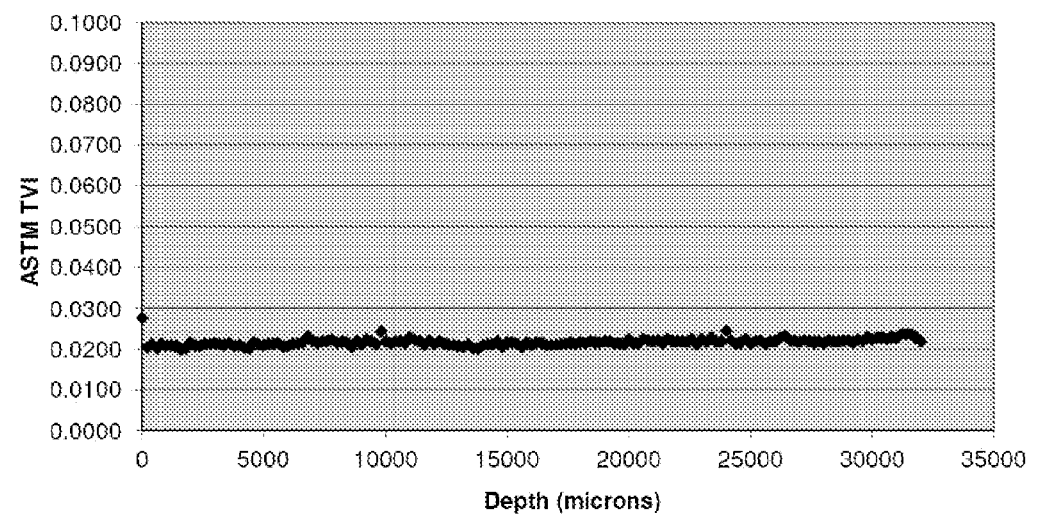
FIG. 12f illustrates trans-vinylene index versus depth from middle to side of the sample of Example 5d, in accordance with various embodiments.

FIG. 12a illustrates oxidation index versus depth from the top to the bottom of the sample of Example 5d. FIG. 12b illustrates trans-vinylene index versus depth from the top to the bottom of the sample of Example 5d. FIG. 12c illustrates oxidation index versus depth from side to middle of the sample of Example 5d. FIG. 12d illustrates trans-vinylene index versus depth from side to middle of the sample of Example 5d. FIG. 12e illustrates oxidation index versus depth from middle to side of the sample of Example 5d. FIG. 12f illustrates trans-vinylene index versus depth from middle to side of the sample of Example 5d.

Figure 13A:
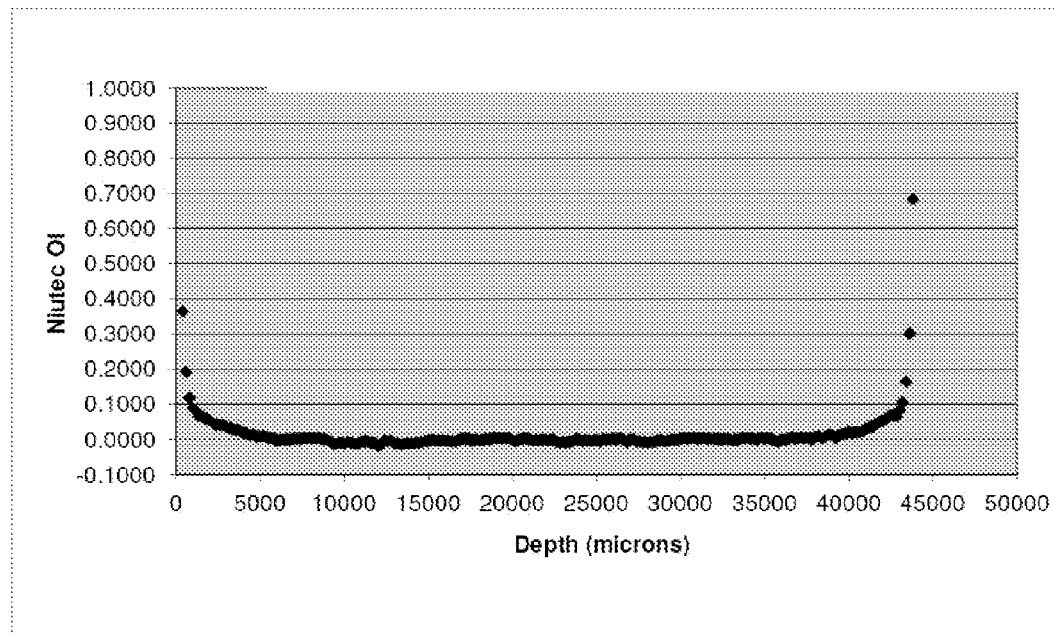
FIG. 13a illustrates oxidation index versus depth from the top to the bottom of the sample of Example 6a, in accordance with various embodiments.
Figure 13B:
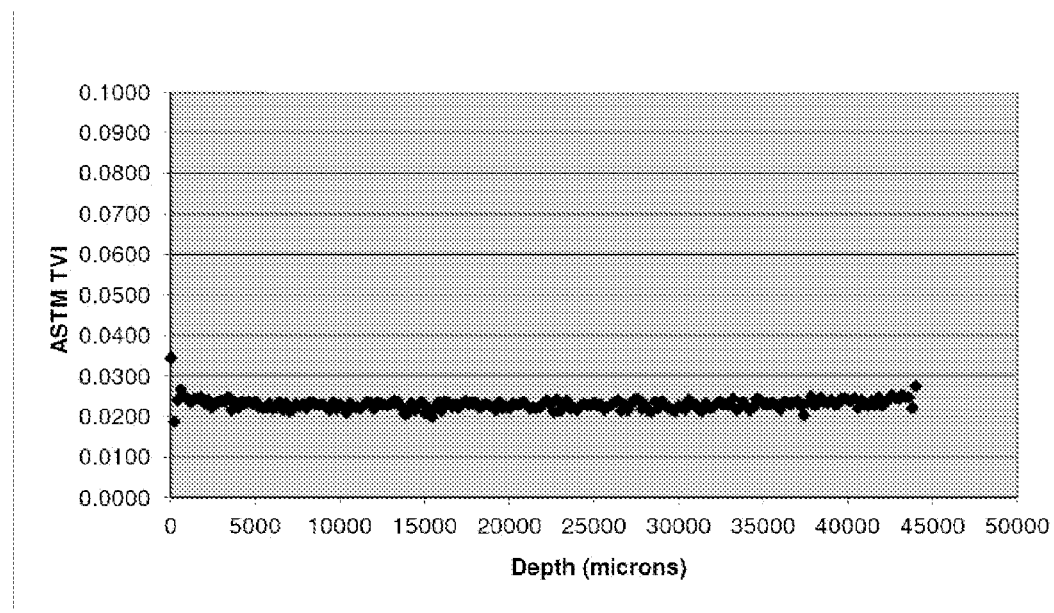
FIG. 13b illustrates trans-vinylene index versus depth from the top to the bottom of the sample of Example 6a, in accordance with various embodiments.
Figure 13C:
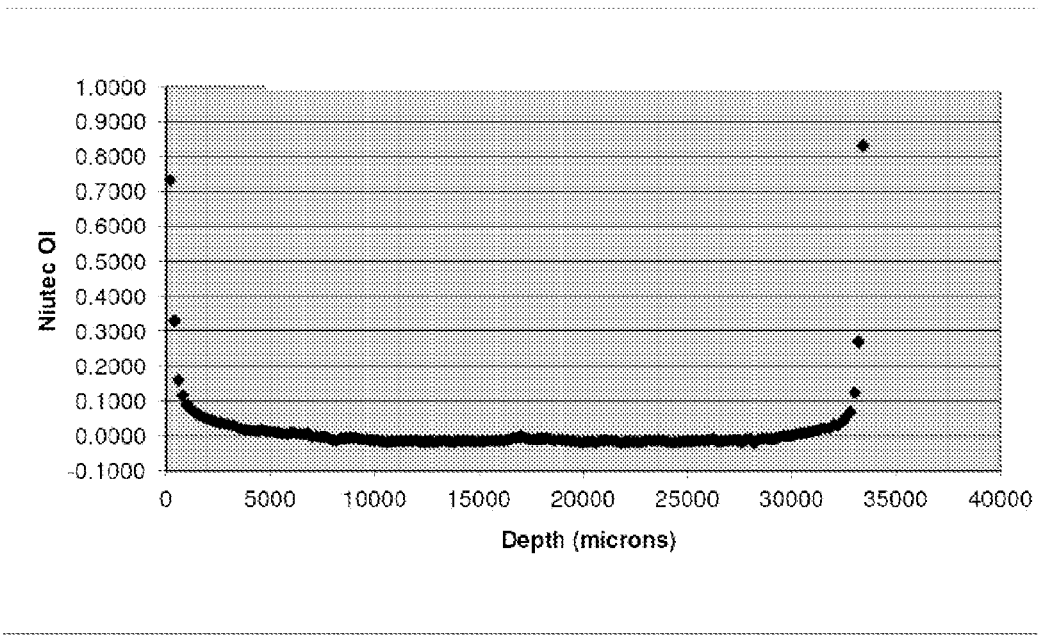
FIG. 13c illustrates oxidation index versus depth from side to side of the sample of Example 6a, in accordance with various embodiments.
Figure 13D:
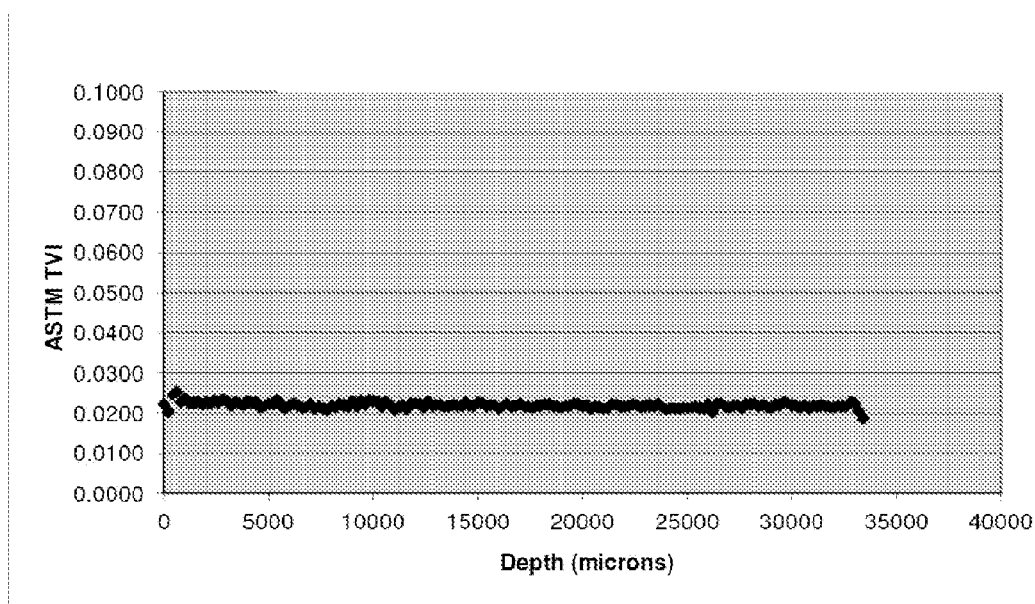
FIG. 13d illustrates trans-vinylene index versus depth from side to side of the sample of Example 6a, in accordance with various embodiments.

FIG. 13a illustrates oxidation index versus depth from the top to the bottom of the sample of Example 6a. FIG. 13b illustrates trans-vinylene index versus depth from the top to the bottom of the sample of Example 6a. FIG. 13c illustrates oxidation index versus depth from side to side of the sample of Example 6a. FIG. 13d illustrates trans-vinylene index versus depth from side to side of the sample of Example 6a.

Figure 14A:
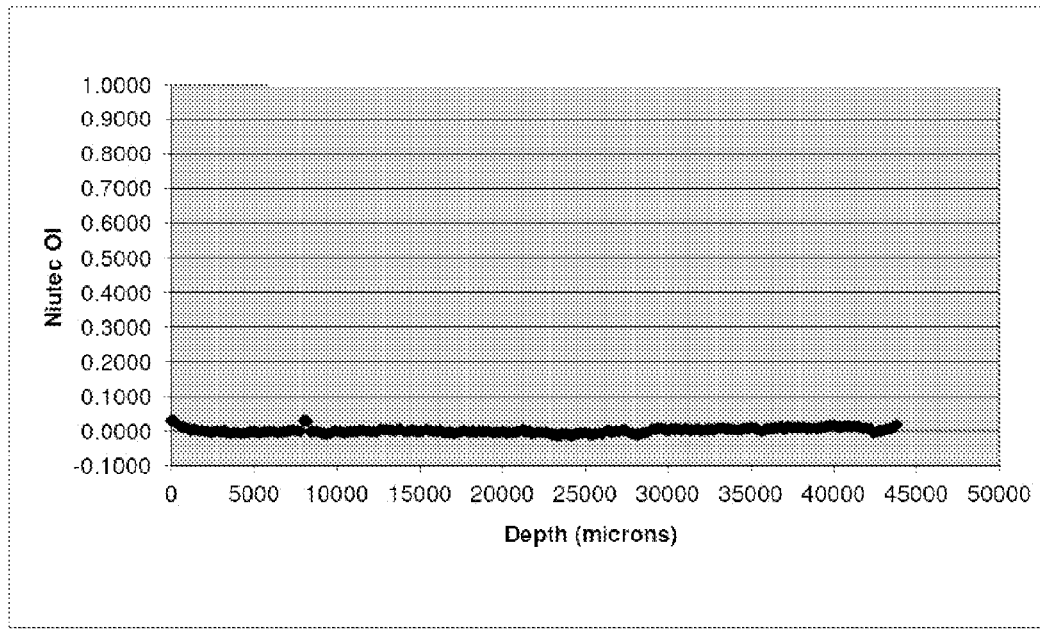
FIG. 14a illustrates oxidation index versus depth from the top to the bottom of the sample of Example 6b, in accordance with various embodiments.
Figure 14B:
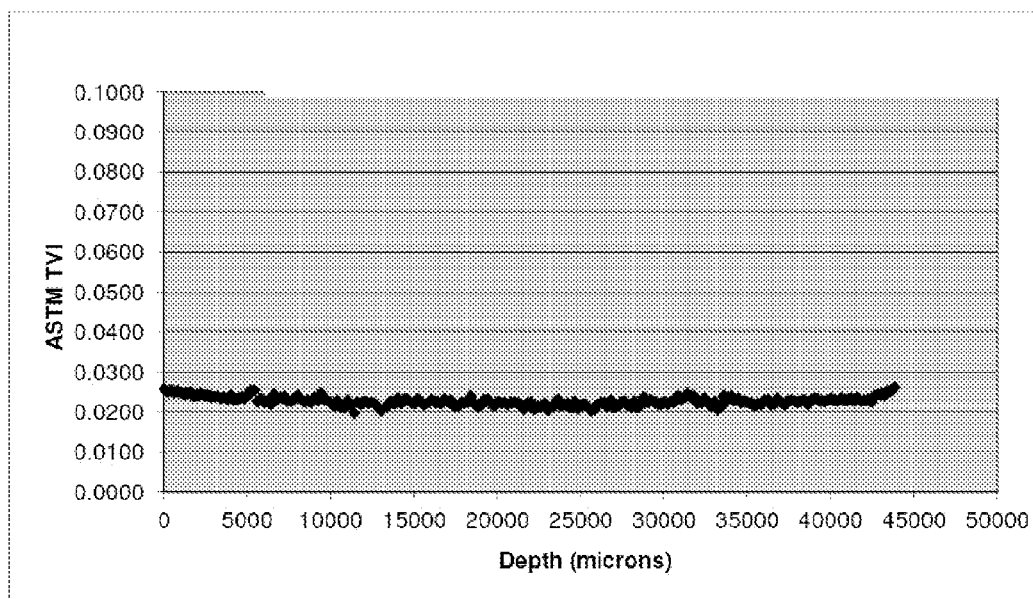
FIG. 14b illustrates trans-vinylene index versus depth from the top to the bottom of the sample of Example 6b, in accordance with various embodiments.
Figure 14C:
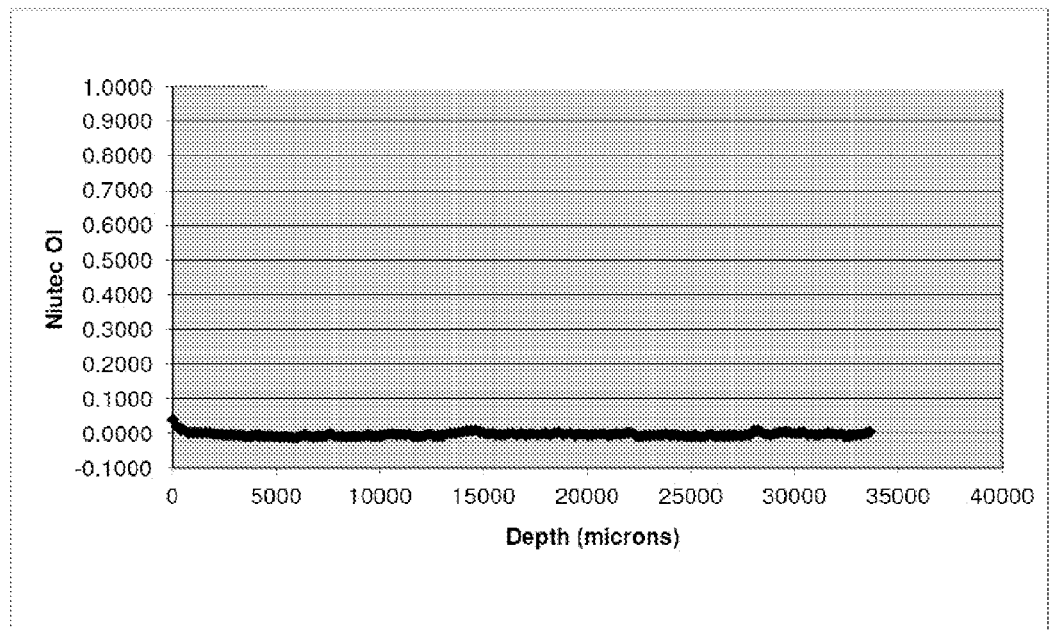
FIG. 14c illustrates oxidation index versus depth from side to side of the sample of Example 6b, in accordance with various embodiments.
Figure 14D:
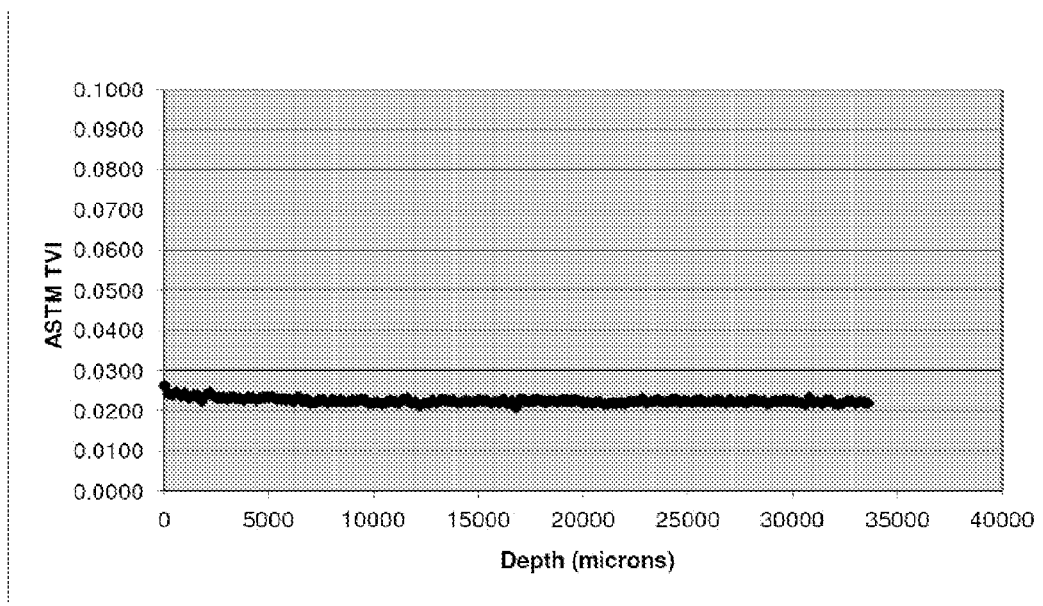
FIG. 14d illustrates trans-vinylene index versus depth from side to side of the sample of Example 6b, in accordance with various embodiments.

FIG. 14a illustrates oxidation index versus depth from the top to the bottom of the sample of Example 6b. FIG. 14b illustrates trans-vinylene index versus depth from the top to the bottom of the sample of Example 6b. FIG. 14c illustrates oxidation index versus depth from side to side of the sample of Example 6b. FIG. 14d illustrates trans-vinylene index versus depth from side to side of the sample of Example 6b.

Figure 15A:
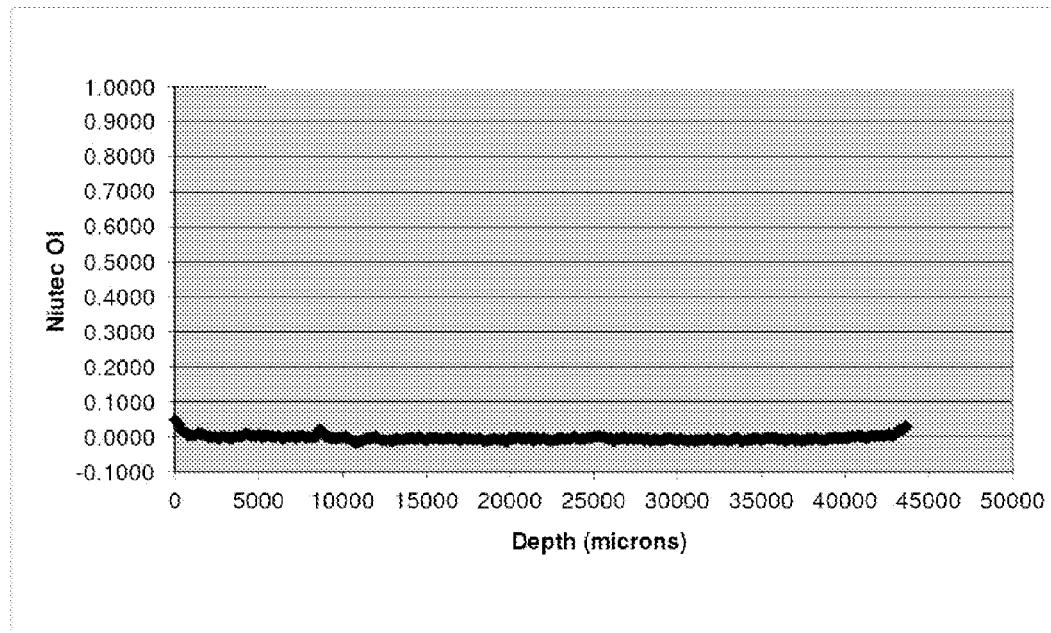
FIG. 15a illustrates oxidation index versus depth from the top to the bottom of the sample of Example 6c, in accordance with various embodiments.
Figure 15B:
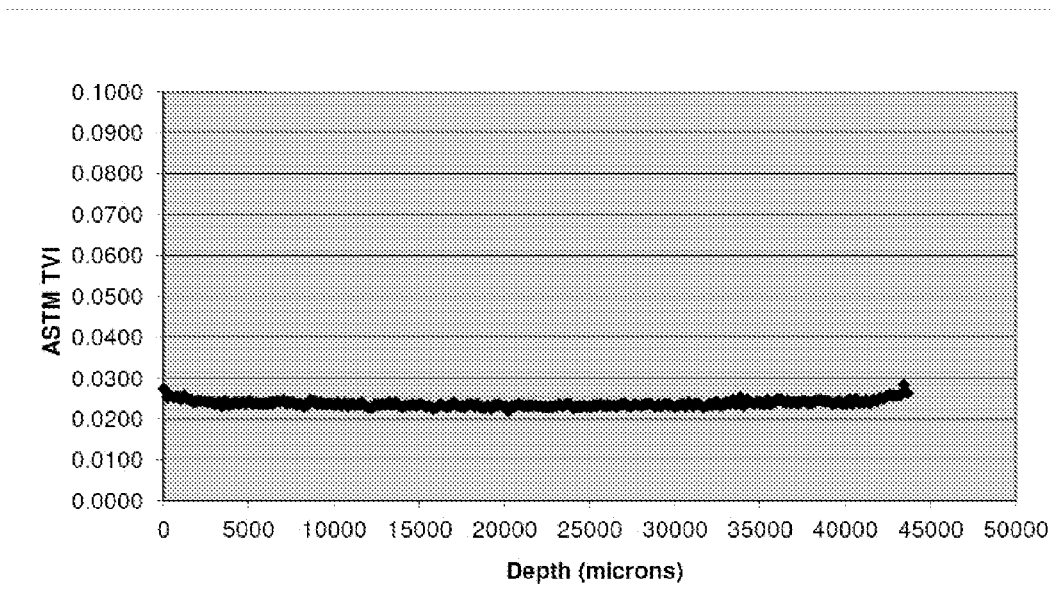
FIG. 15b illustrates trans-vinylene index versus depth from the top to the bottom of the sample of Example 6c, in accordance with various embodiments.
Figure 15C:
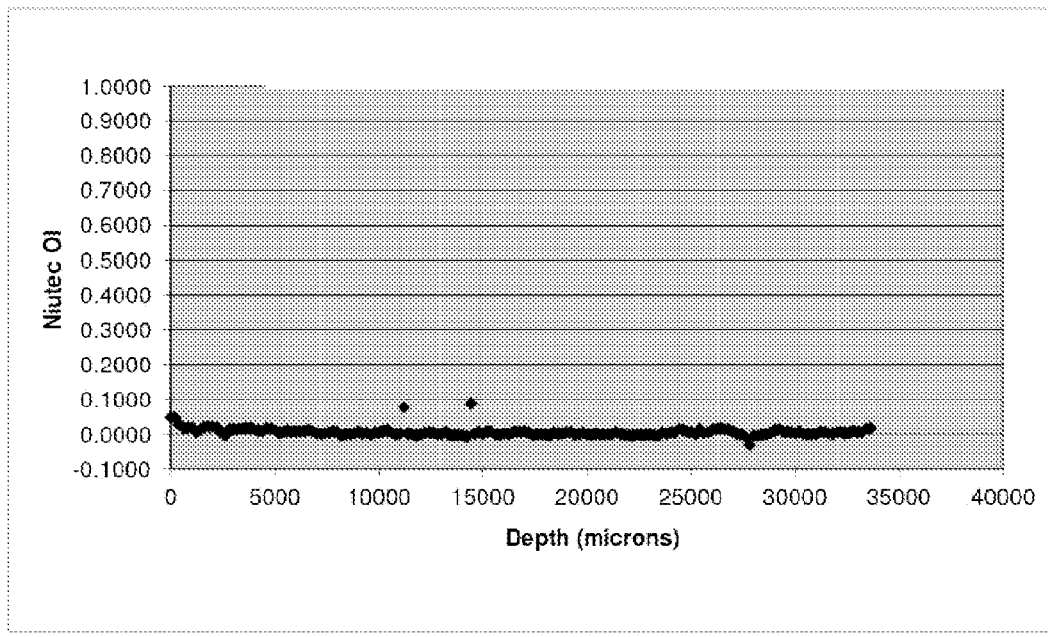
FIG. 15c illustrates oxidation index versus depth from side to side of the sample of Example 6c, in accordance with various embodiments.
Figure 15D:
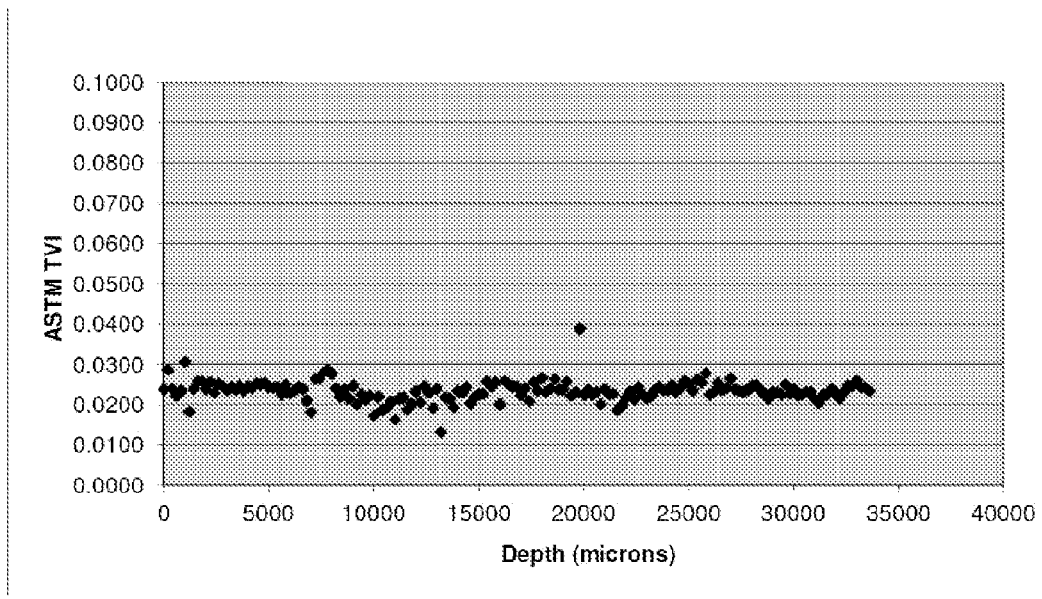
FIG. 15d illustrates trans-vinylene index versus depth from side to side of the sample of Example 6c, in accordance with various embodiments.

FIG. 15a illustrates oxidation index versus depth from the top to the bottom of the sample of Example 6c. FIG. 15b illustrates trans-vinylene index versus depth from the top to the bottom of the sample of Example 6c. FIG. 15c illustrates oxidation index versus depth from side to side of the sample of Example 6c. FIG. 15d illustrates trans-vinylene index versus depth from side to side of the sample of Example 6c.

Figure 16A:
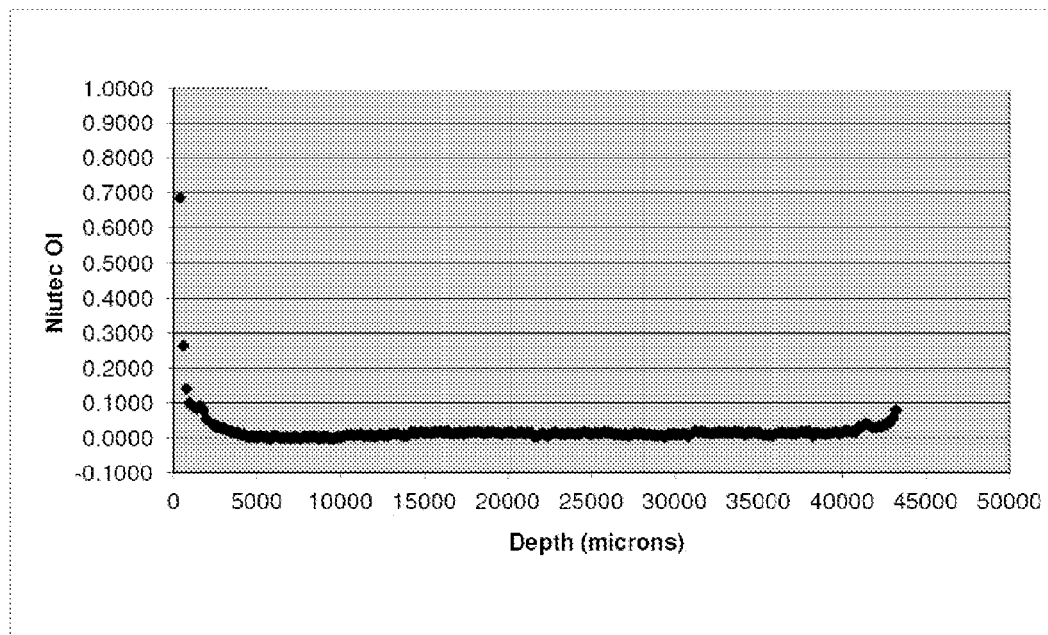
FIG. 16a illustrates oxidation index versus depth from the top to the bottom of the sample of Example 6d, in accordance with various embodiments.
Figure 16B:
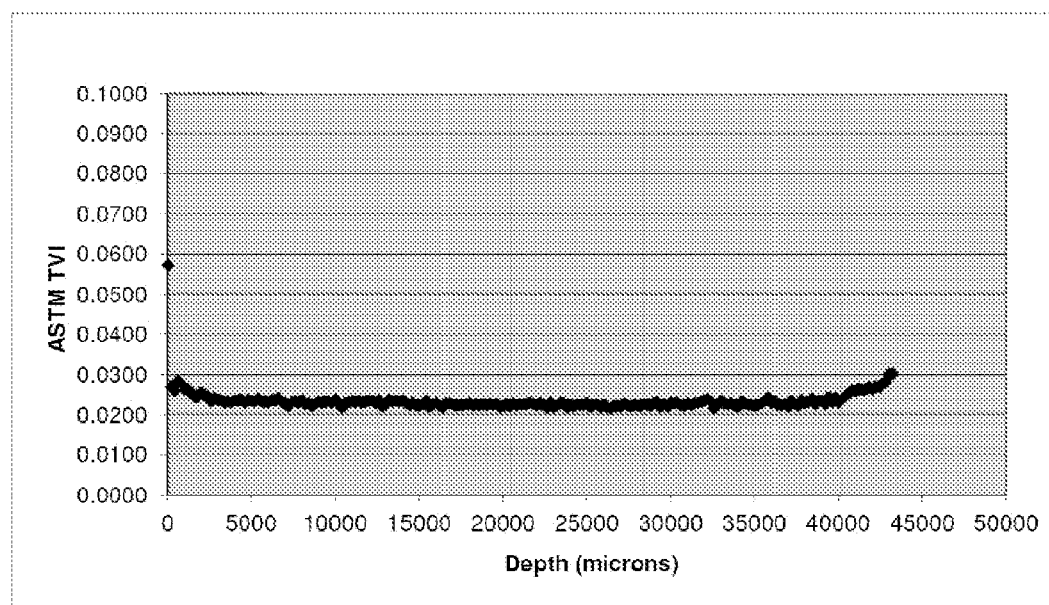
FIG. 16b illustrates trans-vinylene index versus depth from the top to the bottom of the sample of Example 6d, in accordance with various embodiments.
Figure 16C:
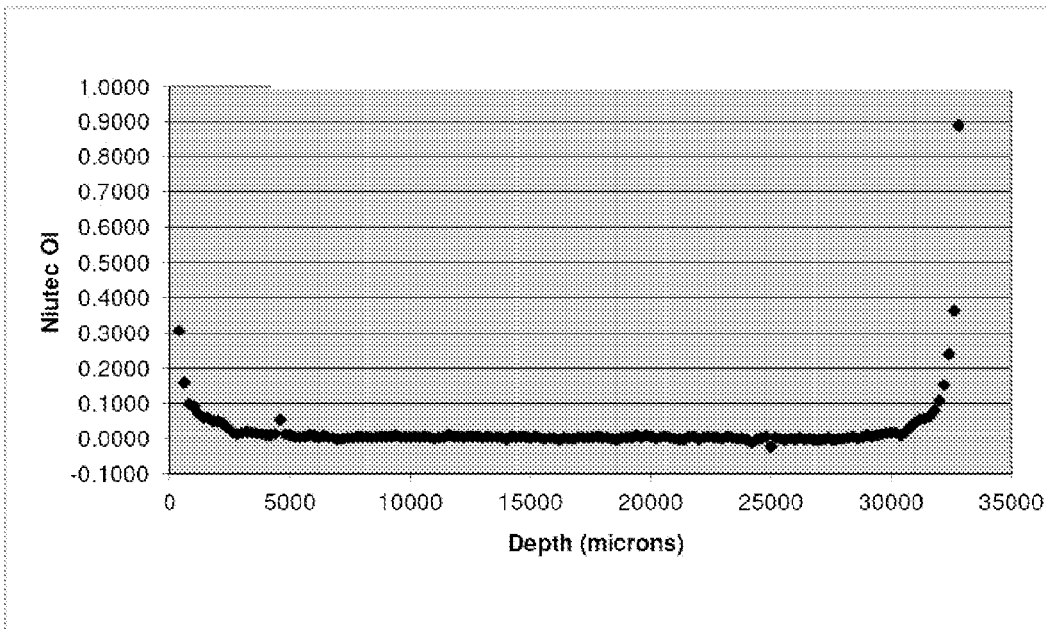
FIG. 16c illustrates oxidation index versus depth from side to side of the sample of Example 6d, in accordance with various embodiments.
Figure 16D:
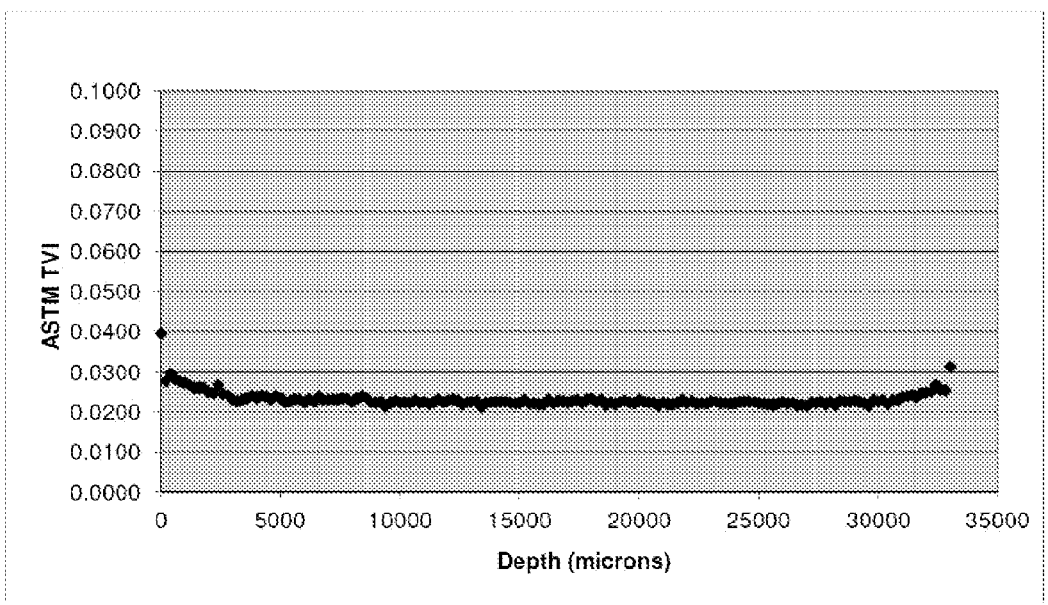
FIG. 16d illustrates trans-vinylene index versus depth from side to side of the sample of Example 6d, in accordance with various embodiments.

FIG. 16a illustrates oxidation index versus depth from the top to the bottom of the sample of Example 6d. FIG. 16b illustrates trans-vinylene index versus depth from the top to the bottom of the sample of Example 6d. FIG. 16c illustrates oxidation index versus depth from side to side of the sample of Example 6d. FIG. 16d illustrates trans-vinylene index versus depth from side to side of the sample of Example 6d.

Example 8

Oxidation Induction Time

Oxidation Induction Time (OIT) is used to determine the activity and amount of antioxidant present in a polymeric material such as UHMWPE. OIT was determined in the specimens from examples 4 and 5 using a differential scanning calorimeter per ASTM D3895-07. As per ASTM D3895-07, firms were microtomed from the block of material at 200-250 micron thickness. Specimens were punched from the film for testing and were typically between 5 and 10 mg weight. The specimen was placed in the DSC pan and heated to 200° C. under nitrogen purge for 60 minutes, then the gas was switched to oxygen, and the time for exotherm due to oxidation was determined, with the onset time being determined from the DSC plot of heat flow (W/g) versus time as the time at the intersection of the baseline (e.g., regression line) to the tangent of the exotherm curve at its steepest slope. OIT was determined as onset time minus the time that oxygen flow began.

Specimens, 6.4 mm diameter and 200-250 micron thick, were taken as close as possible to outer edge near the center of each face, and near the geometric center of the block. The results are given in Table 2.

TABLE 2

Oxidation induction time results for Example 8.

| Sample | ID | Start of oxygen purge (min) | Onset Method (min) | OIT (Onset) |
|---|---|---|---|---|
| 4a | Top Edge | 18.50 | 27.59 | 9.09 |
| | Center | 18.50 | 18.76 | 0.26 |
| | Bottom Edge | 18.50 | 29.48 | 10.98 |
| | Side 1 Edge | 18.50 | 33.33 | 14.83 |
| | Side 2 Edge | 18.50 | 25.45 | 6.95 |
| 4b | Top Edge | 18.50 | 24.00 | 5.50 |
| | Center | 18.50 | 18.81 | 0.31 |
| | Bottom Edge | 18.50 | 28.13 | 9.63 |
| | Side 1 Edge | 18.50 | 25.54 | 7.04 |
| | Side 2 Edge | 18.50 | 21.95 | 3.45 |
| 4c | Top Edge | 18.50 | 20.94 | 2.44 |
| | Center | 18.50 | 18.78 | 0.28 |
| | Bottom Edge | 18.50 | 24.62 | 6.12 |

TABLE 2-continued

Oxidation induction time results for Example 8.

| Sample | ID | Start of oxygen purge (min) | Onset Method (min) | OIT (Onset) |
|---|---|---|---|---|
| | Side 1 Edge | 18.50 | 21.77 | 3.27 |
| | Side 2 Edge | 18.50 | 20.24 | 1.74 |
| 4d | Top Edge | 18.50 | 21.17 | 2.67 |
| | Center | 18.50 | 18.77 | 0.27 |
| | Bottom Edge | 18.50 | 21.97 | 3.47 |
| | Side 1 Edge | 18.50 | 22.21 | 3.71 |
| | Side 2 Edge | 18.50 | 21.83 | 3.33 |
| 4e | Top Edge | 18.50 | 18.72 | 0.22 |
| | Center | 18.50 | 18.79 | 0.29 |
| | Bottom Edge | 18.50 | 18.73 | 0.23 |
| | Side 1 Edge | 18.50 | 18.69 | 0.19 |
| | Side 2 Edge | 18.50 | 18.71 | 0.21 |
| 5a | Edge 1 | 18.50 | 19.38 | 0.88 |
| | Edge 2 | 18.50 | 20.60 | 2.10 |
| | Edge 3 | 18.50 | 20.62 | 2.12 |
| | Center 1 | 18.50 | 18.81 | 0.31 |
| | Center 2 | 18.50 | 18.81 | 0.31 |
| 5b | Edge 1 | 18.50 | 18.71 | 0.21 |
| | Edge 2 | 18.50 | 18.71 | 0.21 |
| | Edge 3 | 18.50 | 18.73 | 0.23 |
| | Center 1 | 18.50 | 18.80 | 0.30 |
| | Center 2 | 18.50 | 18.84 | 0.34 |
| 5c | Edge 1 | 18.50 | 18.74 | 0.24 |
| | Edge 2 | 18.50 | 18.73 | 0.23 |
| | Edge 3 | 18.50 | 18.74 | 0.24 |
| | Center 1 | 18.50 | 18.79 | 0.29 |
| | Center 2 | 18.50 | 18.82 | 0.32 |
| 5d | Edge 1 | 18.50 | 18.73 | 0.23 |
| | Edge 2 | 18.50 | 18.74 | 0.24 |
| | Edge 3 | 18.50 | 18.72 | 0.22 |
| | Center 1 | 18.50 | 18.79 | 0.29 |
| | Center 2 | 18.50 | 18.81 | 0.31 |

Example 9

Weight Gain after Antioxidant Treatment

The blocks in Example 6 were weighed on a calibrated analytical balance with resolution to 0.000.1 grams, before and after antioxidant treatment. Weight gain of the blocks in Example 6 was determined after application of the antioxidant materials. Blocks were approximately 1.75×1.375×1.375 inches (4.45×3.5×3.5 cm). The weight of the blocks was determined to the nearest 0.001 grams before application of the antioxidant solution. The original weight was then used to estimate the approximate surface area of the block, with height known to be 1.75 inches, and widths estimated to be approximately equal, and with density equal to 0.935 g/cc. Weight of antioxidant applied was reported in absolute weight gain as well as weight per approximate surface area. The results are given in Table 3.

TABLE 3

Weight gain for Example 9, 4.45 cm high blocks.

| No. | Block weight (g) | Block + antioxidant (g) | Weight Antioxidant (g) | Height (cm) | Density (g/cm$^3$) | Volume (cm$^3$) | Width × width, (cm$^2$) | Width (cm) | Estimated block surface area (cm$^3$) | Weight per surface area (est) (g/cm$^2$) |
|---|---|---|---|---|---|---|---|---|---|---|
| 6a | 49.7244 | — | — | 4.445 | 0.935 | 53.181 | 11.964 | 3.46 | 85.428 | — |
| 6b | 43.7357 | 43.8694 | 0.1337 | 4.445 | 0.935 | 46.776 | 10.523 | 3.24 | 78.724 | 0.0017 |
| 6c | 51.2104 | 51.2460 | 0.0356 | 4.445 | 0.935 | 54.770 | 12.322 | 3.51 | 87.056 | 0.0004 |
| 6d | 45.0310 | 45.1472 | 0.1162 | 4.445 | 0.935 | 48.161 | 10.835 | 3.29 | 80.196 | 0.0014 |

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The following exemplary embodiments are provided, the numbering of which is not to be construed as designating levels of importance:

Embodiment 1 provides a method of melt-stabilizing a material comprising ultra high molecular weight polyethylene (UHMWPE), the method comprising:

obtaining or providing a solid material comprising UHMWPE comprising a first concentration of free-radicals;

coating at least part of the solid material with a liquid composition comprising at least one antioxidant, to provide a coated solid material;

heating the coated solid material in an environment comprising oxygen, the heating sufficient to melt at least part of the UHMWPE, to provide a heated material; and solidifying the heated material, to provide a melt-stabilized material comprising UHMWPE comprising a second concentration of free-radicals, wherein the second concentration of free-radicals is less than the first concentration of free-radicals.

Embodiment 2 provides the method of Embodiment 1, wherein the first concentration of free-radicals is at least about $1 \times 10^{15}$ spins/g.

Embodiment 3 provides the method of any one of Embodiments 1-2, wherein the first concentration of free-radicals is about $1 \times 10^{15}$ spins/gram to about $1 \times 10^{20}$ spins/g.

Embodiment 4 provides the method of any one of Embodiments 1-3, wherein the second concentration of free-radicals is less than about $1 \times 10^{15}$ spins/g.

Embodiment 5 provides the method of any one of Embodiments 1-4, wherein the second concentration of free-radicals is about $1 \times 10^{5}$ spins/g to about $1 \times 10^{15}$ spins/g.

Embodiment 6 provides the method of any one of Embodiments 1-5, wherein the second concentration of free-radicals is about 1% to about 0.000.1% of the first concentration of free-radicals.

Embodiment 7 provides the method of any one of Embodiments 1-6, wherein the second concentration of free-radicals is about 0.1% to about 0.001% of the first concentration of free-radicals.

Embodiment 8 provides the method of any one of Embodiments 1-7, wherein the UHMWPE in a surface layer of the melt-stabilized material has an oxidation index that does not exceed 1.

Embodiment 9 provides the method of Embodiment 8, wherein the surface layer of the melt-stabilized material has an oxidation index of about 0.001 to about 1.

Embodiment 10 provides the method of any one of Embodiments 8-9, wherein the surface layer comprises a layer about 0 mm deep.

Embodiment 11 provides the method of any one of Embodiments 8-10, wherein the surface layer comprises a layer about 0 mm deep.

Embodiment 12 provides the method of any one of Embodiments 8-11, wherein the surface layer comprises a layer of about 0 mm deep and about 1 mm deep.

Embodiment 13 provides the method of any one of Embodiments 8-12, wherein the surface layer comprises a layer of about 0 mm deep and about 10 mm deep.

Embodiment 14 provides the method of any one of Embodiments 1-13, wherein coating at least part of the solid material with the liquid composition comprises coating about 1% to about 100% of a surface of the solid material.

Embodiment 15 provides the method of any one of Embodiments 1-14, wherein coating at least part of the solid material with the liquid composition comprises coating about 90% to about 100% of a surface of the solid material.

Embodiment 16 provides the method of any one of Embodiments 1-15, wherein the coating is sufficient to contact at least some of the UHMWPE and the liquid composition.

Embodiment 17 provides the method of any one of Embodiments 1-16, wherein the coating is sufficient to penetrate a surface layer of the solid material.

Embodiment 18 provides the method of Embodiment 17, wherein the surface layer comprises a layer of about 0 mm deep and about 1 mm deep.

Embodiment 19 provides the method of any one of Embodiments 17-18, wherein the surface layer comprises a layer of about 0 mm deep and about 10 mm deep.

Embodiment 20 provides the method of any one of Embodiments 1-19, wherein the coating is sufficient to provide a weight gain of about 0.000.01 g/cm² surface area to about 0.01 g/cm² surface area.

Embodiment 21 provides the method of any one of Embodiments 1-20, wherein the coating is sufficient to provide a weight gain of about 0.000.1 g/cm² surface area to about 0.1 g/cm² surface area.

Embodiment 22 provides the method of any one of Embodiments 1-21, wherein the environment comprising oxygen is about 1 vol % to about 50 vol % oxygen.

Embodiment 23 provides the method of any one of Embodiments 1-22, wherein the environment comprising oxygen is about 10 vol % to about 30 vol % oxygen.

Embodiment 24 provides the method of any one of Embodiments 1-23, wherein the heating is sufficient to melt at least part of the UHMWPE comprises heating to about 100° C. to about 400° C.

Embodiment 25 provides the method of any one of Embodiments 1-24, wherein the heating is sufficient to melt at least part of the UHMWPE comprises heating to about 140° C. to about 160° C.

Embodiment 26 provides the method of any one of Embodiments 1-25, wherein the heating is sufficient to melt at least part of the UHMWPE comprises heating for about 1 minute to about 7 days.

Embodiment 27 provides the method of any one of Embodiments 1-26, wherein the heating is sufficient to melt at least part of the UHMWPE comprises heating for about 1 hour to about 48 hours.

Embodiment 28 provides the method of any one of Embodiments 1-27, wherein about 1 wt % to about 100 wt % of the solid material comprising the UHMWPE is the UHMWPE.

Embodiment 29 provides the method of any one of Embodiments 1-28, wherein about 90 wt % to about 100 wt % of the solid material comprising the UHMWPE is the UHMWPE.

Embodiment 30 provides the method of any one of Embodiments 1-29, wherein obtaining or providing the solid material comprising the UHMWPE comprising a first concentration of free-radicals comprises irradiating a pre-irradiated solid material comprising the UHMWPE.

Embodiment 31 provides the method of any one of Embodiments 1-30, wherein the UHMWPE in the solid material comprising a first concentration of free-radicals comprises an irradiated UHMWPE.

Embodiment 32 provides the method of Embodiment 31, wherein the solid material comprising the UHMWPE comprises an irradiated solid material.

Embodiment 33 provides the method of any one of Embodiments 31-32, wherein the irradiated UHMWPE comprises at least one of an electron-beam irradiated and gamma irradiated UHMWPE.

Embodiment 34 provides the method of any one of Embodiments 31-33, wherein the irradiated UHMWPE comprises a UHMWPE that has been irradiated with a dose of irradiation of about 1 kGy to about 100,000 kGy.

Embodiment 35 provides the method of any one of Embodiments 31-34, wherein the irradiated UHMWPE comprises a UHMWPE that has been irradiated with a dose of irradiation of about 50 kGy to about 200 kGy.

Embodiment 36 provides the method of any one of Embodiments 1-35, wherein the antioxidant is a free-radical scavenger.

Embodiment 37 provides the method of any one of Embodiments 1-36, wherein the antioxidant comprises at least one of a tocopherol, a tocopherol phosphite, a tocotrienol, vitamin E, vitamin E acetate, vitamin E phosphite, rosemary oil, pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, bilberry extract, vitamin C, a carotene, a flavonoid, an isoflavonoid, a neoflavonoid, a lignin, quinine, ubiquinone, vitamin K1, a metal, glutathione, propyl gallate, octyl gallate, lauryl gallate, resveratrol, rosmarinic acid, rutin, 5-aminosalicylic acid, butylated hydroxy anisole, butylated hydroxy toluene, a phenolic compound, and a monomeric or polymeric hindered amine stabilizer.

Embodiment 38 provides the method of any one of Embodiments 1-37, wherein the antioxidant comprises at least one of vitamin E, vitamin E acetate, pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, and bilberry extract.

Embodiment 39 provides the method of any one of Embodiments 1-38, wherein the antioxidant comprises at least one of racemic alpha-tocopherol, RRR-alpha-tocopherol, SRR-alpha-tocopherol, SSR-alpha-tocopherol, SRS-alpha-tocopherol, SSS-alpha-tocopherol, RSR-alpha-tocopherol, RRS-alpha-tocopherol, RSS-alpha-tocopherol, racemic beta-tocopherol, RRR-beta-tocopherol, SRR-beta-tocopherol, SSR-beta-tocopherol, SRS-beta-tocopherol, SSS-beta-tocopherol, RSR-beta-tocopherol, RRS-beta-tocopherol, RSS-beta-tocopherol, racemic gamma-tocopherol, RRR-gamma-tocopherol, SRR-gamma-tocopherol, SSR-gamma-tocopherol, SRS-gamma-tocopherol, SSS-gamma-tocopherol, RSR-gamma-tocopherol, RRS-gamma-tocopherol, RSS-gamma-tocopherol, racemic delta-tocopherol, RRR-delta-tocopherol, SRR-delta-tocopherol, SSR-delta-tocopherol, SRS-delta-tocopherol, SSS-delta-tocopherol, RSR-delta-tocopherol, RRS-delta-tocopherol, and RSS-delta-tocopherol.

Embodiment 40 provides the method of any one of Embodiments 1-39, wherein the antioxidant is about 0.01 wt % to about 100 wt % of the liquid composition.

Embodiment 41 provides the method of any one of Embodiments 1-40, wherein the antioxidant is about 5 wt % to about 100 wt % of the liquid composition.

Embodiment 42 provides the melt-stabilized material of any one of Embodiments 1-41.

Embodiment 43 provides an orthopedic implant comprising the melt-stabilized material of any one of Embodiments 1-42.

Embodiment 44 provides a method of preparing an orthopedic implant comprising forming an orthopedic implant from the melt-stabilized material of any one of Embodiments 1-42.

Embodiment 45 provides a method of melt-stabilizing a material comprising UHMWPE, the method comprising:

obtaining or providing a solid material comprising about 90 wt % to about 100 wt % UHMWPE comprising a first concentration of free-radicals of at least about $1 \times 10^{15}$ spins/g, wherein the UHMWPE comprises an irradiated UHMWPE;

coating about 90% to about 100% of a surface of the solid material with a liquid composition comprising at least one antioxidant comprising at least one of vitamin E, vitamin E acetate, pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, and bilberry extract, to provide a coated solid material, wherein the antioxidant is about 5 wt % to about 100 wt % of the liquid composition, to provide a coated solid material;

heating the coated solid material in an environment comprising about 1 vol % to about 30 vol % oxygen, the heating sufficient to melt at least part of the UHMWPE, to provide a heated material; and solidifying the heated material, to provide a melt-stabilized material comprising UHMWPE comprising a second concentration of free-radicals of less than about $1 \times 10^{15}$ spins/g;

wherein the UHMWPE in a surface layer of the melt-stabilized material has an oxidation index that does not exceed 1.

Embodiment 46 provides a medical implant comprising: an oxygen-containing-environment-melt-stabilized material comprising UHMWPE, the melt-stabilized material being free of post-melt-stabilization oxidized surface layer removal greater than 3 mm depth, wherein the UHMWPE in a surface layer of the melt-stabilized material has an oxidation index that does not exceed 1.

Embodiment 47 provides the apparatus, method, composition, or system of any one or any combination of Embodiments 1-46 optionally configured such that all elements or options recited are available to use or select from.

What is claimed is:

1. A method of melt-stabilizing a material comprising ultra high molecular weight polyethylene (UHMWPE), the method comprising:

obtaining or providing a solid material comprising about 90 wt % to about 100 wt % UHMWPE comprising a first concentration of free-radicals of at least about $1 \times 10^{15}$ spins/g, wherein the UHMWPE comprises an irradiated UHMWPE;

coating about 90% to about 100% of a surface of the solid material with a liquid composition comprising at least one antioxidant comprising at least one of vitamin E, vitamin E acetate, pentaerythritol tetrakis(3-(3,5-di-tert-butyl-4-hydroxyphenyl)propionate), butanedioic acid dimethyl ester/4-hydroxy-2,2,6,6-tetramethyl-1-piperidine ethanol copolymer, tannic acid, and bilberry extract, to provide a coated solid material, wherein the antioxidant is about 5 wt % to about 100 wt % of the liquid composition, to provide a coated solid material with 0.00001 g/cm² to 0.1 g/cm² of the antioxidant;

heating the coated solid material in an environment comprising about 1 vol % to about 30vol % oxygen to 140° C. to 400° C., the heating is sufficient to melt at least part of the UHMWPE, to provide a heated material; and solidifying the heated material, to provide a melt-stabilized material comprising UHMWPE comprising a second concentration of free-radicals of less than about $1 \times 10^{15}$ spins/g;

wherein the UHMWPE in a surface layer of the melt-stabilized material has an oxidation index that does not exceed 1.

2. The method of claim 1, wherein the second concentration of free-radicals is about 1% to about 0.0001% of the first concentration of free-radicals.

3. The method of claim 1, wherein the coating is sufficient to penetrate a surface layer of the solid material.

4. The method of claim 1, wherein the coating is sufficient to provide a weight gain of about 0.0001 g/cm² surface area to about 0.1 g/cm² surface area.

5. The method of claim 1, wherein the environment comprising oxygen is ambient air.

6. The method of claim 1, wherein the heating sufficient to melt at least part of the UHMWPE comprises heating to about 150° C. to about 400° C.

7. The method of claim 1, wherein obtaining or providing the solid material comprising the UHMWPE comprising a first concentration of free-radicals comprises irradiating a pre-irradiated solid material comprising the UHMWPE.

8. The method of claim 1, wherein the irradiated UHMWPE comprises at least one of an electron-beam irradiated and gamma irradiated UHMWPE.

9. The method of claim 1, wherein the antioxidant further comprises at least one of a tocopherol, a tocopherol phosphite, a tocotrienol, vitamin E phosphite, rosemary oil, vitamin C, a carotene, a flavonoid, an isoflavonoid, a neoflavonoid, a lignin, quinine, ubiquinone, vitamin K1, a metal, glutathione, propyl gallate, octyl gallate, lauryl gallate, resveratrol, rosmarinic acid, rutin, 5-aminosalicylic acid, butylated hydroxy anisole, butylated hydroxy toluene, a phenolic compound, and a monomeric or polymeric hindered amine stabilizer.

10. A melt-stabilized material formed by the method of claim 1.

11. An orthopedic implant comprising a melt-stabilized material formed by the method of claim 1.

12. A method of preparing an orthopedic implant comprising forming an orthopedic implant from a melt-stabilized material formed by the method of claim 1.

13. The method of claim 1, wherein the first concentration of free-radicals is about $1 \times 10^{15}$ spins/gram to about $1 \times 10^{20}$ spins/g.

14. The method of claim 1, wherein the second concentration of free-radicals is about $1 \times 10^5$ spins/g to less than about $1 \times 10^{15}$ spins/g.

15. The method of claim 1, wherein the second concentration of free-radicals is about 0.1% to about 0.001% of the first concentration of free-radicals.

16. The method of claim 1, wherein the surface layer of the melt-stabilized material has an oxidation index of about 0.001 to about 1.

17. The method of claim 1, wherein the surface layer of the melt-stabilized material is a layer of about 0 mm deep to about 1 mm deep.

18. The method of claim 1, wherein the surface layer of the melt-stabilized material is a layer of about 0 mm deep to about 10 mm deep.

19. The method of claim 1, wherein the irradiated UHMWPE is UHMWPE that has been irradiated with a dose of irradiation of about 50 kGy to about 200 kGy.

20. A method of melt-stabilizing a material comprising ultra high molecular weight polyethylene (UHMWPE), the method comprising:

obtaining or providing a solid material comprising UHMWPE comprising a first concentration of free-radicals, wherein the solid material comprising the UHMWPE is a twice-irradiated solid material comprising the UHMWPE;

coating at least part of the solid material with a liquid composition comprising at least one antioxidant, to provide a coated solid material with 0.00001 g/cm² to 0.1 g/cm² of the antioxidant;

heating the coated solid material in an environment comprising oxygen to 140° C. to 400° C., the heating sufficient to melt at least part of the UHMWPE, to provide a heated material; and solidifying the heated material, to provide a melt-stabilized material comprising UHMWPE comprising a second concentration of free-radicals, wherein the second concentration of free-radicals is less than the first concentration of free-radicals.

* * * * *

UNITED STATES PATENT AND TRADEMARK OFFICE
CERTIFICATE OF CORRECTION

PATENT NO. : 10,184,031 B2  
APPLICATION NO. : 15/124454  
DATED : January 22, 2019  
INVENTOR(S) : Pletcher Page 1 of 3

It is certified that error appears in the above-identified patent and that said Letters Patent is hereby corrected as shown below:

On the Title Page

In Column 2, item (56) under "Other Publications", Line 10, delete "Jan. 1," and insert --Feb. 1,-- therefor On page 3, in Column 1, item (56) under "Foreign Patent Documents", Line 14, delete "141918" and insert --1421918-- therefor On page 3, in Column 2, item (56) under "Foreign Patent Documents", Line 16, delete "WO-2008029047" and insert --WO-2008092047-- therefor On page 3, in Column 2, item (56) under "Other Publications", Line 27, delete "Oct. 15," and insert --Oct. 16,-- therefor On page 3, in Column 2, item (56) under "Other Publications", Line 31, delete "Ap." and insert --Apr.-- therefor On page 3, in Column 2, item (56) under "Other Publications", Line 34, delete "Stablized" and insert --Stabilized-- therefor On page 4, in Column 1, item (56) under "Other Publications", Line 11, delete "10,2018"," and insert --10, 2018",-- therefor On page 4, in Column 1, item (56) under "Other Publications", Line 33, delete "UMWPE" and insert --UHMWPE-- therefor On page 4, in Column 1, item (56) under "Other Publications", Line 36, delete "ELECfRON" and insert --ELECTRON-- therefor Signed and Sealed this  
Fifth Day of May, 2020

Andrei Iancu  
*Director of the United States Patent and Trademark Office*

CERTIFICATE OF CORRECTION (continued)
U.S. Pat. No. 10,184,031 B2

On page 4, in Column 2, item (56) under "Other Publications", Line 68, delete "Oct. 3," and insert --Oct. 31,-- therefor On page 5, in Column 1, item (56) under "Other Publications", Line 26, after "Sep", insert --.--

On page 5, in Column 2, item (56) under "Other Publications", Line 17, delete "Aug. 25," and insert --Aug. 26,-- therefor On page 6, in Column 1, item (56) under "Other Publications", Line 5, delete "Jun. 25," and insert --Jun. 26,-- therefor On page 6, in Column 1, item (56) under "Other Publications", Line 44, delete "dated dated" and insert --dated-- therefor On page 6, in Column 1, item (56) under "Other Publications", Line 51, delete "Oct. 15," and insert --Oct. 16,-- therefor On page 7, in Column 2, item (56) under "Other Publications", Line 20, delete "25, 2011" and insert --26, 2011-- therefor On page 7, in Column 2, item (56) under "Other Publications", Line 20, delete "Jan. 32," and insert --Jan. 31,-- therefor On page 8, in Column 2, item (56) under "Other Publications", Line 22, delete "Morecular" and insert --Molecular-- therefor On page 8, in Column 2, item (56) under "Other Publications", Line 26, delete "molecularweight" and insert --molecular weight-- therefor On page 8, in Column 2, item (56) under "Other Publications", Line 27, delete "a-tocopherol" and insert --α-tocopherol-- therefor On page 8, in Column 2, item (56) under "Other Publications", Line 30, delete "a-tocopherol in y-irradiated" and insert --α-tocopherol in γ-irradiated-- therefor On page 8, in Column 2, item (56) under "Other Publications", Lines 33-34, delete "a-tocopherol upon y-irradiation" and insert --α-tocopherol upon γ-irradiation-- therefor On page 9, in Column 1, item (56) under "Other Publications", Line 19, delete "a-Tocopherol" and insert --α-Tocopherol-- therefor On page 9, in Column 1, item (56) under "Other Publications", Line 26, delete "Oral." and insert --Oral,-- therefor On page 9, in Column 2, item (56) under "Other Publications", Line 6, delete "a-tocopherol" and insert --α-tocopherol-- therefor

CERTIFICATE OF CORRECTION (continued)
U.S. Pat. No. 10,184,031 B2

On page 9, in Column 2, item (56) under "Other Publications", Line 29, delete "Vitamine" and insert --Vitamin-- therefor In the Claims In Column 37, Line 6, in Claim 1, delete "30vol %" and insert --30 vol %-- therefor In Column 38, Line 11, in Claim 14, delete "$1\times10^{15}$" and insert --$1\times10^{15}$-- therefor